US006140368A

United States Patent [19]
Kenyon et al.

[11] Patent Number: 6,140,368
[45] Date of Patent: Oct. 31, 2000

[54] NAPHTHOLS USEFUL IN ANTIVIRAL METHODS

[75] Inventors: George L. Kenyon, San Francisco, Calif.; Margaret Stauber, Germantown, Md.; Karl Maurer, Ross; Dolan Eargle, San Francisco, both of Calif.; Angelika Muscate, Loerrach, Germany; Andrew Leavitt, San Francisco, Calif.; Diana C. Roe, Newark, Calif.; Todd J. A. Ewing, San Francisco, Calif.; Allan G. Skillman, Jr., San Francisco, Calif.; Edward Arnold, Belle Mead, N.J.; Irwin D. Kuntz, Greenbrae; Malin Young, San Francisco, both of Calif.

[73] Assignees: The Regents of the University of California, Oakland, Calif.; Rutgers, The University of New Jersey, New Brunswick, N.J.

[21] Appl. No.: 09/072,484

[22] Filed: May 4, 1998

Related U.S. Application Data

[60] Provisional application No. 60/045,583, May 5, 1997.

[51] Int. Cl.[7] .................................................. A61K 31/175
[52] U.S. Cl. .......................... 514/593; 514/614; 514/621; 514/622; 534/560; 534/732; 534/733; 548/254; 564/56; 564/68
[58] Field of Search ...................................... 514/593, 614, 514/621–622; 534/560, 732–733; 548/254; 564/56, 58

[56] References Cited

U.S. PATENT DOCUMENTS

| | | | |
|---|---|---|---|
| 3,681,320 | 8/1972 | Franklin | 534/576 |
| 5,089,420 | 2/1992 | Albarella et al. | 436/166 |
| 5,468,469 | 11/1995 | Aszalos et al. | 514/150 |
| 5,508,407 | 4/1996 | Kaldor et al. | 546/169 |
| 5,521,161 | 5/1996 | Malley et al. | 514/45 |
| 5,589,510 | 12/1996 | Ono et al. | 514/590 |

FOREIGN PATENT DOCUMENTS

92/22610  12/1992  WIPO .

OTHER PUBLICATIONS

Alykov et al., "Study of the Precipitation of Aminoglycoside Antibiotics with Azo Compounds," *Zhurnal Analiticheskoi Khimii*, 38(10, Pt. 2), 1856–1861, Russian (Oct., 1983); *Journal of Analytical Chemistry of the USSR*, 38(10, Pt. 2), 1421–1426, English (Apr. 10, 1984).

Vila et al., "Absence of Viral Rebound After Treatment of HIV–Infected Patients with Didanosine and Hydroxycarbamide," *Lancet*, 350, 635–636 (Aug. 30, 1997).

Mohan et al., "Synthesis of Napthalenesulfonic Acid Small Molecules as Selective Inhibitors of the DNA Polymerase and Ribonuclease H Activities of HIV–1 Reverse Transcriptase," *J. Med. Chem.*, Vol. 37, No. 16 (1994), pp. 2513–2519. (Aug. 5, 1994).

Abstract of "Lower Toxicity Anti–HIV Drug Comprises Azo Dyes with Acid Functional Groups as Effective Ingredient," JP 05 170 646 A, Derwent Publications XP–002070685. (Jul. 9, 1993).

Åkerfeldt, Stig, "Aromatic Sulfonic Acids as Viral Inhibitors. Structure–Activity Study Using Rhino Adeno 3, Herpes Simplex, and Influenza Viruses," *J. Med. Chem.*, 14:7 (1971), pp. 596–600. (Jul, 1971).

Balzarini et al., "Comparative Inhibitory Effects of Suramin and Other Selected Compounds on the Infectivity and Replication of Human T–Cell Lymphotropic Virus (HTLV–111)/ Lymphadenopathy–Associated Virus (LAV)," *Int. J. Cancer*, 37 (1986), pp. 451–457. (Mar. 15, 1986).

Brinkworh and Fairlie, "Non–Peptide Anti–AIDS Agents; Inhibition of HIV–1 Proteinase by Disulfonates," *Biochem. Biophys. Res. Commun.*, 188:2 (1992), pp. 624–630. (Oct. 30, 1992).

Mohan et al., "Novel Naphthalenedisulfonic Acid Anti–HIV–1 Agents. Synthesis and Activity Against Reverse Transcriptase, Virus Replication and Syncytia Formation," *Drug Design and Discovery*, 8 (1991), pp. 69–82.

Weaver et al., "Inhibition of the Binding of HIV rgp 120 to CD4 by Dyes," *Antivir. Chem. Chemother.*, 3:3 (1992), pp. 147–151.

PCT International Search Report of PCT/US98/08815 (foreign filing relating to present U.S. application), mailing date Jul. 27, 1998.

*Primary Examiner*—Gary Geist
*Assistant Examiner*—L. Eric Cane
*Attorney, Agent, or Firm*—Majestic, Parsons, Siebert & Hsue P.C.

[57] ABSTRACT

The present invention relates to a novel class of compounds that are potent inhibitors of HIV reverse transcriptase and HIV integrase. In addition to being multienzyme inhibitors, the inventive compounds of the present invention are remarkable in at least two other respects. First, they do not appear to be toxic to cells at typical therapeutic concentrations. Second, they appear to be equally effective against mutant strains of HIV reverse transcriptase commonly found in patients who have developed resistance to current reverse transcriptase inhibitors. Because the inventive compounds show promise in combatting viral resistance and are potent inhibitors of both HIV reverse transcriptase and integrase, they are ideal candidates for use in combination with existing therapies or alone in treating AIDS or HIV infection.

13 Claims, 1 Drawing Sheet

NAPHTHOLS USEFUL IN ANTIVIRAL METHODS

CROSS-REFERENCE TO RELATED APPLICATION

This is an application based on provisional patent application Ser. No. 60/045,583, filed May 5, 1997, now abandoned, and priority therefrom is hereby claimed.

This invention was made with Government support under Grant No. GM39552, awarded by the National Institute of Health. The Government has certain rights in this invention.

FIELD OF THE INVENTION

The present invention generally relates to naphthols useful as dyes and color indicators, more particularly to naphthols with antiviral properties for applications in the fields of virology and molecular medicine, and more specifically, to novel compounds that reduce or inhibit the activities of two key enzymes in the HIV life cycle, reverse transcriptase and integrase.

BACKGROUND OF THE INVENTION

A great variety of naphthols are known and useful as dyes and color indicators. Among these are naphthalene sulfonic acid compounds such as calcomine orange, which has been taught useful as an inert background dye in assaying peroxidatively active substances by U.S. Pat. No. 5,089,420, issued Feb. 18, 1992, inventors Albarella et al. Calcomine orange has been reported (Available Chemicals Database) to have the asymmetrical structure shown by Compound A:

COMPOUND A

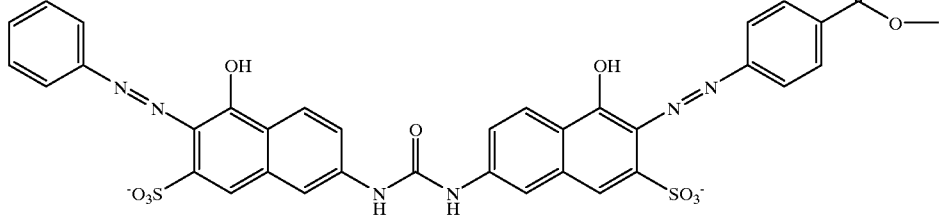

U.S. Pat. No. 5,589,510, issued Dec. 31, 1996, inventors Ono et al., disclose a method for inhibiting retroviral infection by administering a naphthalenesulfonic acid compound represented by the Compound B:

COMPOUND B

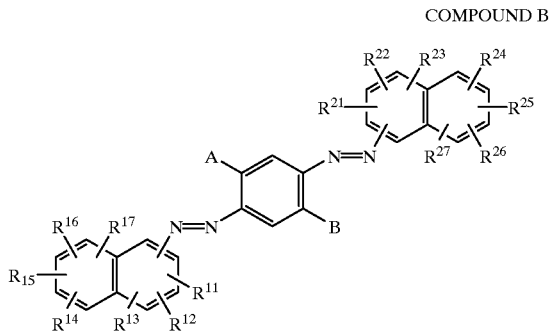

wherein $R^{11}$ to $R^{27}$ are individually selected from the group consisting of hydrogen atom, hydroxyl group, amino group which is optionally substituted with alkyl or aryl groups, sulfo groups, carboxyl groups, amide group which is optionally substituted with alkyl or aryl groups, acylamino groups, sulfonamide groups, sulfonylamino groups, alkoxy groups and halogen atoms; provided that at least one of $R^{11}$ to $R^{17}$ is hydroxyl or amino group, at least one of $R^{21}$ to $R^{27}$ is hydroxyl or amino group, at least one of $R^{11}$ to $R^{17}$ is sulfo group, and at least one of $R^{21}$ to $R^{27}$ is sulfo group; A and B are individually selected from the group consisting of hydrogen atom, alkyl ($C_1$–$C_4$) groups, alkoxy ($C_1$–$C_4$) groups, and halogen atoms.

There have also been reported some naphthol compounds considered "confirmed active" in AIDS antiviral screens. These include calcomine scarlet 4BNC (CAS Registry No. 5893323), direct fast scarlet 4BSW (CAS Registry No. 6420446), and brilliant paper scarlet G (CAS Registry No. 6460011). However, these just noted naphthol dyes all contain three or more sulfonic acid groups. The calcomine scarlet 4BNC, for example, is 2-naphthalenesulfonic acid, 7-[(4-aminobenzoyyl)amino]-3-[[4-[(2,5-dichloro-4-sulfophenyl)azo]-2-ethoxy-6-sulfo-1-naphthalenyl]azo]-4-hydroxy-,trisodium salt (9CI).

Human immunodeficiency virus ("HIV"), a retrovirus in the lentivirus family, is believed to be the etiological agent of acquired immunodeficiency syndrome ("AIDS"). Chemotherapeutic strategies for treating AIDS or HIV infection have traditionally targeted critical enzymes in the viral life cycle. For example, HIV reverse transcriptase, which is necessary to convert the RNA-based viral genome to DNA, continues to be a target of drug therapy. More recently, the focus has shifted to multiple enzymatic targets such as the combination of reverse transcriptase and protease.

Currently used reverse transcriptase inhibitors fall into two categories. The nucleoside analogue inhibitors such as 3'-azido-3'-deoxythymidine ("AZT"), dideoxyinosine ("ddI"), and dideoxycytidine ("ddC") are deoxynucleoside mimics. These compounds are converted into triphosphate forms by intracellular enzymes and inhibit reverse transcriptase mediated DNA synthesis by acting as DNA chain terminators. However, presumably because of the cross reactivity with host polymerases, the side effects are notoriously severe and generally limit the therapeutic index of this class of drugs to relatively low levels.

The non-nucleoside inhibitors include nevirapine, tetrahydroimidazo-[4,5,1-jk] benzodiazepine-2(1H)-thione ("TIBO"), 1-[(2-hydroxyethoxy)-methyl]-6-(phenylthio) thimine ("HEPT"), and 2-pyridone derivatives. These compounds bind to an allosteric site on reverse transcriptase and are believed to inhibit the enzyme by affecting its conformational flexibility. Although this class of drugs has minimal side effects, because of the rapid development of viral resistance, these drugs become virtually ineffective typically within about six weeks.

In an effort to stem the development of viral resistance, combination therapies attacking multiple enzymatic targets have been recently advocated. For example, various protease inhibitors have been successfully combined with nucleoside inhibitors such as AZT and have reduced blood virus counts to virtually undetectable levels in some patients. However, this remarkable response is not reproduced in all patients. Moreover, in addition to the punishing side effects, users of protease inhibitors often must follow a demanding treatment regimen, with the risk that if a few doses are skipped, any advantage of the combination in stemming viral resistance may be lost.

The earlier noted U.S. Pat. No. 5,589,510 suggests use of its naphthalene sulfonic acid compounds in administration with other known HIV-reverse transcriptase inhibitors, such as AZT. Nevertheless, a need exists for new drugs against the HIV virus, particularly those that could be effective in inhibiting multiple enzymes necessary for the HIV virus. Ideally, these new drugs would only selectively target the virus and produce minimal patient side effects. Moreover, based upon the success of current combination therapies, the new drugs should be adaptable for use in such therapies by either attacking at novel targets for use with one or more existing drugs, or attacking multiple targets by themselves.

SUMMARY OF THE INVENTION

In one aspect of the present invention, novel naphthols are provided that are useful as dyes and color indicators. These novel compounds have been discovered to have anti-viral properties against retroviruses, particularly to be inhibitors of HIV reverse transcriptase and/or HIV integrase. It is particularly advantageous to have a drug with multiple sites of attack, such as to be an inhibitor of both reverse transcriptase and integrase, as here.

The inventive naphthols have the general formula:

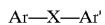

wherein Ar is a naphthol substituted with anionic groups or groups readily converted to anionic groups, provided that there are no more than two sulfonic acid groups on the molecule, Ar' is a substituted or unsubstituted aryl ($C_6$–$C_{12}$) or substituted or unsubstituted heteroaryl ($C_1$–$C_{12}$), and X is a substantially rigid linker preferably attached via amide (or amide analogous) bonds. Amide analogous bonds include vinylogous amides. A particularly preferred linker is the urea linker (—N(CO)N—). However, other examples of suitable linkers include but are not limited to: —N(CS)N— (thiourea); —N(CO)(CO)N— (oxalyl); —N(CO)C(CO)N— (malonyl); —N(CO)O— (carbamate); and —N(CO)CH$_2$CH$_2$(CO)N— (succinyl), as well as moieties with aromatic rings, squarates, and cage structures.

One group of preferred compounds of the present invention are of the formula:

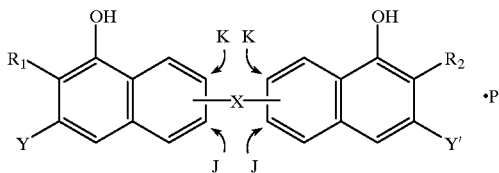

wherein $R_1$ and $R_2$ individually is selected from a group consisting of substituted aryl ($C_6$–$C_{12}$), unsubstituted aryl ($C_6$–$C_{12}$), substituted heteroaryl ($C_1$–$C_{12}$) and unsubstituted heteroaryl ($C_1$–$C_{12}$), which are bound via an azo or amide group, provided that neither $R_1$ nor $R_2$ contains a sulfonic acid group, Y and Y' each is an anionic moiety, such as sulfonic, carboxylic and tetrazol, or one readily converted to anionic, such as sulfonic acid ester and sulfonic acid thioester, and X is a linker as above described, which is bonded through amide or amide analogous bonds by a "J" or a "K" position link. "P" is one or more counterions, such as protons, alkali, metal, or alkaline earth cations.

For example, many of the preferred compounds with confirmed retroviral activity have the structure

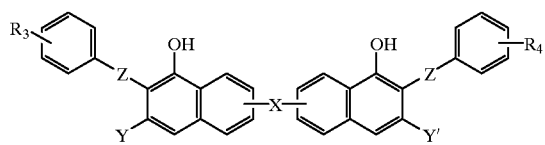

wherein Y, Y', and X are as already described, Z is an azo or amide linkage, and one or both of $R_3$ and $R_4$ include a readily ionizable group, such as a carboxyl, a trizol, or a tetrazol group.

Two examples of particularly preferred embodiments of the invention are the salts or protonated species:

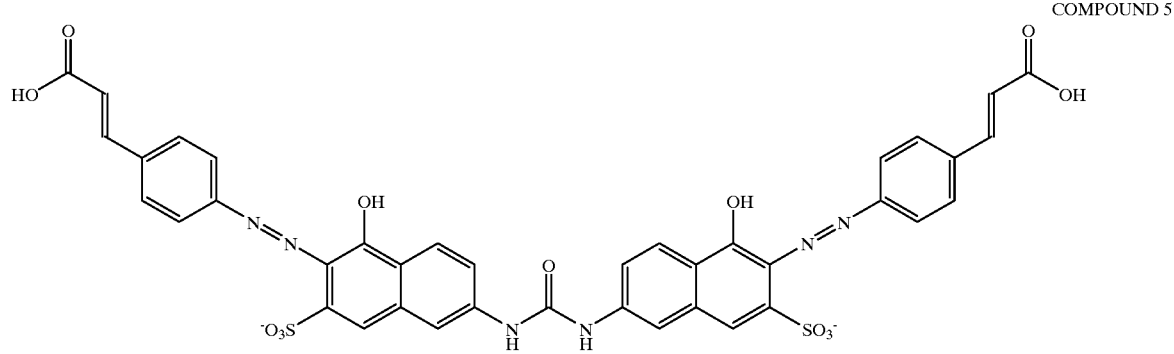

COMPOUND 5

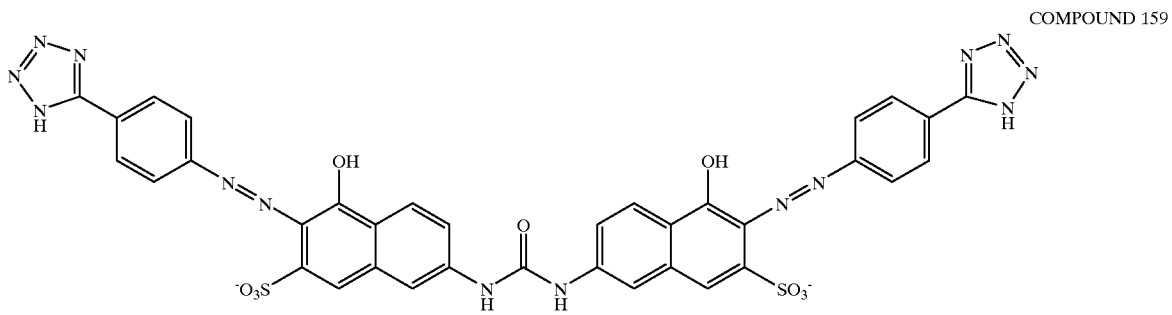

COMPOUND 159

The $IC_{50}$ for Compound 5 has been tested as 200 nM and that of Compound 159 at 220 nM. In cell-based anti-HIV (XTT) assays, Compound 5 was confirmed active.

In another aspect of the invention, methods for inhibiting HIV reverse transcriptase and/or integrase and methods for inhibiting HIV replication are provided that comprise administering an effective amount of at least one inventive compound or a salt thereof. Because the inventive compounds show promise in combating viral resistance and are potent inhibitors of both HIV reverse transcriptase and integrase, they are ideal candidates for use in combination with existing therapies or alone in treating AIDS or HIV infection.

In yet another aspect of the invention, pharmaceutical compositions are provided which comprise at least one inventive compound (or salt thereof) in association with a pharmaceutically acceptable carrier, diluent or excipient. Particularly preferred pharmaceutical compositions are formulated for topical application in treating retroviral diseases such as herpes simplex.

DETAILED DESCRIPTION OF THE INVENTION

Figure 1:
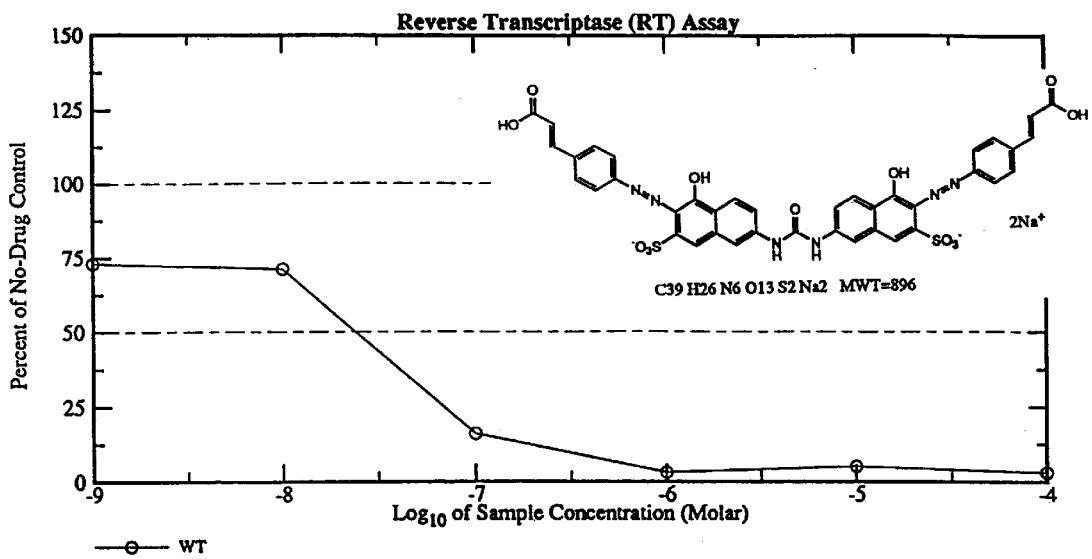
FIG. 1 graphically illustrates the results of a reverse transcriptase (RT) assay for an embodiment of the invention designated "Compound 5;" and, FIG. 2 graphically illustrates a cell-based anti-HIV (XTT) assay for the Compound 5 embodiment.

Compounds of this invention are naphthols that may be used as dyes and color indicators; however, because these compounds have anti-viral properties against retroviruses they are contemplated for use in virology applications. In particular, the compounds are potent inhibitors of HIV reverse transcriptase and/or integrase.

The novel inhibitors of the present invention are a result of structure-based drug design efforts using the 2.8 Å crystal structure of HIV reverse transcriptase complexed to DNA. Small molecules were individually "docked" to binding sites in the enzyme and evaluated as potential lead compounds.

So that the number of synthesized compounds is minimized, a database containing only commercially available compounds was used. An example of a database of this type is the Available Chemicals Database distributed by Molecular Design Limited (San Leandro, Calif.).

A lead compound that emerged was carbonyl-J ("Compound 1").

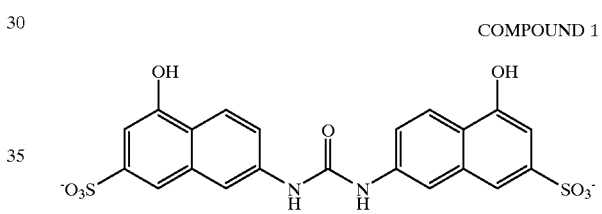

COMPOUND 1

Carbonyl-J inhibited the activity of HIV reverse transcriptase with an $IC_{50}$ of approximately 5 micromolar ("$\mu M$"). $IC_{50}$ is the concentration at which the compound inhibits 50 percent of the enzyme's activity.

Continuing the strategy of minimum synthesis, the initial derivatives of carbonyl-J were found by searching the database of commercially available compounds. However, this time, instead of focusing on a particular compound's interaction with the enzyme, the search focused on structural similarity to carbonyl-J. A notable result from this effort was the identification of "calcomine orange" which was found by us to inhibit the HIV reverse transcriptase with an $IC_{50}$ of 1.5 $\mu M$. Although calcomine orange was purportedly a known compound, we found there to be ambiguity in its actual structure, as discussed below. Although calcomine orange has been known and used as a dye, it has not been known for biological properties.

The reported structure for calcomine orange was determined to be incorrect. According to the Available Chemicals Database, the structure of calcomine orange is asymmetrical, as shown by Compound A.

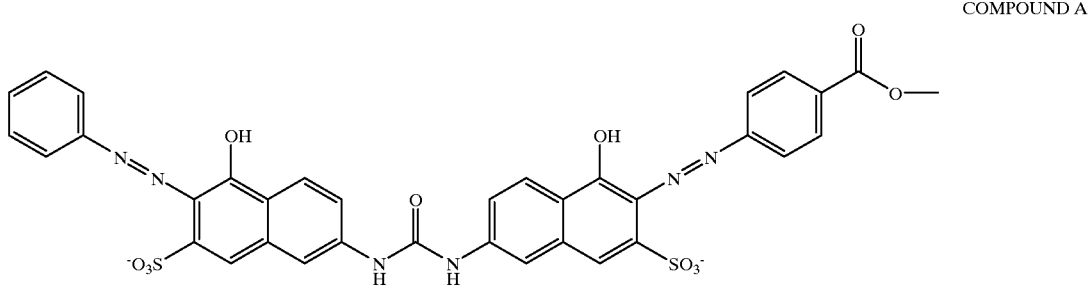

COMPOUND A

However, based upon a series of NMR experiments, it has been discovered that the commercially available sample of calcomine orange is actually a symmetrical diphenyl species which lacks the reported carboxylic functionality, as shown by Compound C. It is possible that the asymmetrical Compound A structure was present as a contaminant in the commercially obtained source.

substituents are where there is an anionic group on each of Ar and Ar'; however, there should be no more than two sulfonic acid groups on the compound. The X linker is attached to the Ar and Ar' groups by amide bonds or, in the case of certain linkers within the scope of this invention, by amide analogs such as vinylogous amide and thiourea bonds. A particularly preferred linker is the urea linker

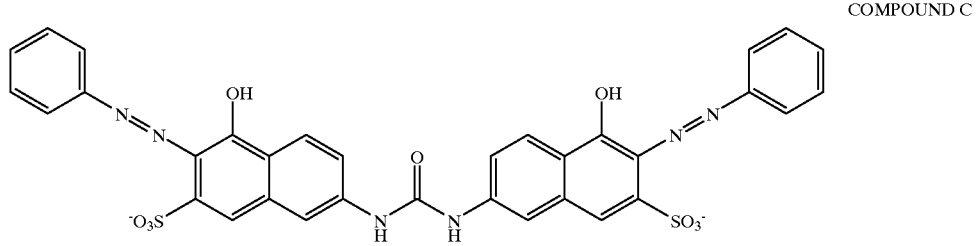

COMPOUND C

In addition to inhibiting reverse transcriptase which translates the viral RNA-based genome into DNA, carbonyl-J and the tested calcomine orange (Compound C) also inhibit HIV integrase. Also a critical enzyme, integrase is involved in two separate reactions and is so named because of its involvement in stably "integrating" viral DNA into host DNA. The first reaction is termed "3' processing" and is the transesterification of the 3' end of the viral DNA in the cytoplasm. The second is termed "strand transfer" and involves another transesterification reaction in the nucleus which attaches the 3' end of the viral DNA to host DNA. Notably both carbonyl-J and calcomine orange are also potent integrase inhibitors with $IC_{50}$ values of 2.5 $\mu$M and 2.0 $\mu$M, respectively, for both the 3' processing and strand transfer activities.

Using both carbonyl-J and calcomine orange as lead compounds, analogs that also inhibit reverse transcriptase and/or integrase were prepared.

In general, compounds of the present invention may be described by the formula:

Ar—X—Ar' wherein Ar is a naphthol substituted with an anionic moiety or with a group readily converted to an anionic moiety, such as an ester, provided that when the anionic group is sulfonic acid there are no more than two present and Ar' is a substituted or unsubstituted aryl ($C_6$–$C_{12}$) or substituted or unsubstituted heteroaryl ($C_1$–$C_{12}$) and X is a substantially rigid linker. Preferably Ar' is also a naphthol, and both Ar and Ar' are substituted with anionic moieties such as sulfonic, carboxylic, or tetrazol groups, or with an ester such as sulfonic acid ester and sulfonic acid thioester. Typical (—N(CO)N—). Other examples of suitable linkers include but are not limited to: —C(CS)C— (thiourea); —N(CO)(CO)N— (oxalyl); —N(CO)C(CO)N— (malonyl); —N(CO)O— (carbamate); and —N(CO)CH$_2$CH$_2$(CO)N— (succinyl), aryls or heteroaryls, squarates, and cage structures. For example, where X includes an aromatic ring, then some suitable moieties include

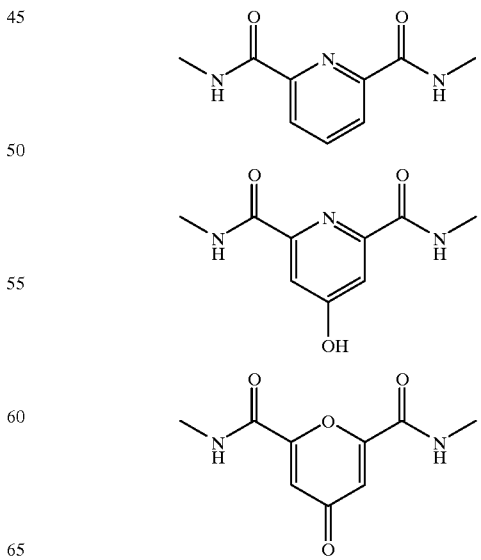

Other pyridine dicarboxylic acids may be used in preparing linkers, as can a wide variety of other aryls, heteroaryls, cage structures, and squarates, all of which are substantially rigid.

Generally, preferred compounds of the present invention are of the formula:

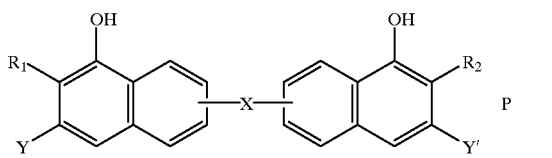

wherein $R_1$ and $R_2$ individually is selected from a group consisting of substituted aryl ($C_6$–$C_{12}$), unsubstituted aryl ($C_6$–$C_{12}$), substituted heteroaryl ($C_1$–$C_{12}$) and unsubstituted heteroaryl ($C_1$–$C_{12}$), which are bound via an azo or amide group, provided that neither $R_1$ nor $R_2$ contains a sulfonic acid group, Y and Y' each is an anionic moiety, such as sulfonic, carboxylic and tetrazol, or one readily converted to anionic such as sulfonic acid ester and sulfonic acid thioester, and X is a linker as above described, which is bonded through amide or amide analogous bonds by a "J" or a "K" position link. "P" is one or more counterions, such as protons, alkali, metal, or alkaline earth cations.

Synthesis of compounds having such linkages as herein described are well established in the art, and any standard techniques described in the literature may be used, such as those outlined by Jerry March, *Advanced Organic Chemistry*, 4th Ed., John Wiley & Sons (1992), which is incorporated herein in its entirety by reference. For example, where X is an urea linker, one series of derivatives can be prepared by reacting 7-amino-4-hydroxynaphthalene-2-sulfonic acid (herein referred to as "J acid" (6)) with p-nitrophenylchloroformate. As shown by scheme 1, an activated intermediate is formed which is then reacted with the desired functionalized amine to form the urea product (5).

SCHEME 1

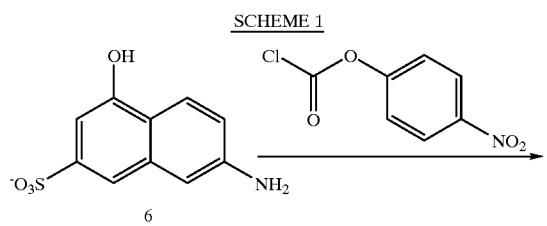

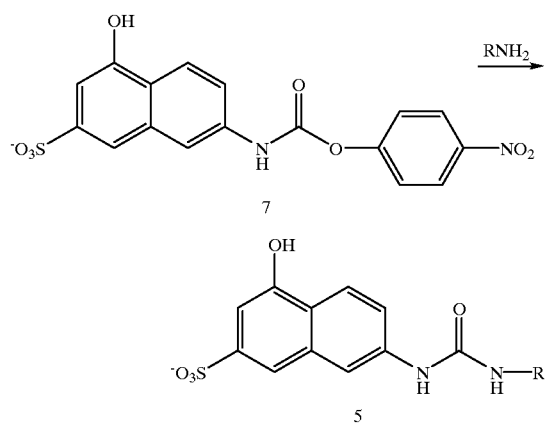

Another strategy involves reacting an isocyanate with J-acid. Scheme 2 illustrates this protocol.

SCHEME 2

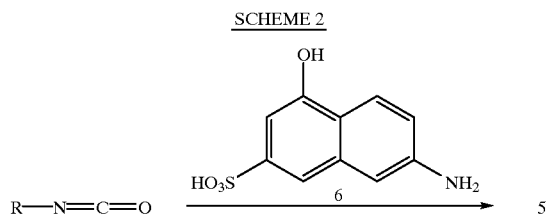

So that analogs may be quickly synthesized, synthetic strategies focused on using commercially available starting materials where possible. For example, many symmetric urea analogs of carbonyl-J have been synthesized using commercially available materials.

Synthetic strategies for making calcomine orange analogs are also straightforward. As seen from the structures, calcomine orange contains carbonyl-J as its core structure with additional phenyl groups linked by azo bridges. Taking advantage of the azo linkages, one strategy for making amine or amide analogs is outlined in scheme 3.

SCHEME 3

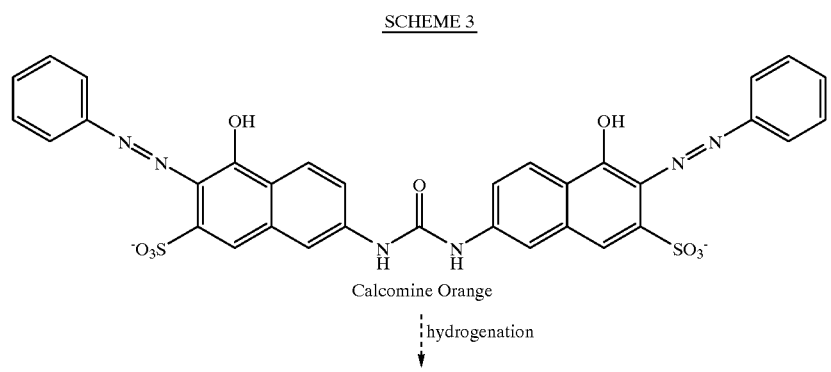

Calcomine Orange hydrogenation

-continued

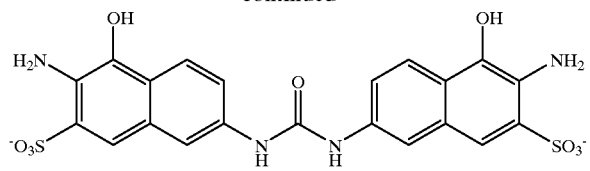

11 acylation or
other modification
of the amine group

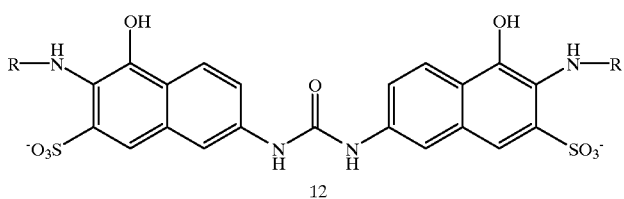

12

Another strategy is outlined in scheme 4 which takes advantage of the hydroxyl functionality directing the azo coupling to a position on a naphthalene ring. The coupling is performed by reaction of an aryl diazonium salt (which can be prepared from a wide variety of aromatic and heteroaromatic amines) with a suitably reactive aromatic receptor (i.e. carbonyl-J, J-acid).

SCHEME 4

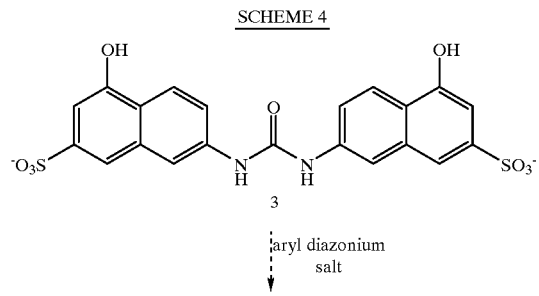

3 aryl diazonium
salt

-continued

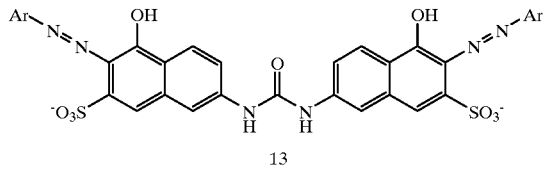

13

(Ar = aryl group)

Although particular synthetic strategies have been outlined herein, it is to be understood that compounds of the present invention may be synthesized by any method known in the art.

Two examples of particularly preferred embodiments of the invention are:

COMPOUND 5

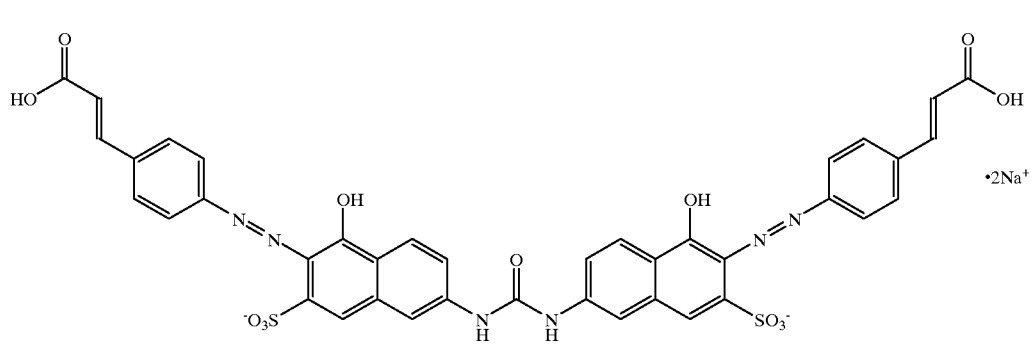

•2Na⁺

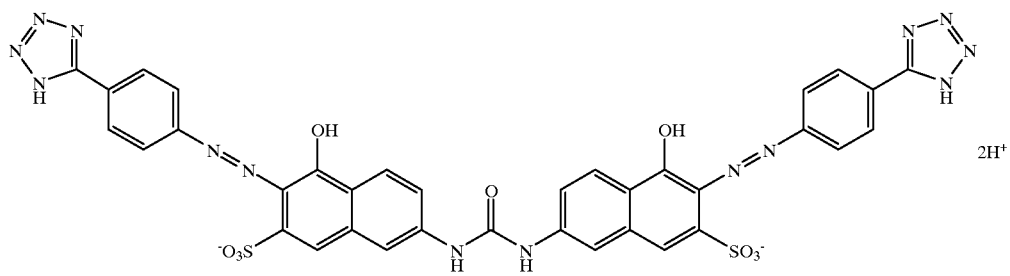

COMPOUND 159

The IC$_{50}$ for Compound 5 has been tested as 200 nM and that of Compound 159 at 220 nM. In cell-based anti-HIV (XTT) assays, Compound 5 was confirmed active.

In addition to being multienzyme inhibitors, the compounds of the present invention are remarkable in at least two other respects. First, the inventive compounds do not appear to be toxic to cells in the concentration ranges contemplated in the present invention. For example, as measured by growth curves and trypan blue exclusion of 293T cells, Compound 5 was not toxic even at concentrations greater than ten times its IC$_{50}$ against HIV reverse transcriptase (IC$_{50}$=200 nM.

Second, the inventive compounds appear to be equally effective against mutant strains of HIV reverse transcriptase commonly found in patients who have developed resistance to current reverse transcriptase inhibitors. For example, mutant reverse transcriptase of highly resistant viruses revealed at least one the following amino acid changes: D67N, K70R, T215F/Y, K219Q, and M41L. When carbonyl-J (Compound 1) was tested against a mutant reverse transcriptase containing all of the above mutations (M41L/D67N/K70R/T215Y/K219Q), virtually no difference in inhibition was found with respect to the wild type enzyme. As a result, neither toxicity nor viral resistance appears to be a significant problem with the therapeutic use of the inventive compounds.

As stated previously, the compounds of the present invention may be used to inhibit or reduce the activities of HIV reverse transcriptase and/or HIV integrase. Methods for inhibiting these critical enzymes generally comprise administering an effective amount of at least one of the inventive compounds. As used herein, the term "effective amount" means an amount of an inventive compound which is capable of inhibiting or reducing the activity of HIV reverse transcriptase from copying single stranded RNA into double stranded DNA. However, because the compounds of the present invention are generally dual enzyme inhibitors, the term "effective amount" can also mean an amount of the inventive compound which is capable of inhibiting or reducing the activity of HIV integrase from either 3' processing or mediating DNA strand transfer or both.

Because both reverse transcriptase and integrase are necessary for replication, the compounds of the present invention may be used to inhibit, reduce, and prevent viral replication. Thus, methods for reducing or inhibiting viral replication comprise contacting an infected cell with an effective amount of one or more inventive compounds. Similarly, methods for reducing or inhibiting or preventing viral infectivity also comprise administering an infected mammal or a human patient with a suitable form of one or more of the inventive compounds.

The specific amount of an administered compound of course will depend on a number of inter-related factors including but not limited to the form of the compound, potency, mode of administration, bioavailability, age, sex and condition of the patient, all of which can be determined and assessed by one skilled in the art. For example, the potency of an individual compound may be quantified directly using enzymatic measurements, cell culture assays, or viral blood counts, or indirectly by monitoring patient progress.

Although the values may be outside of these ranges, typically, the amount or dosage per mammal or patient body weight can vary from about 0.001 mg/kg to about 150 mg/kg, and preferably between about 0.1 mg/kg and about 50 mg/kg, in one or more daily dose administrations during the course of treatment. For intravenous injection, the dose may be about 0.1 to about 30 mg/kg/day, preferably about 0.5 to about 10 mg/kg/day. If applied topically as a liquid, ointment, or cream, the compound may be present in an amount of about 0.1 to about 50 mg/ml, preferably about 0.5 to 30 mg/ml of the composition.

Another aspect of the present invention is a pharmaceutically acceptable therapeutic composition comprising one or more inventive compounds. As with dosage, the identity and the number of inventive compounds will depend on the particular circumstances. An illustrative example may include two inventive compounds where one corresponds to the most potent reverse transcriptase inhibitor and the other corresponds to the most potent integrase inhibitor. Other factors dictating the identities of the inventive compounds include but are not limited to the mode of administration, solubility (if an aqueous composition), bioavailability, therapeutic index, and half-life. In any event, although the value may be outside of this range, the total amount of the inventive compound generally is between about 1 percent and about 90 percent by weight of the formulation.

The inventive composition may further include a pharmaceutically acceptable carrier. The term "pharmaceutically acceptable" refers to materials that are compatible with the other ingredients and are not deleterious to the recipient thereof. Examples of suitable pharmaceutically acceptable carriers include, but are not limited to, buffered saline, glycols, glycerols, vegetable oils, and organic esters, and may be present in an amount between about 0.1 percent and about 90 percent by weight, and more preferably between about 20 percent and about 60 percent by weight of the formulation.

Other optional ingredients include property enhancing agents including but not limiting to stabilizers, absorption modifying agents, wetting agents, emulsifying agents, dispersing agents, biocides, preservatives, and flavoring agents, all of which are well known in the pharmaceutical art. Such property enhancing agents may be present in an amount between about zero and about 40 percent by weight, and more preferably between about 0.01 and about 20 percent by weight of the composition.

Moreover, depending on the specific circumstances, the inventive compositions may further include drug delivery vehicles such as liposomes, microspheres, or other polymer matrices. A representative publication detailing the current art is Liposome Technology, published by CRC Press in 1993, which is incorporated herein by reference.

The pharmaceutical compositions of the present invention may be in any acceptable form such as a solution, emulsion, suspension, lotion, ointment, cream, granule, powder, tablet, capsule, sachet, lozenge, ampule, or suppository, and may be administered by any method known in the art including but not limited to parenterally, intramuscularly, subcutaneously, intravenously, transdermally, orally, or topically.

Because the inventive compounds are both reverse transcriptase and integrase inhibitors that appear to be relatively unaffected by mutant virus strains, the pharmaceutical compositions of the present invention are particularly suited for combination therapy either alone or with other known antiviral agents. For example, the inventive pharmaceutical compositions either may include (or used in conjunction with) any combination of antiviral compounds. Examples include, but are not limited to, other reverse transcriptase inhibitors such as AZT, ddC, DDI, TIBO derivatives, tricyclic diazepinones, and other inhibitors of HIV enzymes such as integrase and protease. The dosages of current antiviral compounds used in the treatment of HIV infection are known in the art.

In addition, the compounds of the present invention are believed therapeutically useful in other disease states that involve retroviral replication, which are apparent to one of ordinary skill in the art upon reading this specification in light of other available knowledge. Insofar as that is the case, the treatment of various retroviral mediated disease states is meant to be encompassed herein.

Structures of representative, novel compounds of the present invention include but are not limited to those illustrated in Table 1. It is to be understood that any of the disclosed linkers, such as thiourea, oxalyl, malonyl, carbamate, and succinyl linkers, may be substituted in these illustrative structures.

Functional groups of the inventive compounds may be interchangeably illustrated in a generalized form or in a particularized form or as a salt thereof. However, all readily converted forms of the inventive compounds, whether illustrated in the tables or not, are within the scope of the present invention. For example, the sulfonic acid functionality, when present as the anionic substitutent Y and Y', of the inventive compounds are illustrated interchangeably in a generalized form ("SO$_3$X" referring to ionized, unionized or a salt form thereof), or in a particularized form (e.g., ionized (SO$_3^-$); un-ionized (SO$_3$H); or as a sodium salt thereof (SO$_3^-$ Na$^+$)). Additionally, where a group is written in the center of an aromatic ring, this indicates that the group is attached to all unsubstituted positions of the ring. For example, in Compound 98, fluorene is attached at all positions except ring position 1 (attachment site to rest of molecule) and ring position 4 (carboxyl substituent).

TABLE 1

NOVEL COMPOUNDS

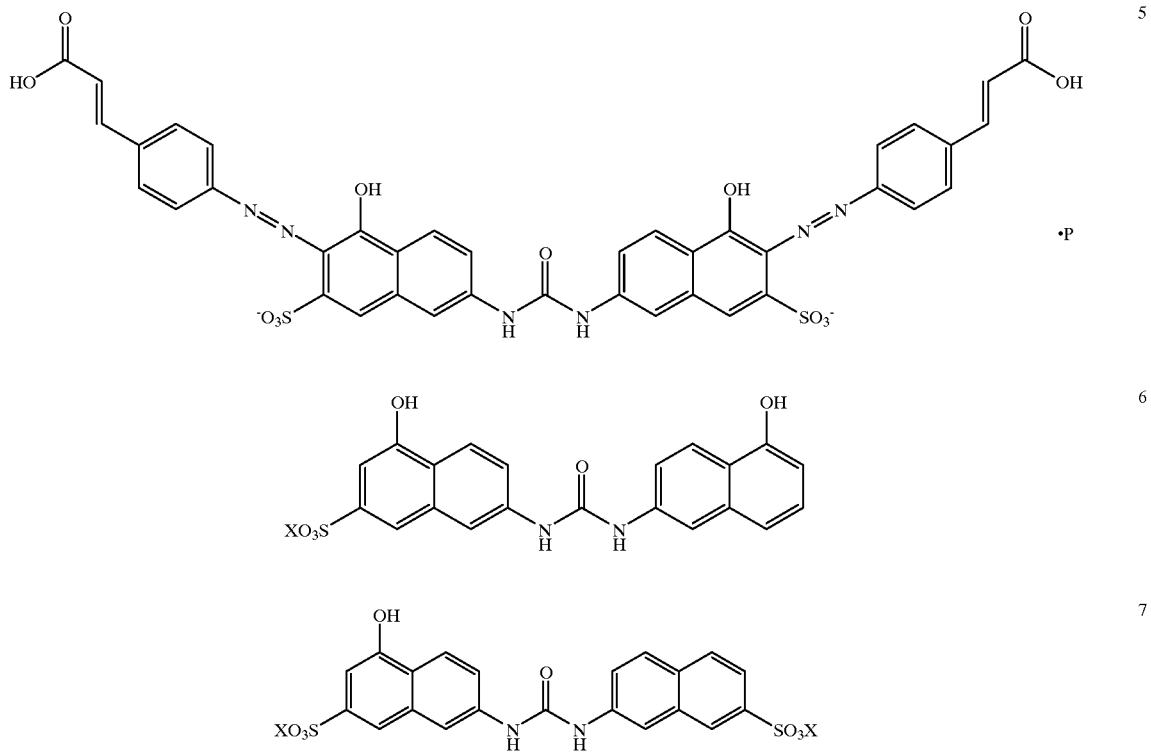

TABLE 1-continued
NOVEL COMPOUNDS
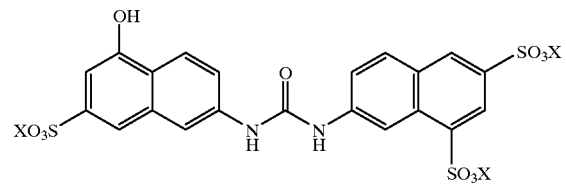
8
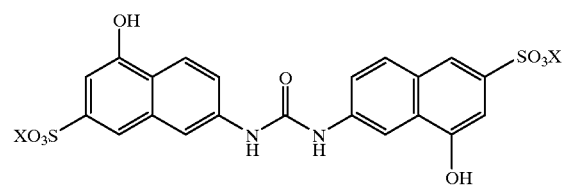
9
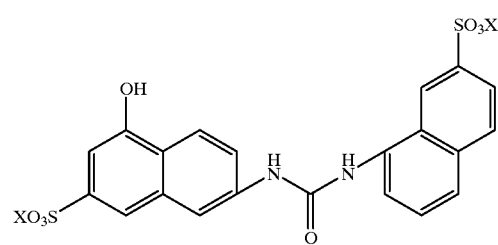
10
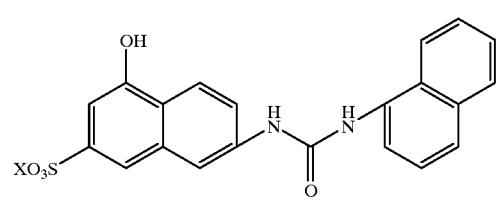
11
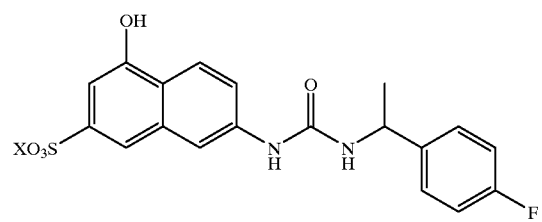
12
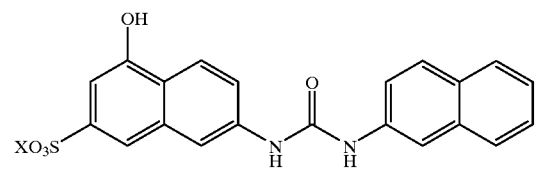
13
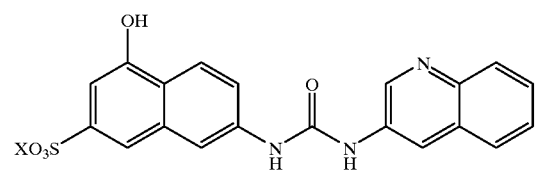
14

TABLE 1-continued
NOVEL COMPOUNDS
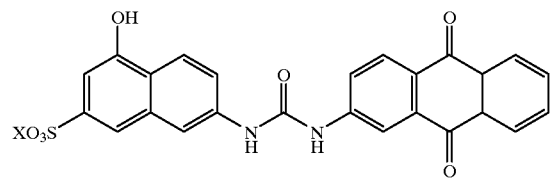
15
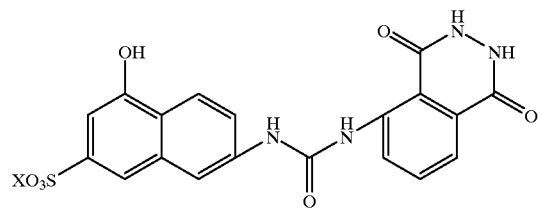
16
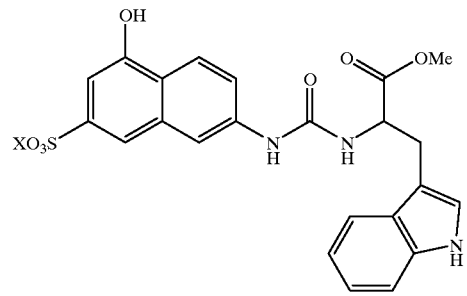
17
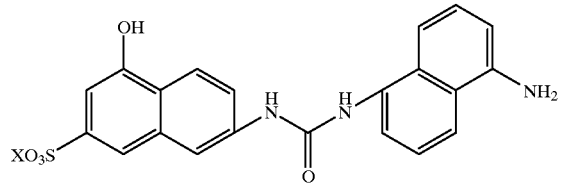
19
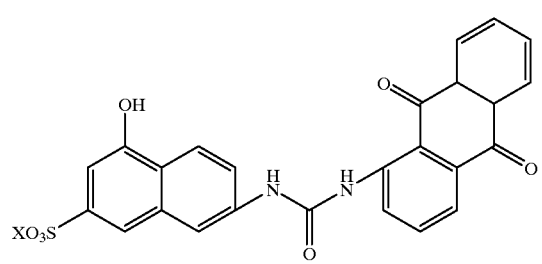
20
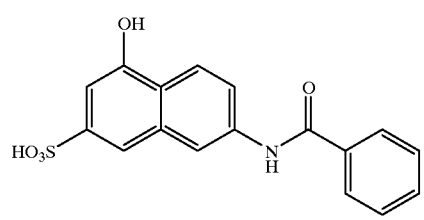
21

TABLE 1-continued
NOVEL COMPOUNDS
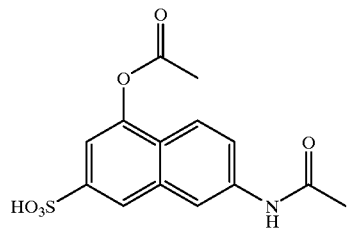
22
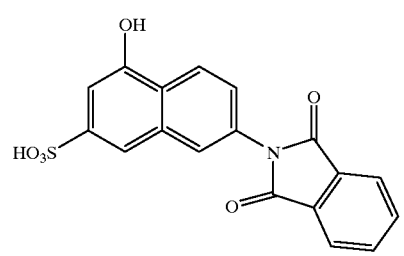
23
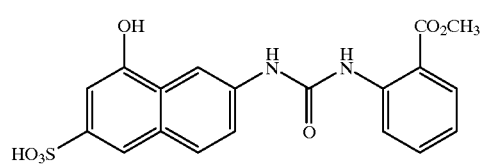
24
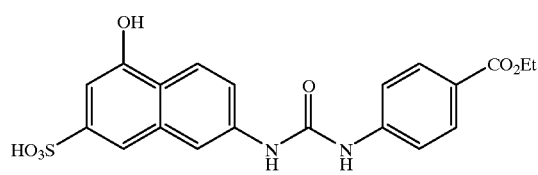
25
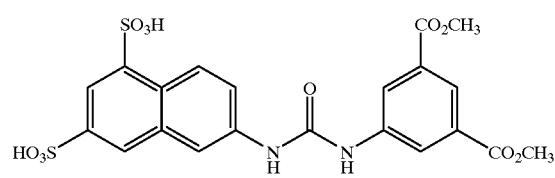
26
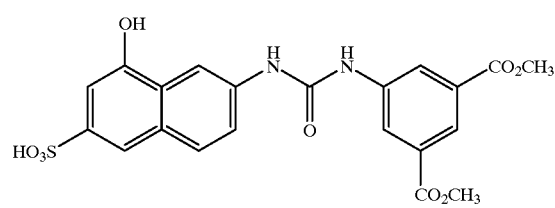
27
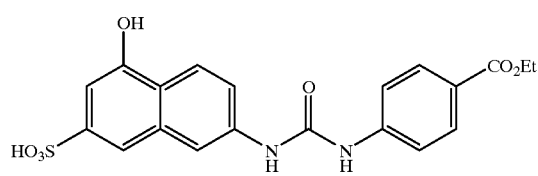
28

TABLE 1-continued
NOVEL COMPOUNDS
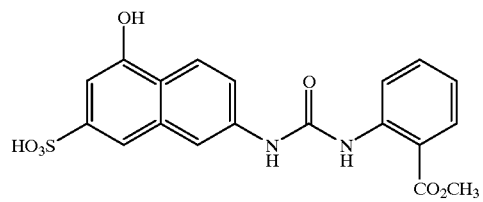
29
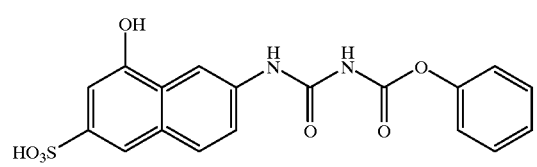
30
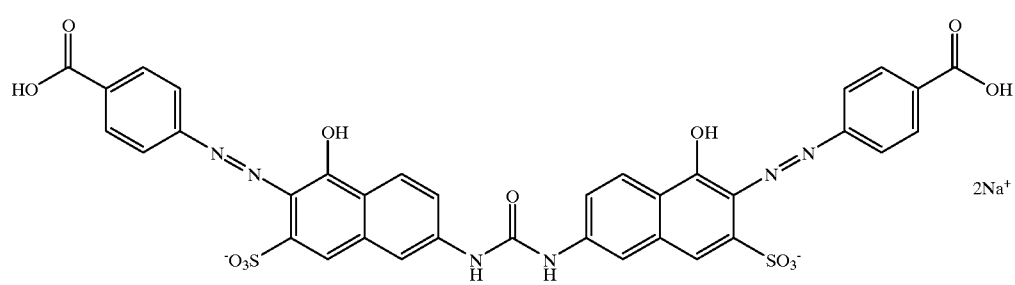
31
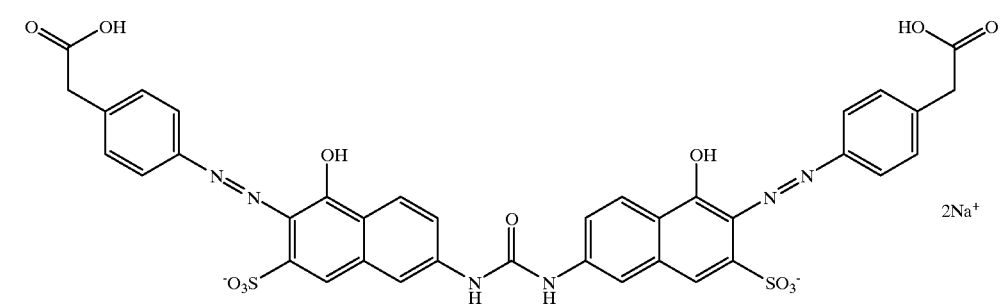
32
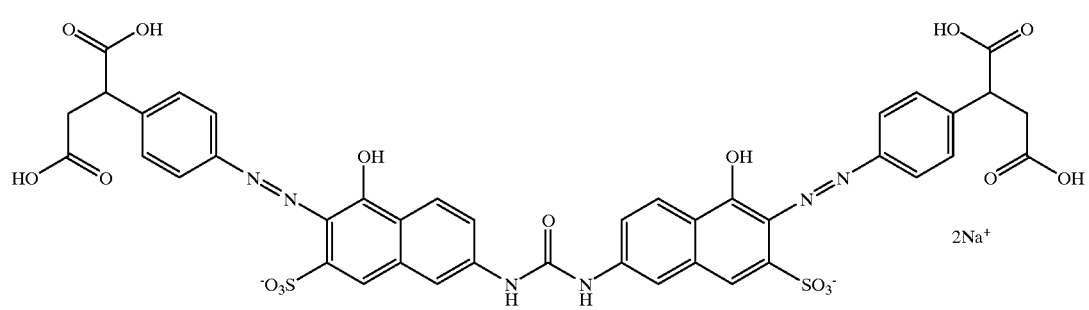
33
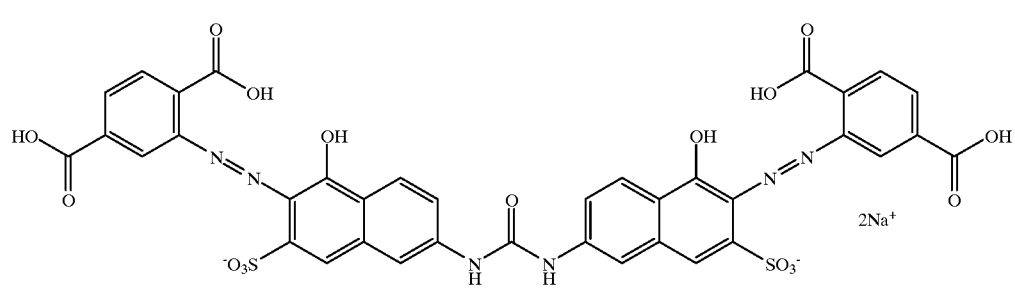
35

TABLE 1-continued
NOVEL COMPOUNDS
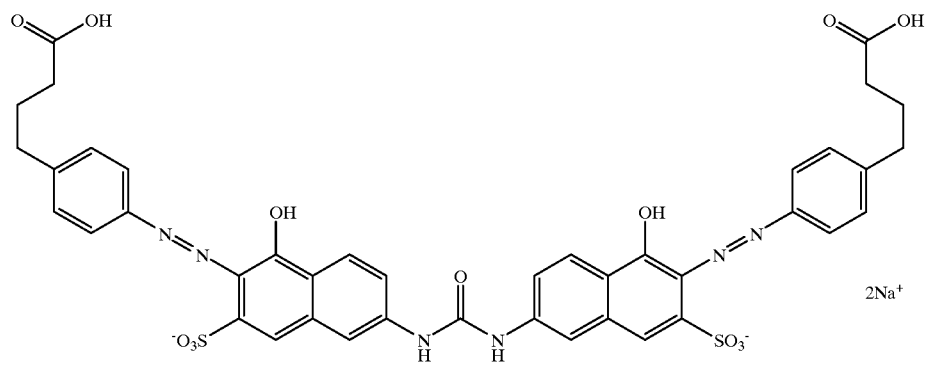
36
2Na⁺
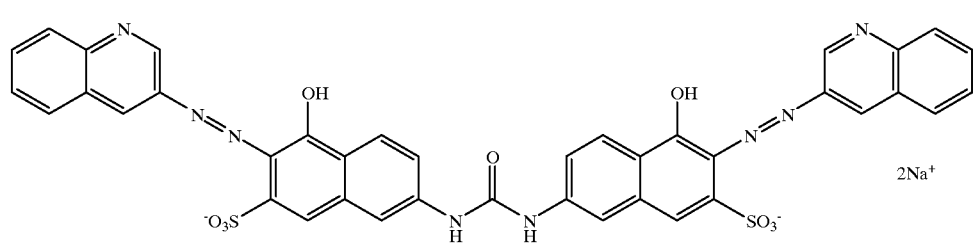
37
2Na⁺
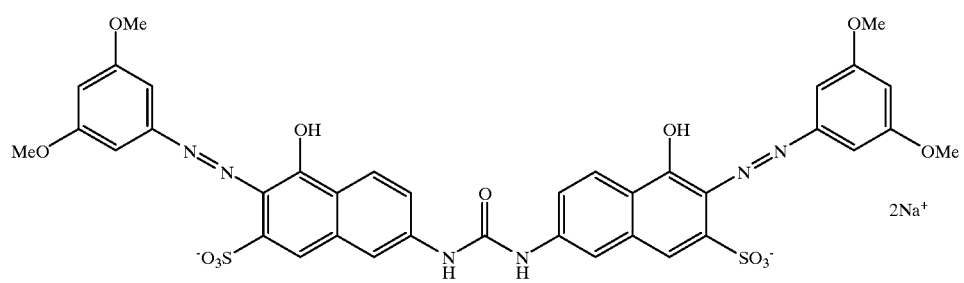
38
2Na⁺
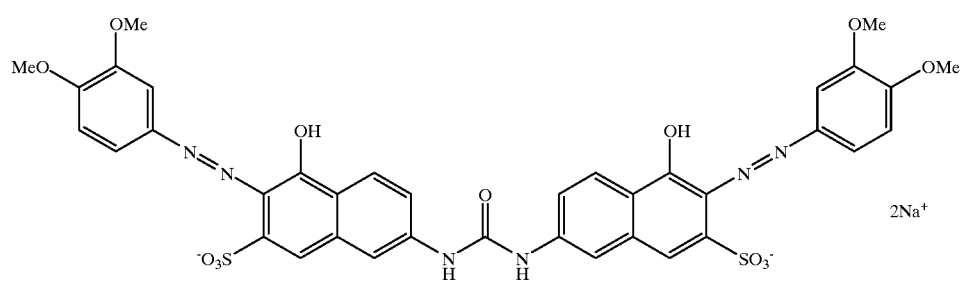
39
2Na⁺
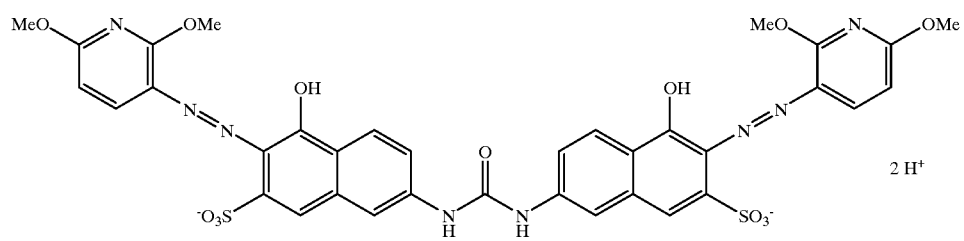
40
2 H⁺

TABLE 1-continued
NOVEL COMPOUNDS
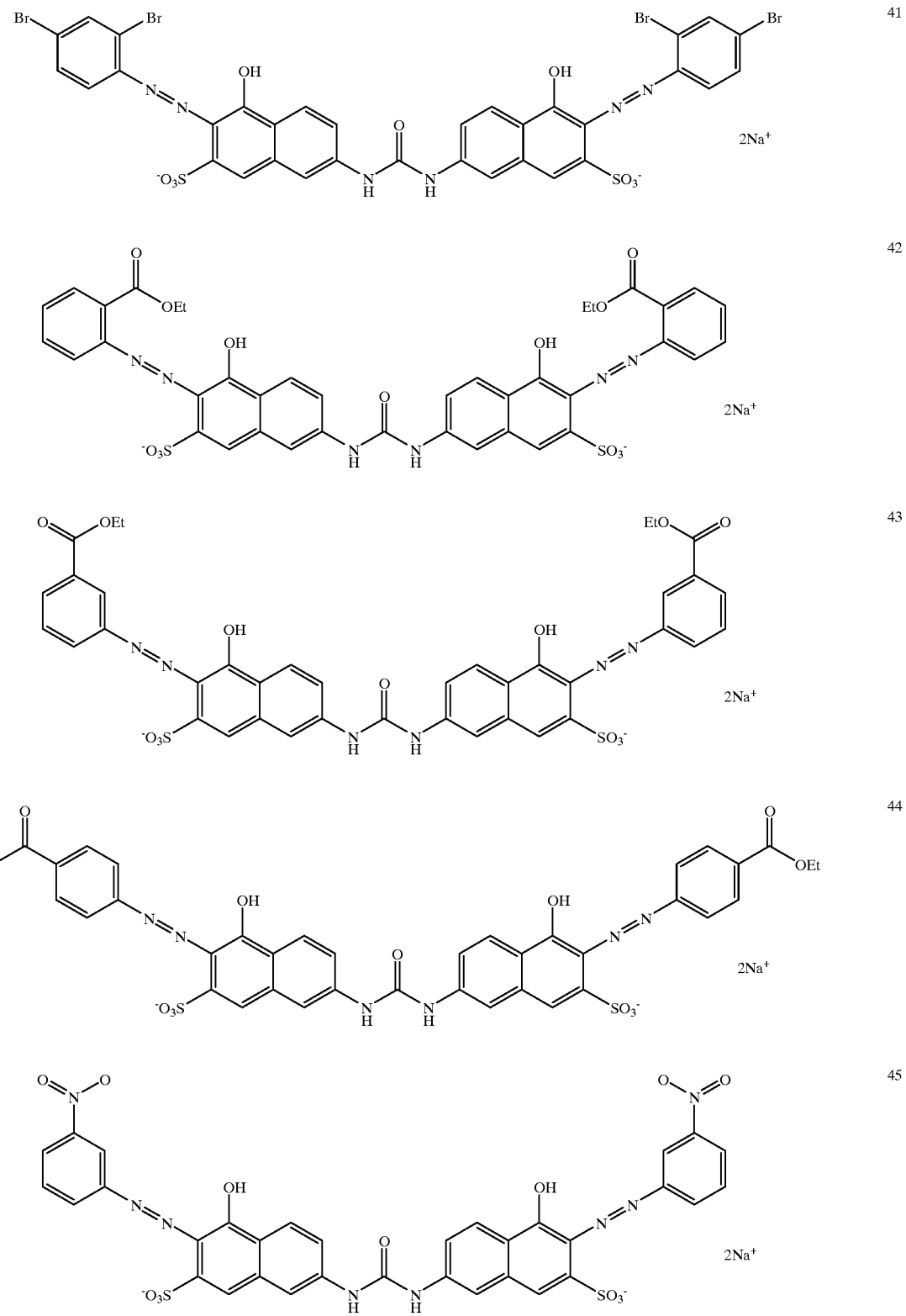

TABLE 1-continued

NOVEL COMPOUNDS

46

47

48

49

50

2Na⁺ (for each compound)

TABLE 1-continued
NOVEL COMPOUNDS
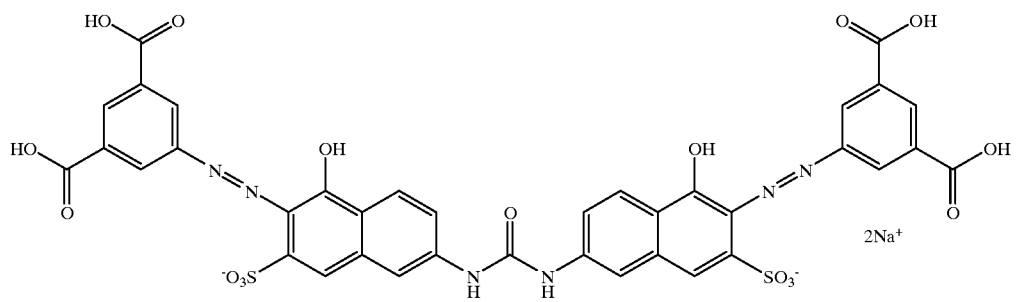 51 2Na+
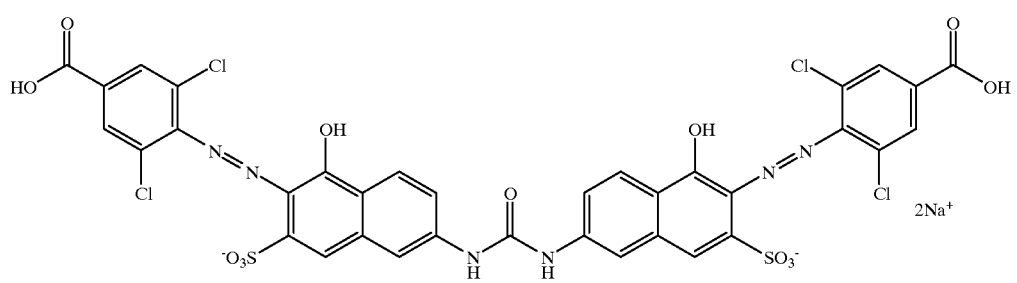 52 2Na+
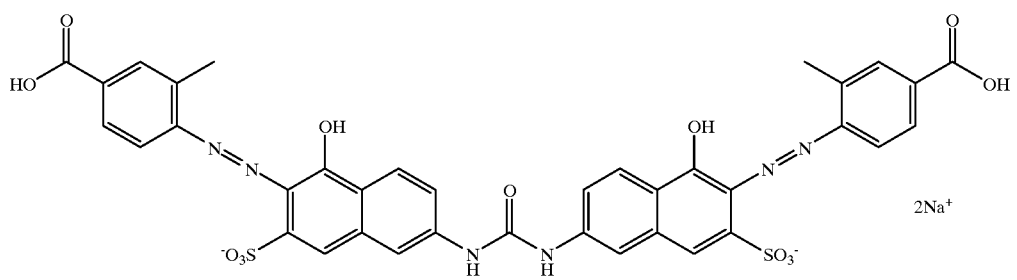 53 2Na+
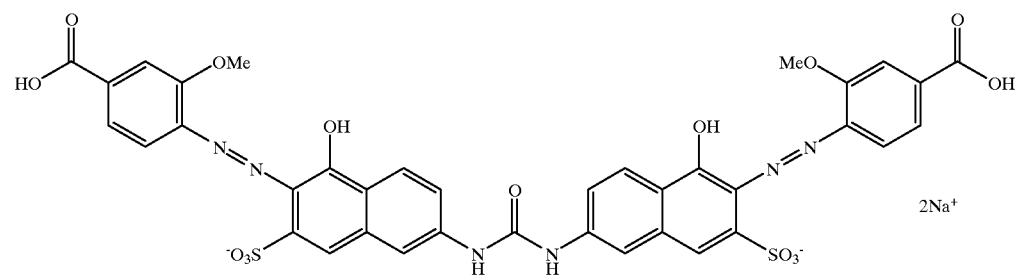 54 2Na+
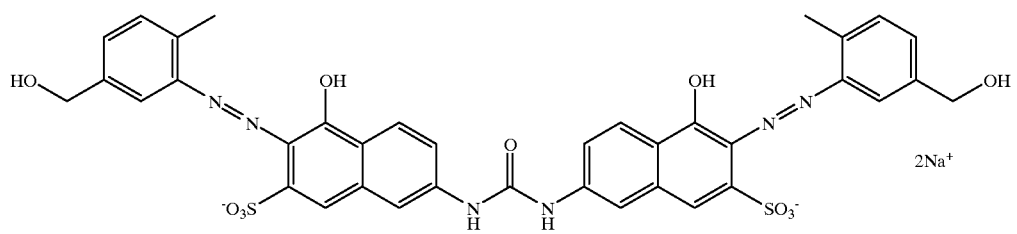 55 2Na+

TABLE 1-continued
NOVEL COMPOUNDS
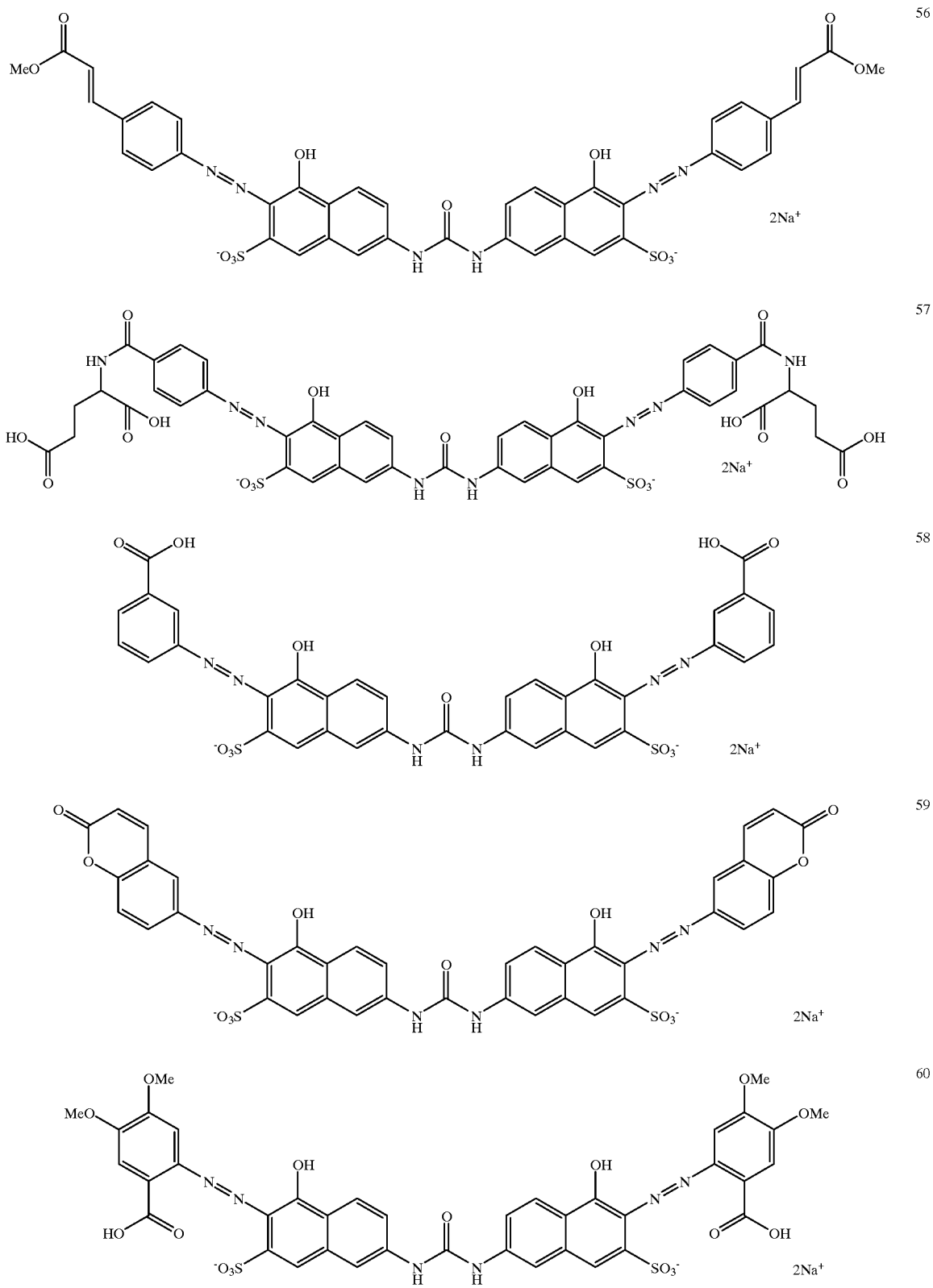

TABLE 1-continued
NOVEL COMPOUNDS
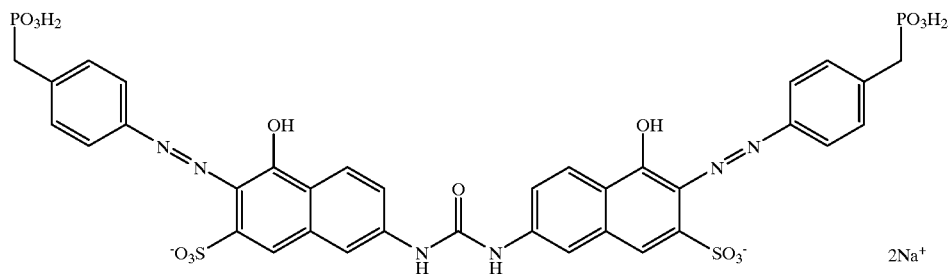
61
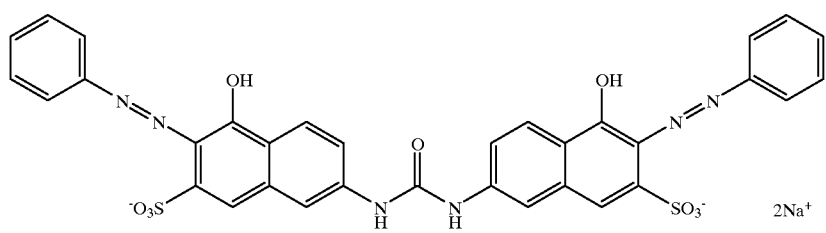
62
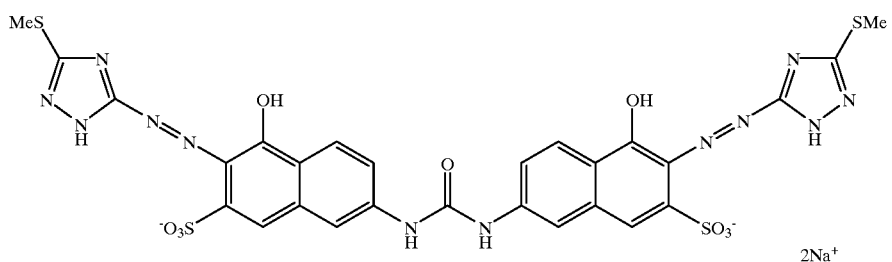
63
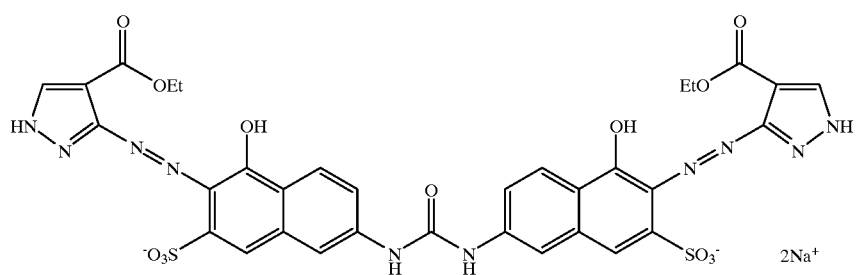
64
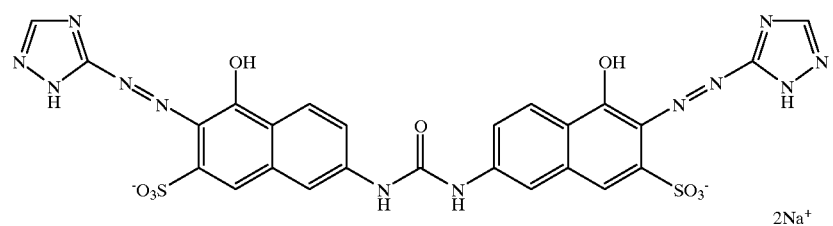
65

TABLE 1-continued

NOVEL COMPOUNDS

| No. | Structure |
|---|---|
| 66 | Bis[3-(3,4,5-trimethoxyphenylazo)-4-hydroxy-7-ureido-naphthalene-2-sulfonate], 2Na+ |
| 67 | Bis[3-(4-carboxyphenylazo)-4-hydroxy-7-ureido-naphthalene-2-sulfonate], 2Na+ |
| 68 | Bis[3-(4-(2-carboxyethyl)phenylazo)-4-hydroxy-7-ureido-naphthalene-2-sulfonate], 2Na+ |
| 69 | Bis[3-(4-fluorophenylazo)-4-hydroxy-7-ureido-naphthalene-2-sulfonate], 2Na+ |
| 70 | Bis[3-(4-chlorophenylazo)-4-hydroxy-7-ureido-naphthalene-2-sulfonate], 2Na+ |

TABLE 1-continued
NOVEL COMPOUNDS
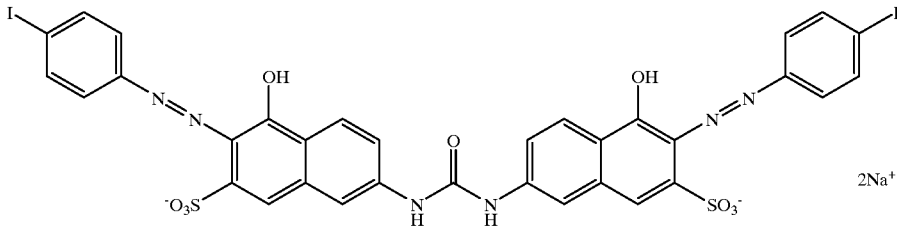 71  2Na⁺
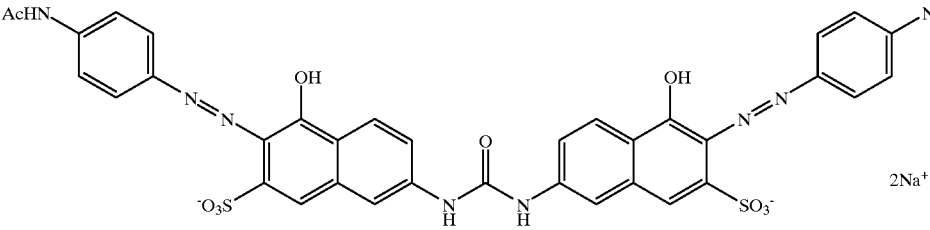 72  2Na⁺
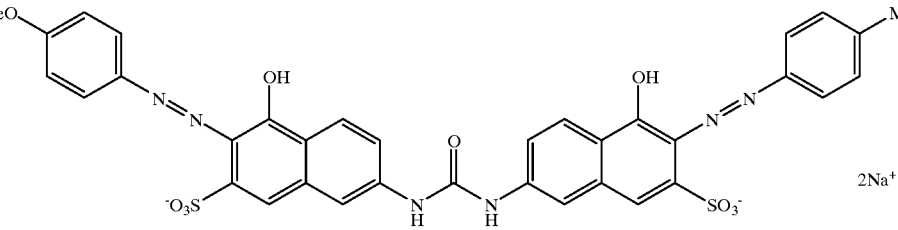 73  2Na⁺
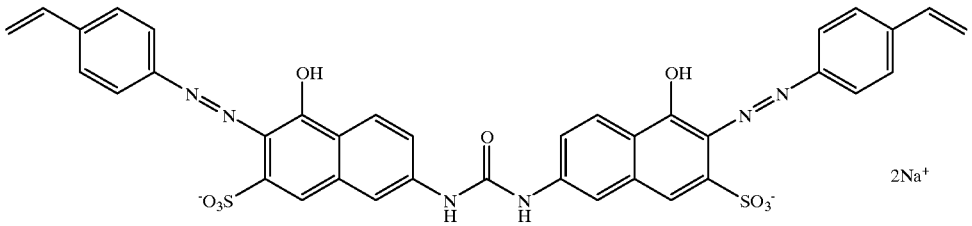 74  2Na⁺
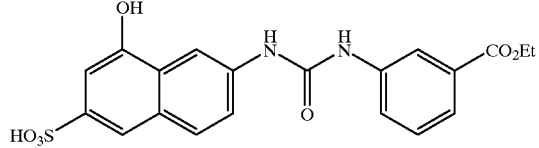 75
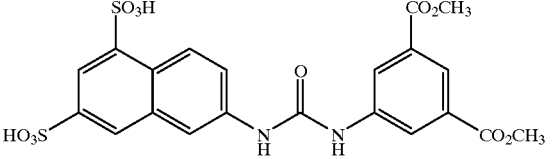 76
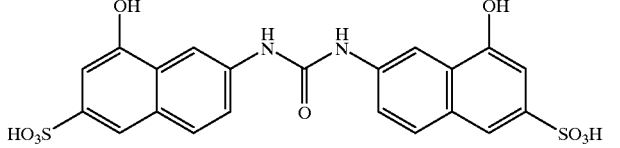 77

TABLE 1-continued

NOVEL COMPOUNDS

| | |
|---|---|
| (structure) | 78 |
| (structure) | 79 |
| (structure) | 80 |
| (structure) | 81 |
| (structure) | 82 |
| (structure) | 83 |
| (structure) | 84 |

TABLE 1-continued
NOVEL COMPOUNDS
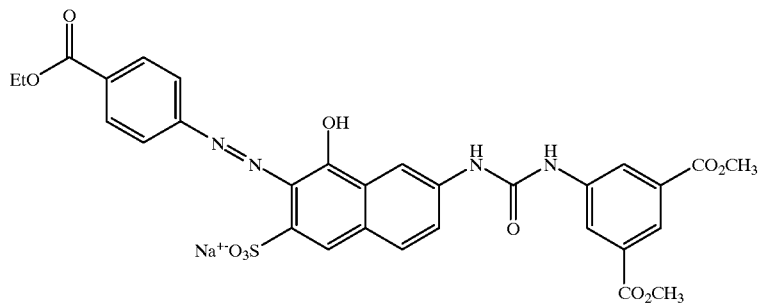
85
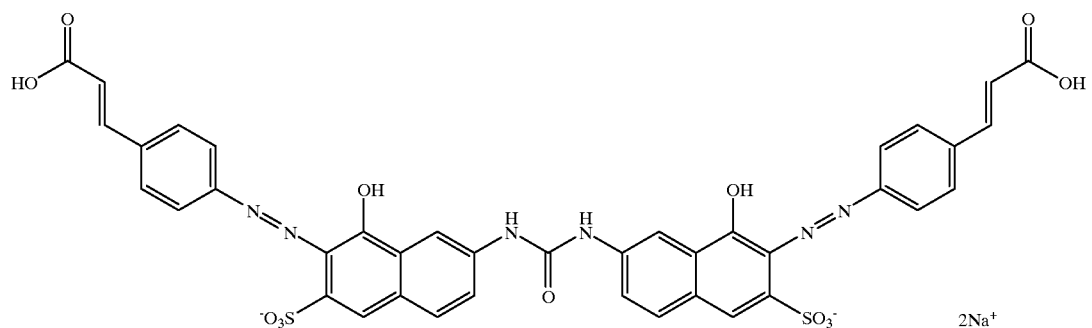
86
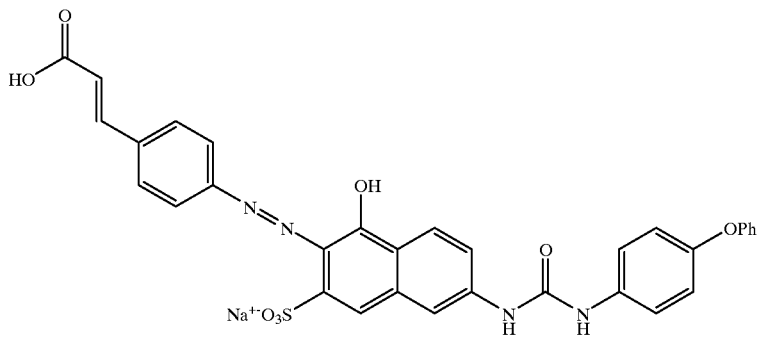
87
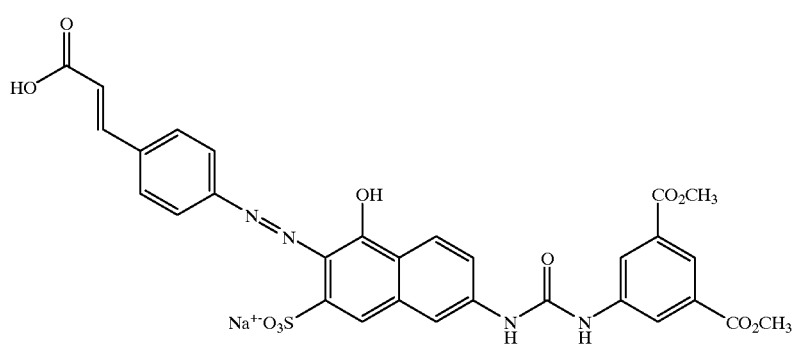
88

TABLE 1-continued
NOVEL COMPOUNDS
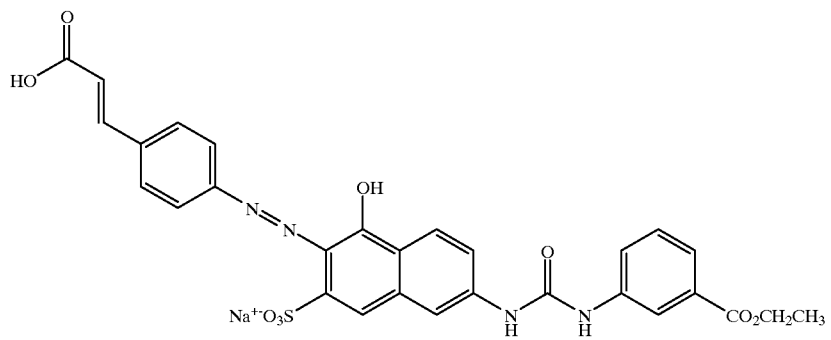
89
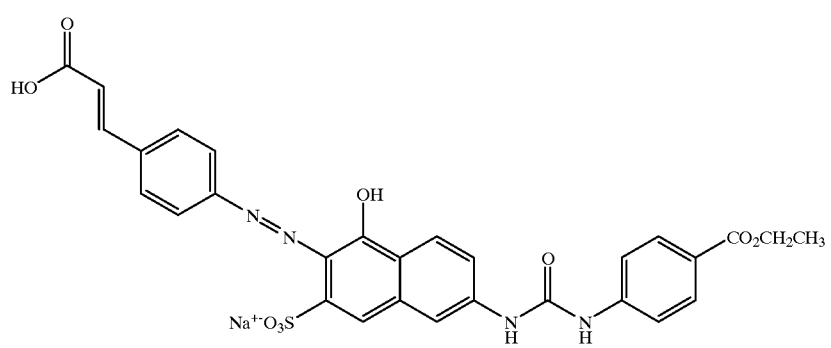
90
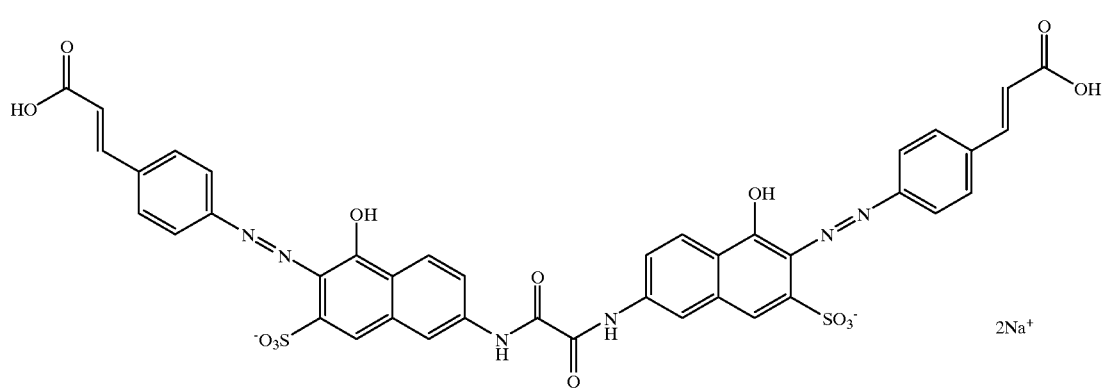
91
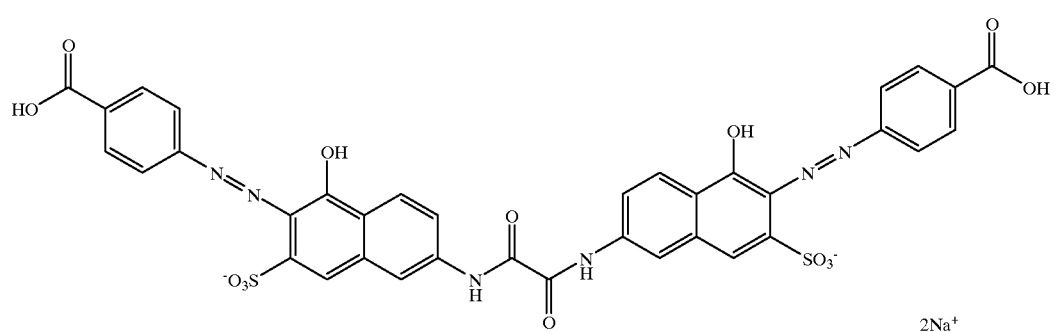
92

TABLE 1-continued
NOVEL COMPOUNDS
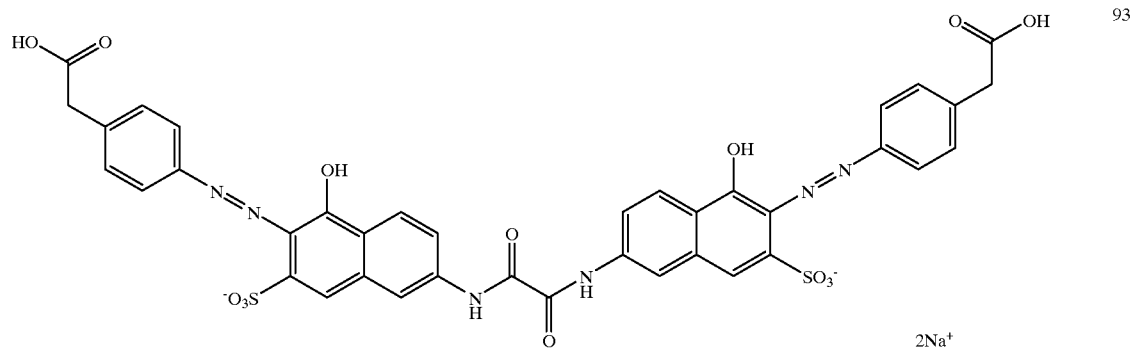
93
2Na+
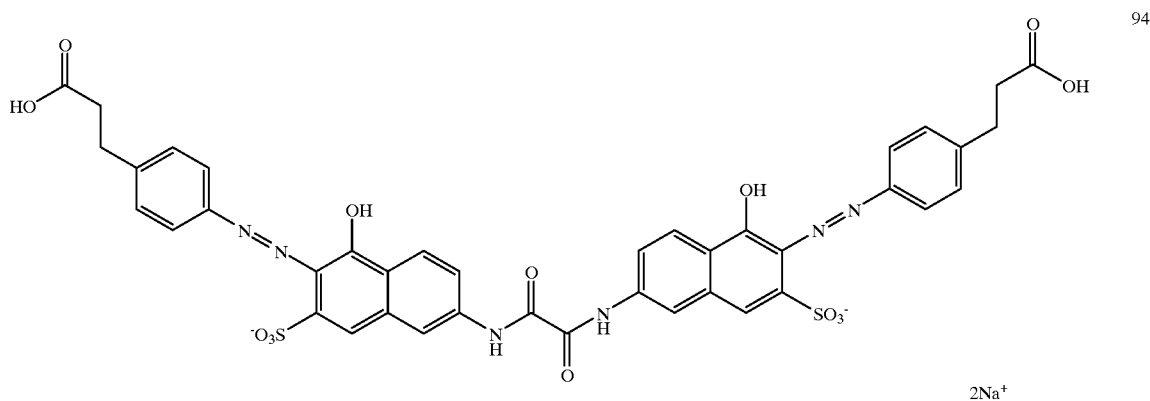
94
2Na+
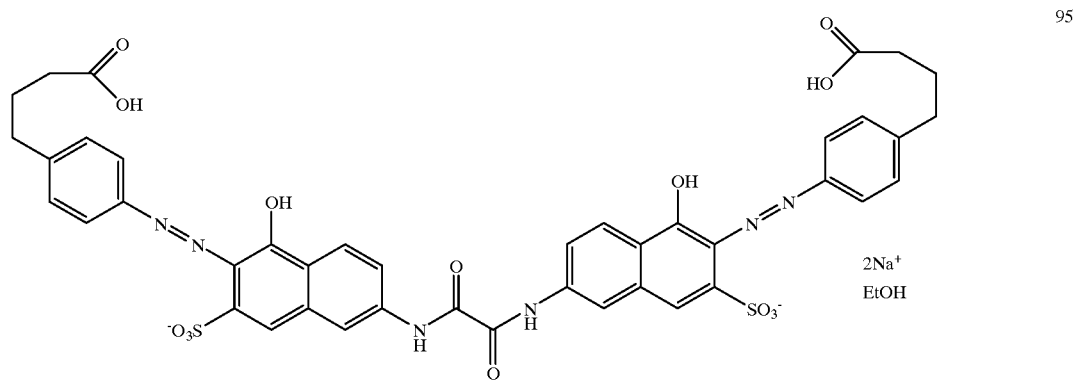
95
2Na+
EtOH
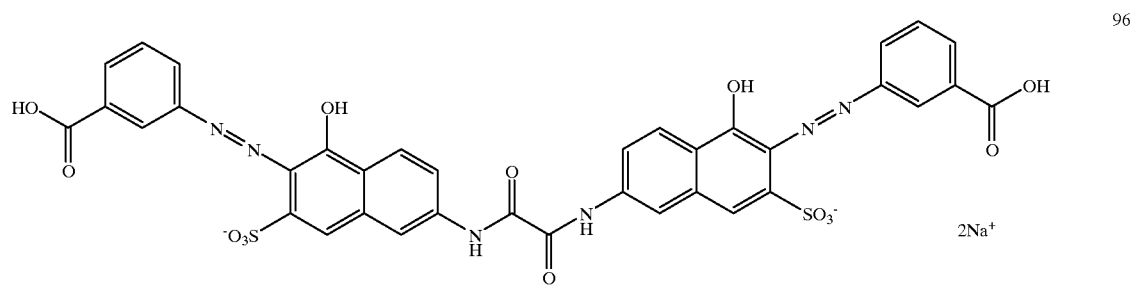
96
2Na+

TABLE 1-continued
NOVEL COMPOUNDS
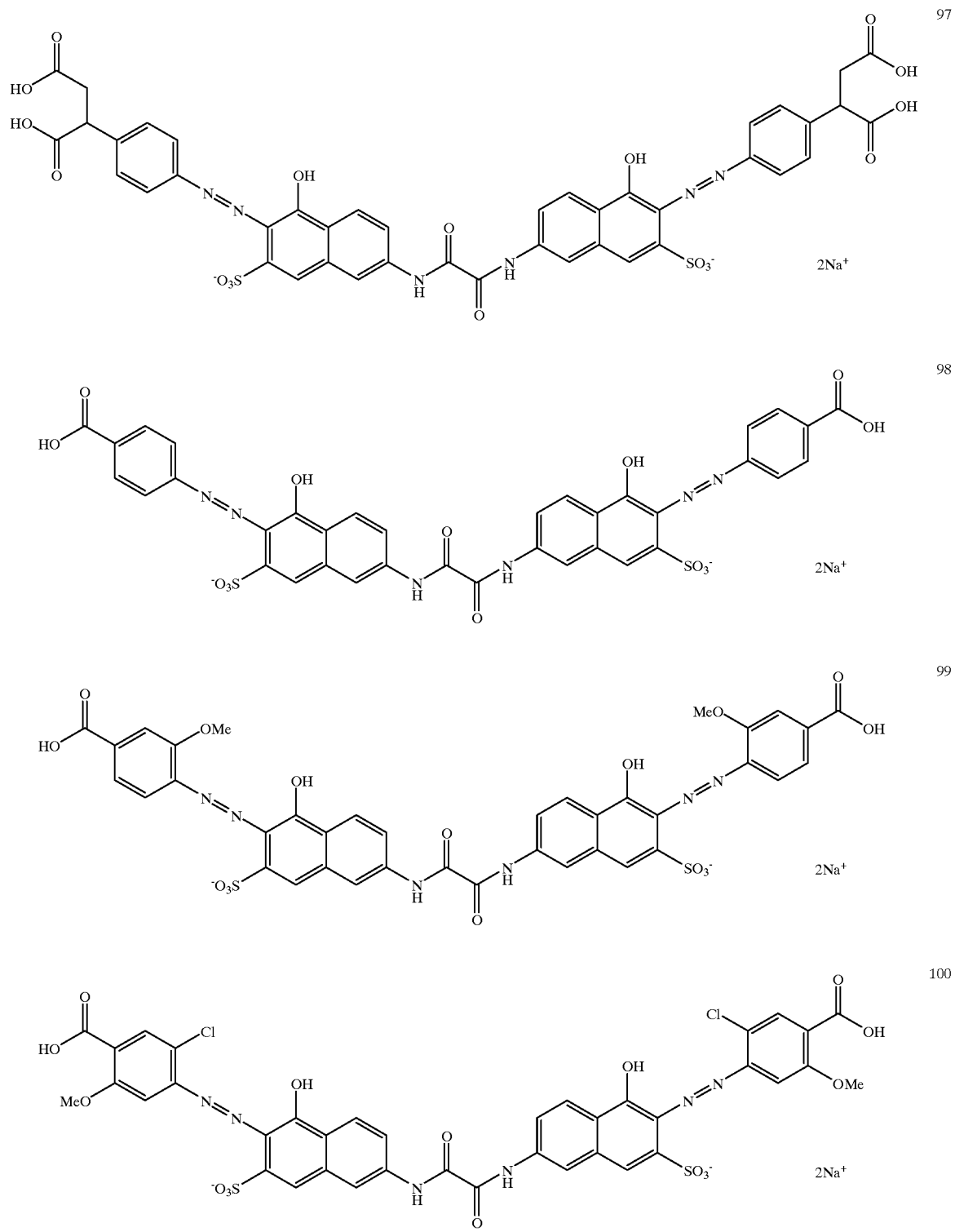

TABLE 1-continued
NOVEL COMPOUNDS
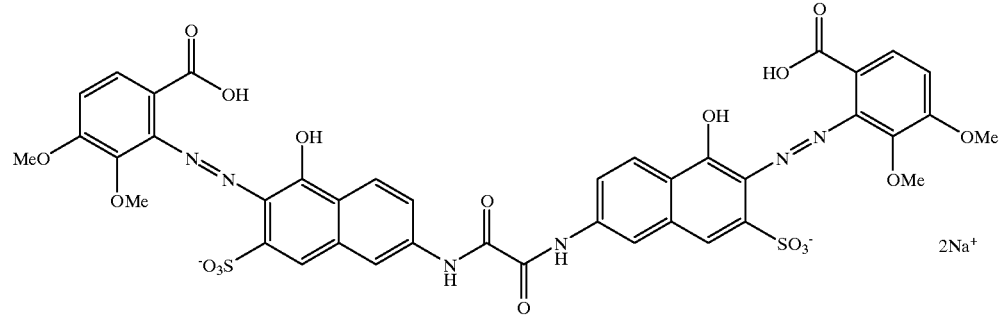
101 2Na+
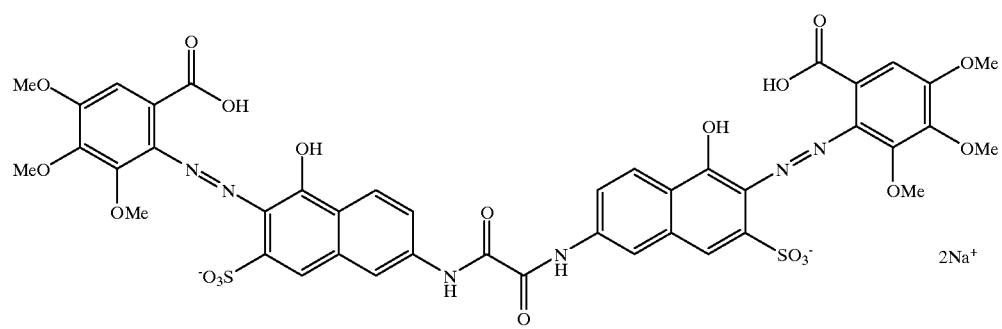
102 2Na+
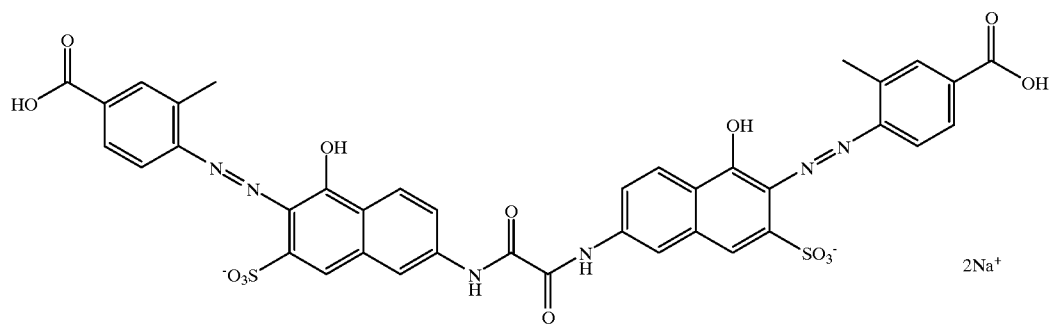
103 2Na+
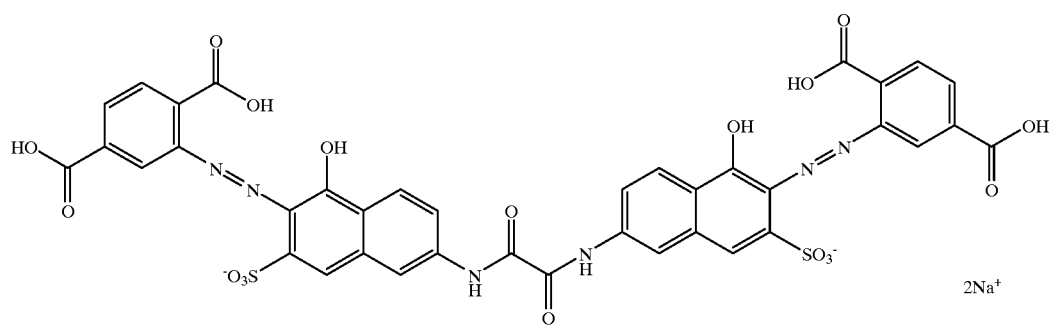
104 2Na+

TABLE 1-continued
NOVEL COMPOUNDS
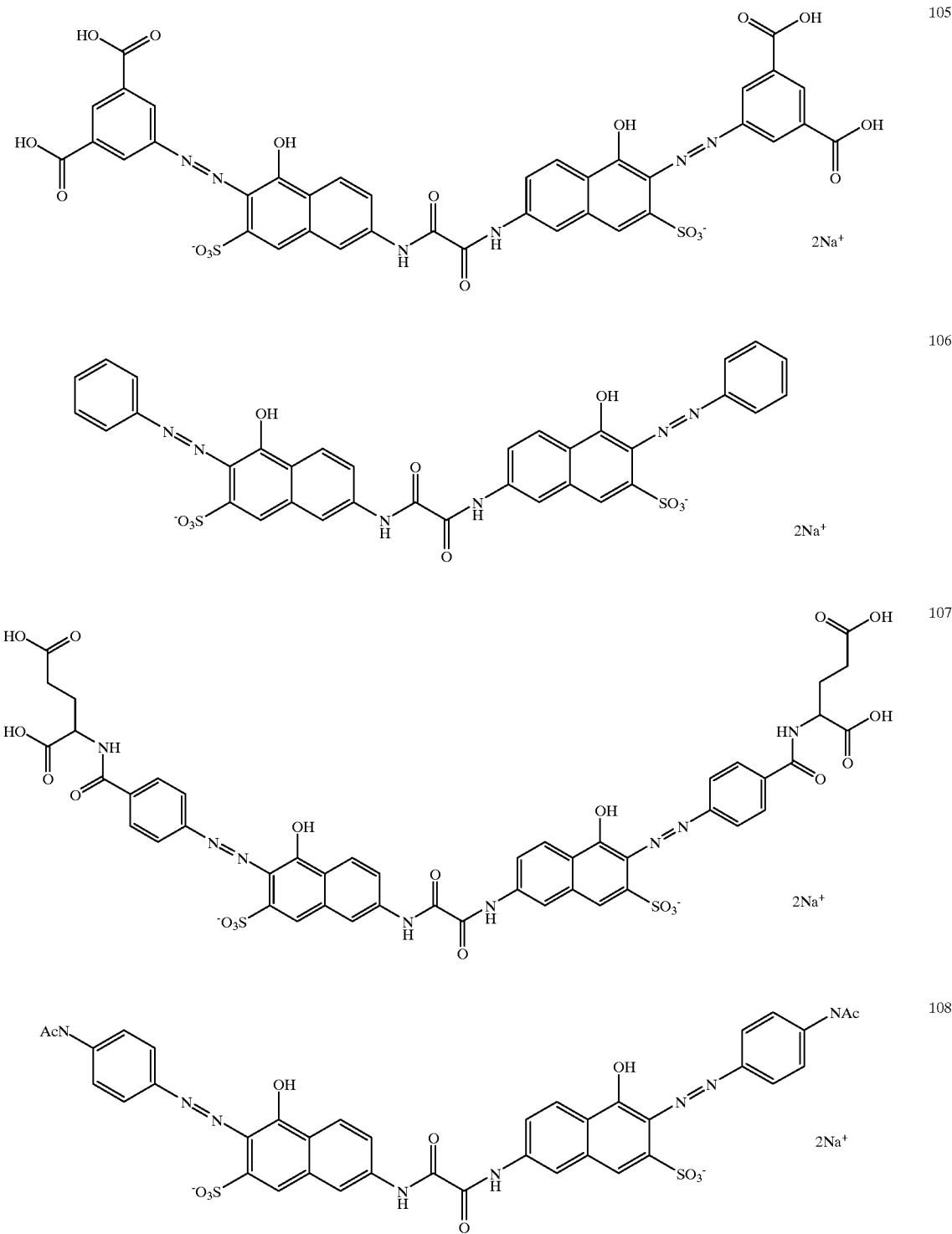

TABLE 1-continued
NOVEL COMPOUNDS
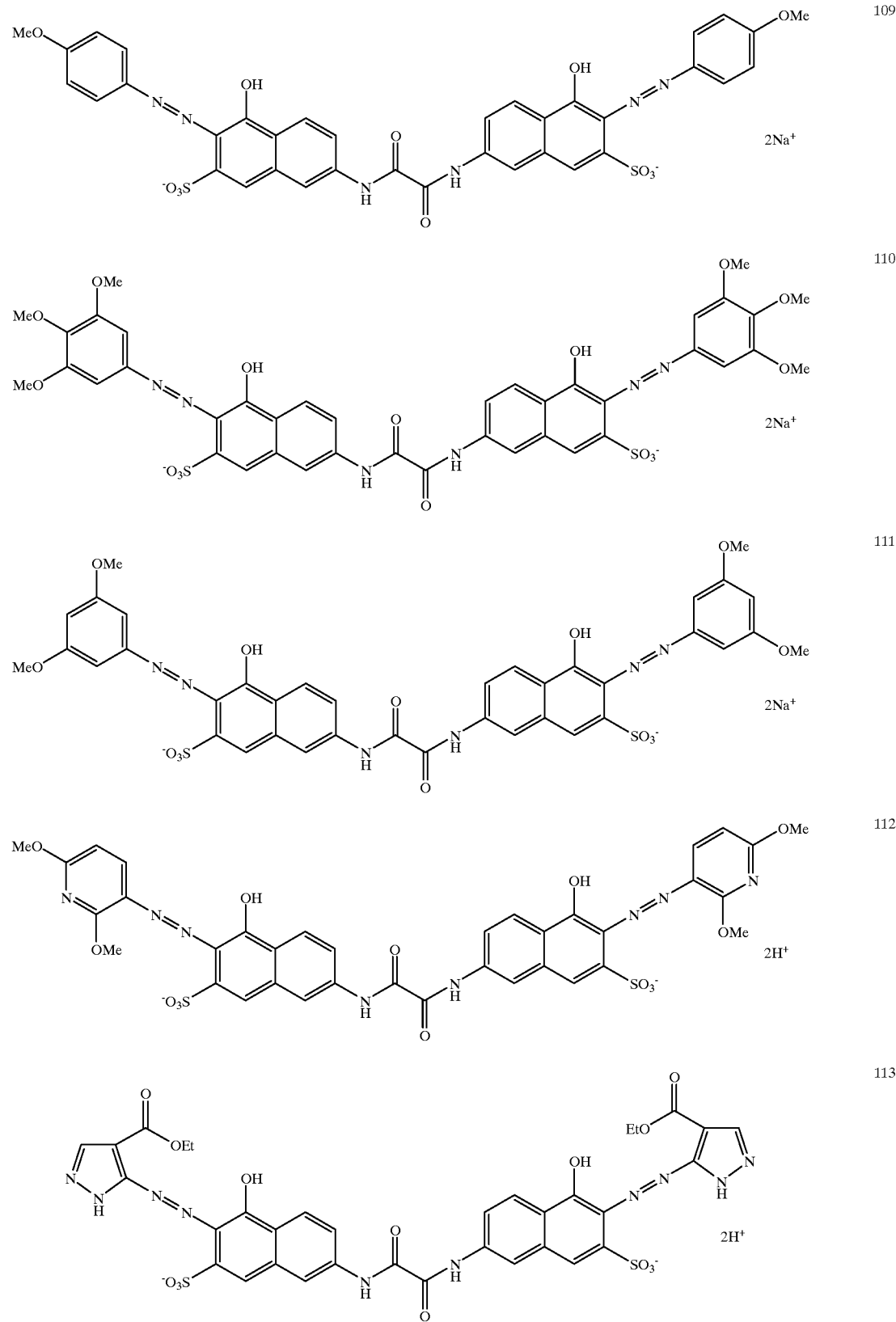

TABLE 1-continued
NOVEL COMPOUNDS
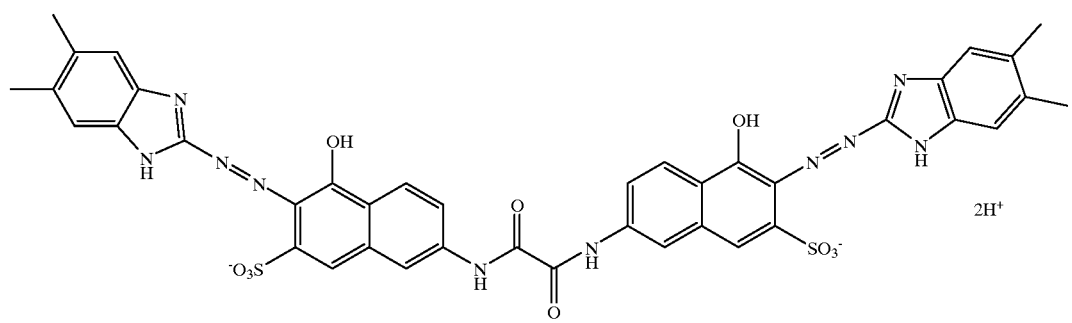 114
2H+
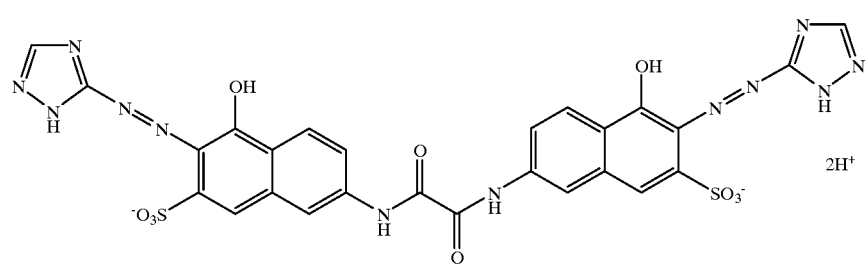 115
2H+
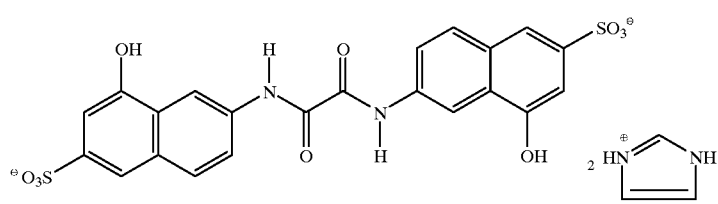 116
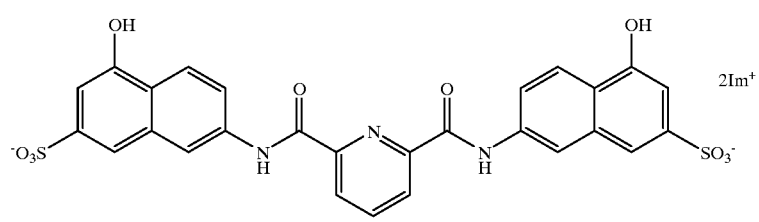 117
2Im+
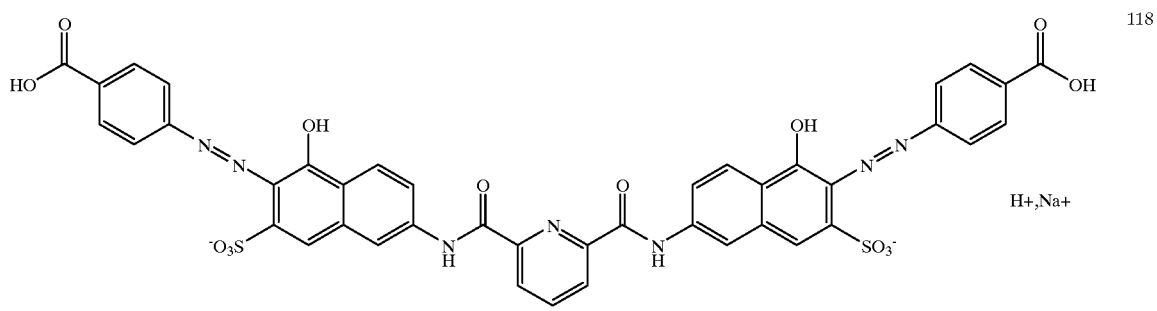 118
H+,Na+

TABLE 1-continued
NOVEL COMPOUNDS
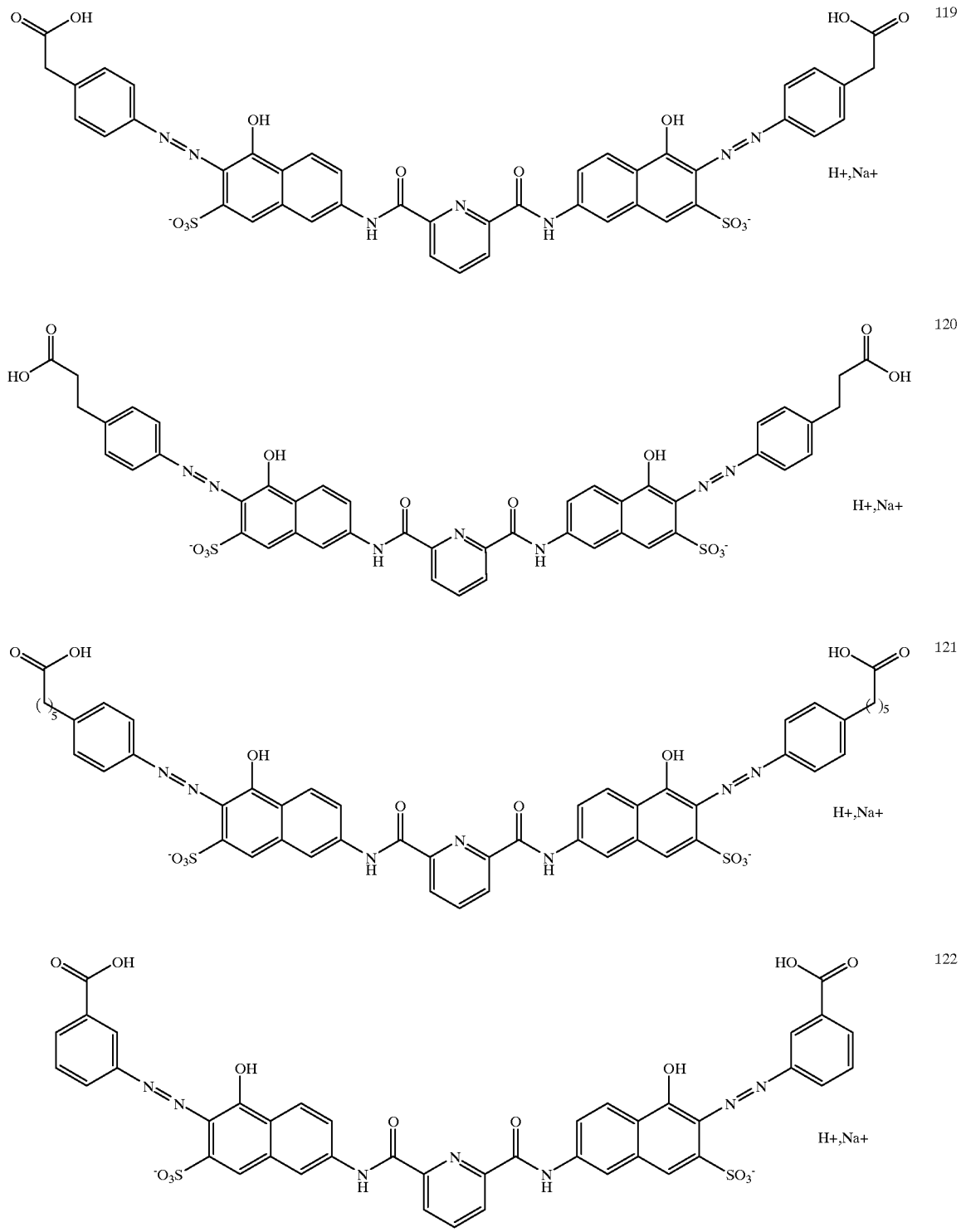

TABLE 1-continued
NOVEL COMPOUNDS
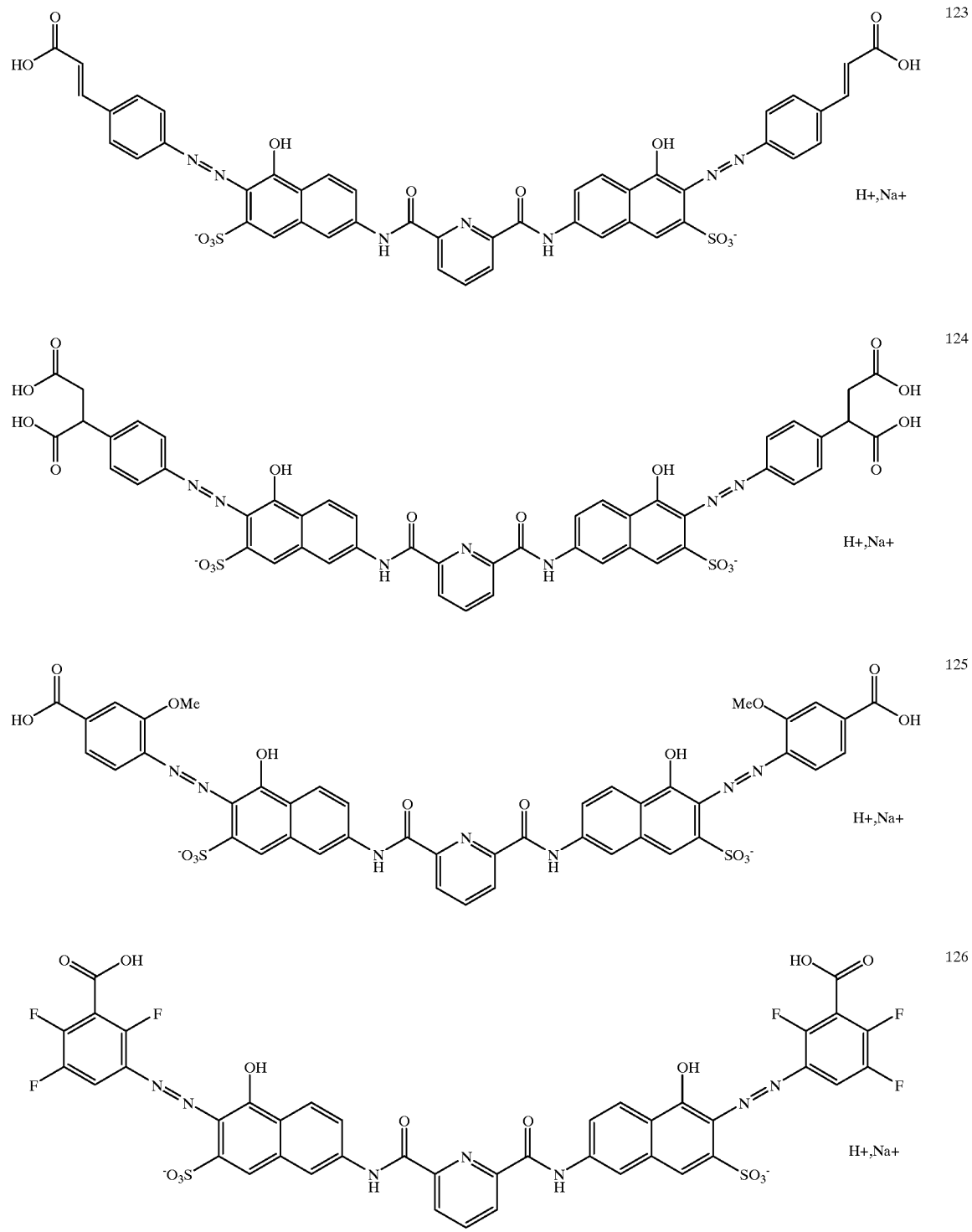

TABLE 1-continued
NOVEL COMPOUNDS
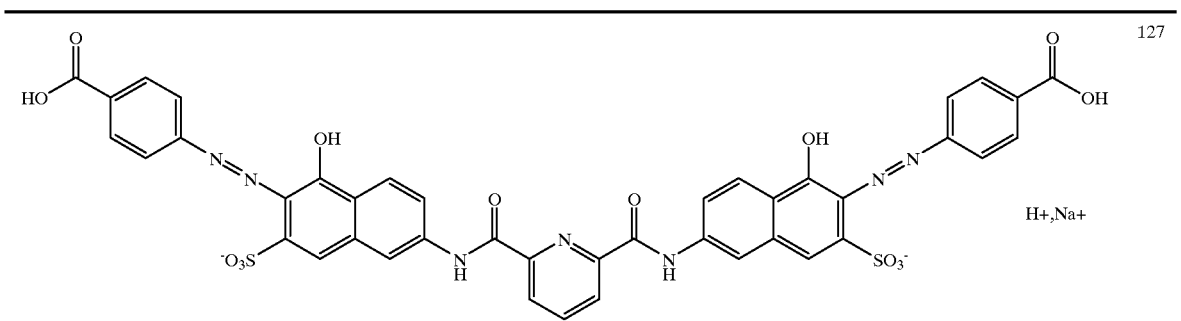
127
H+,Na+
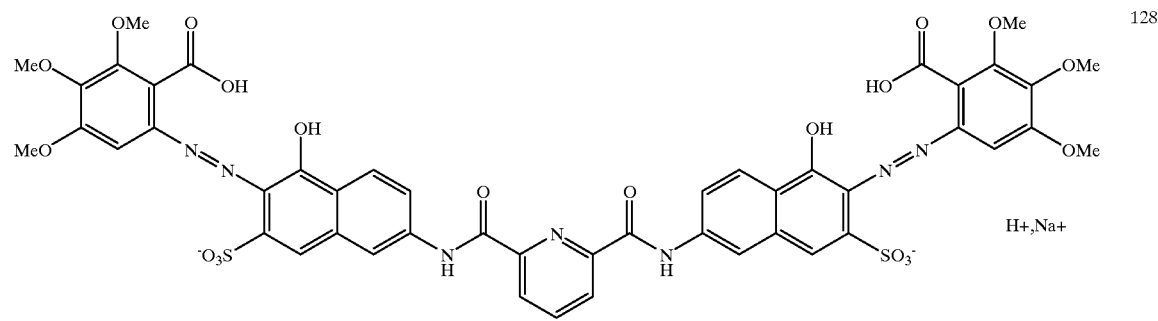
128
H+,Na+
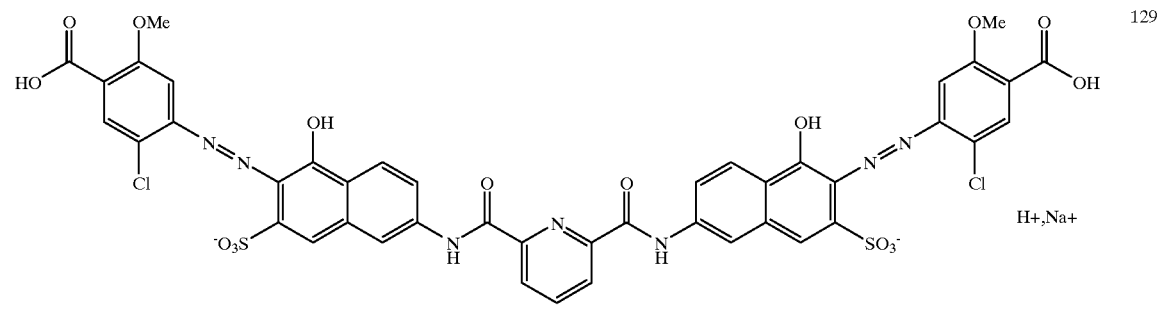
129
H+,Na+
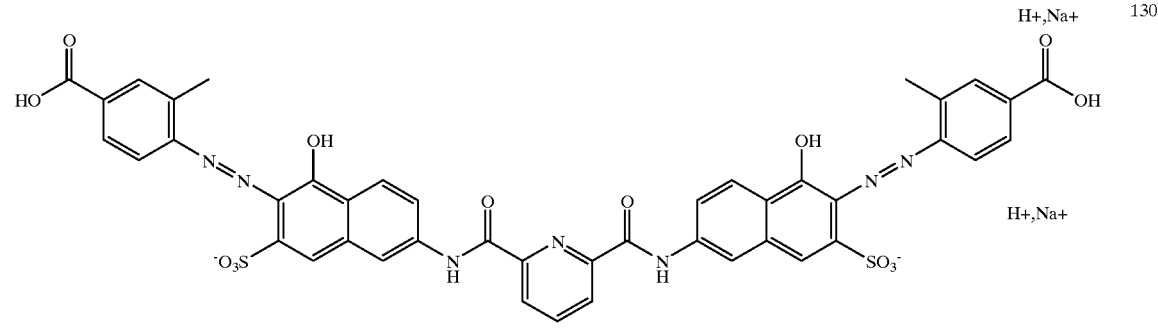
130
H+,Na+
H+,Na+
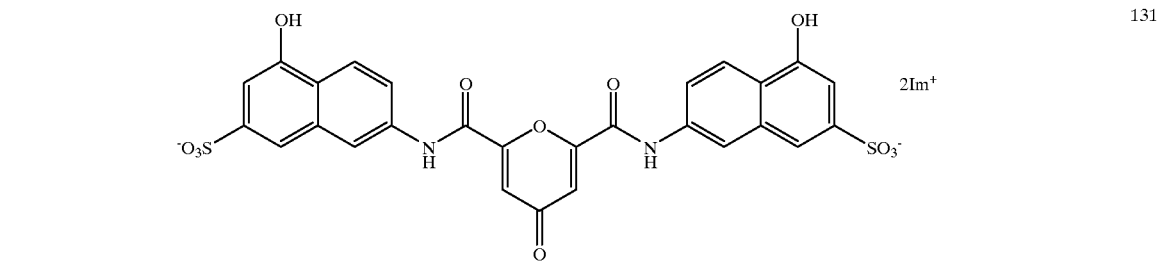
131
2Im+

TABLE 1-continued
NOVEL COMPOUNDS
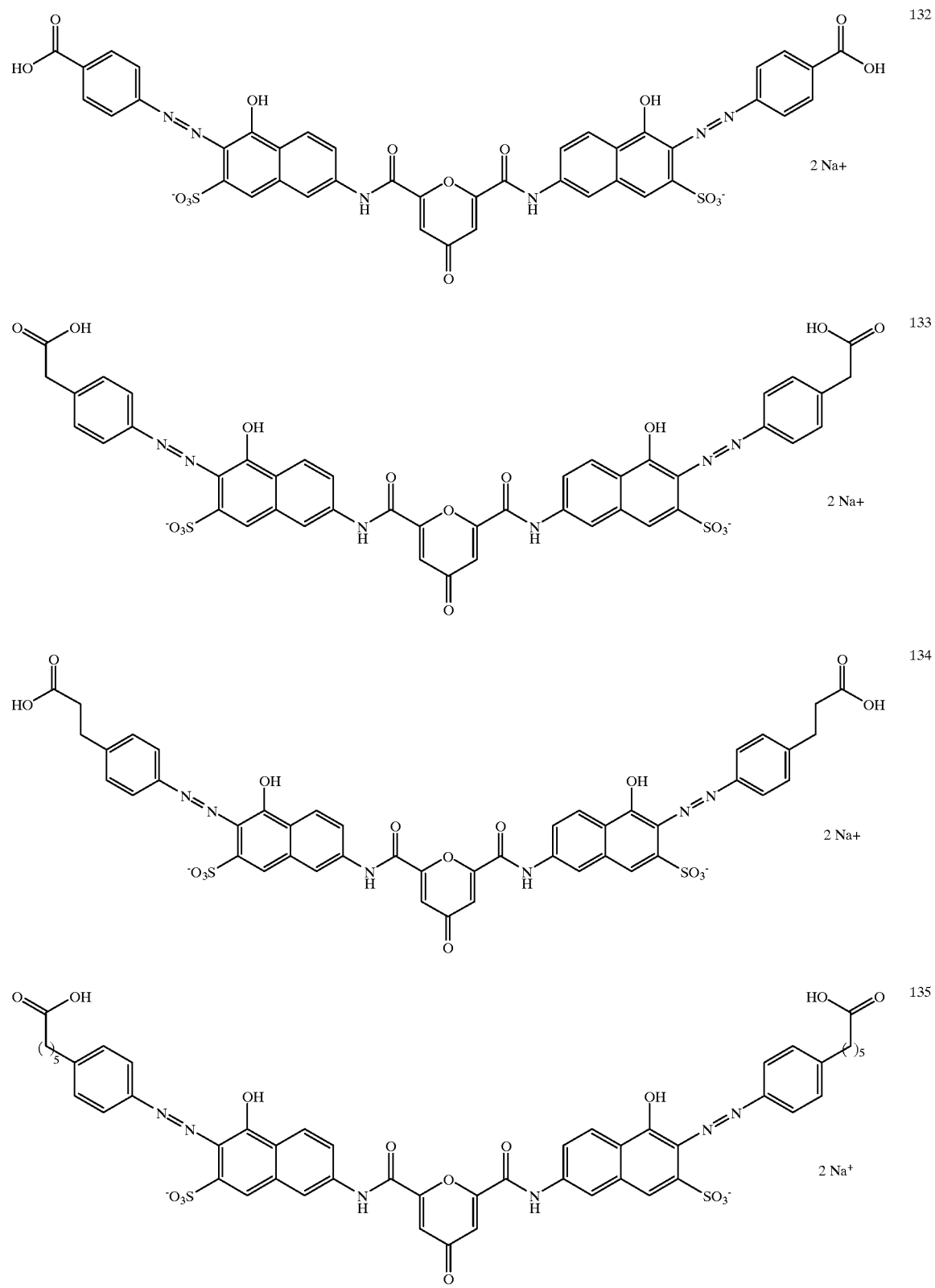

TABLE 1-continued
NOVEL COMPOUNDS
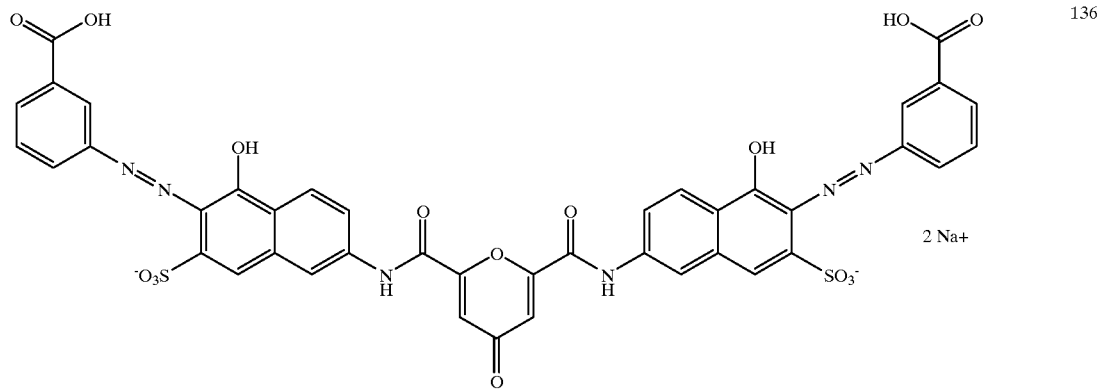
136
2 Na+
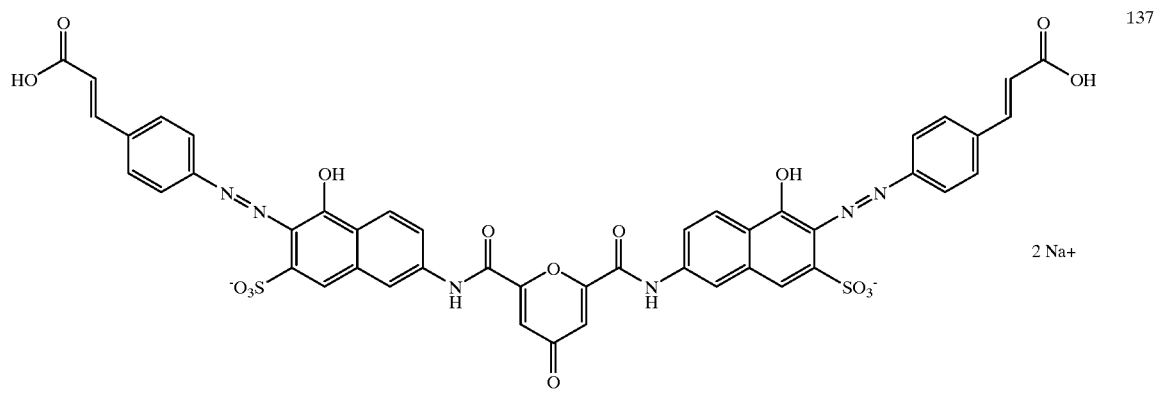
137
2 Na+
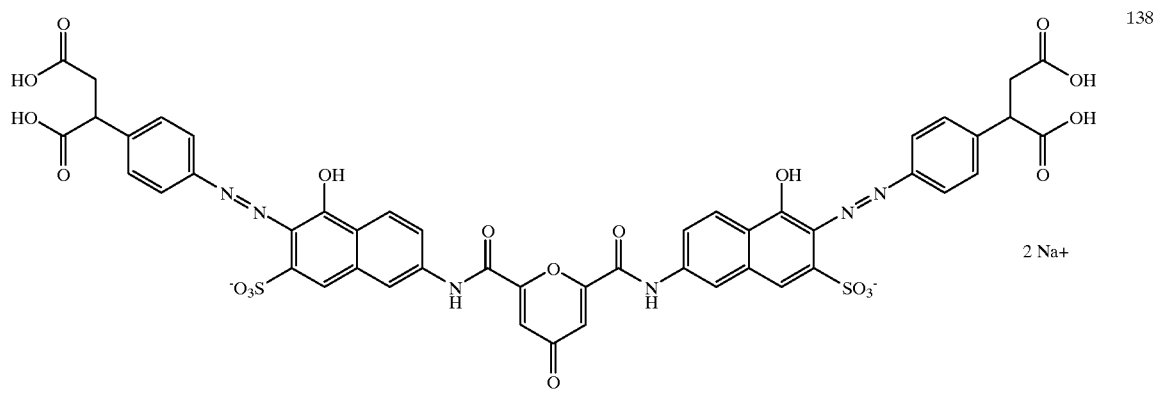
138
2 Na+
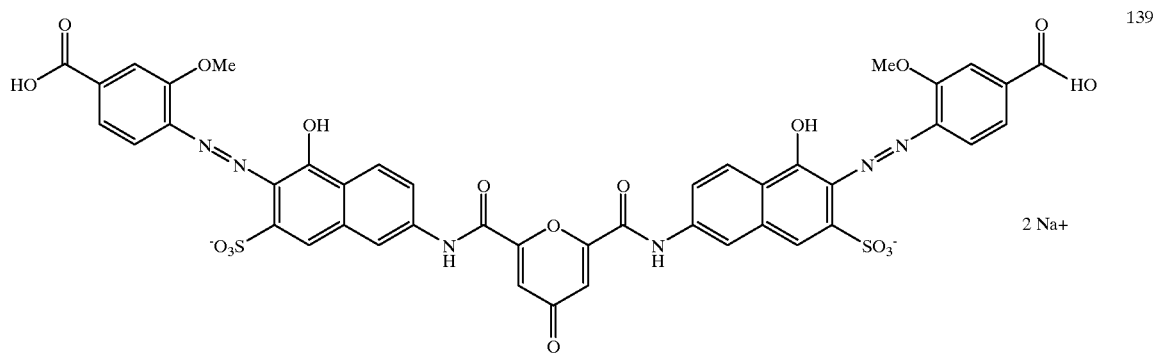
139
2 Na+

TABLE 1-continued
NOVEL COMPOUNDS
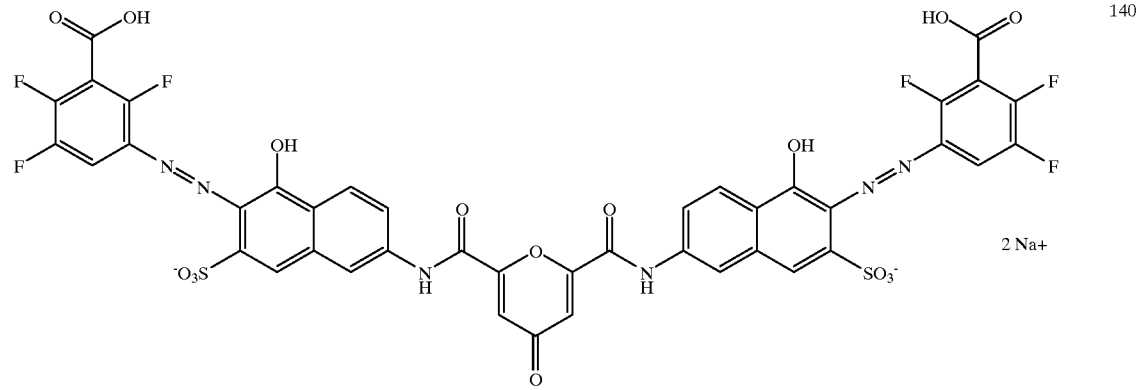
140
2 Na+
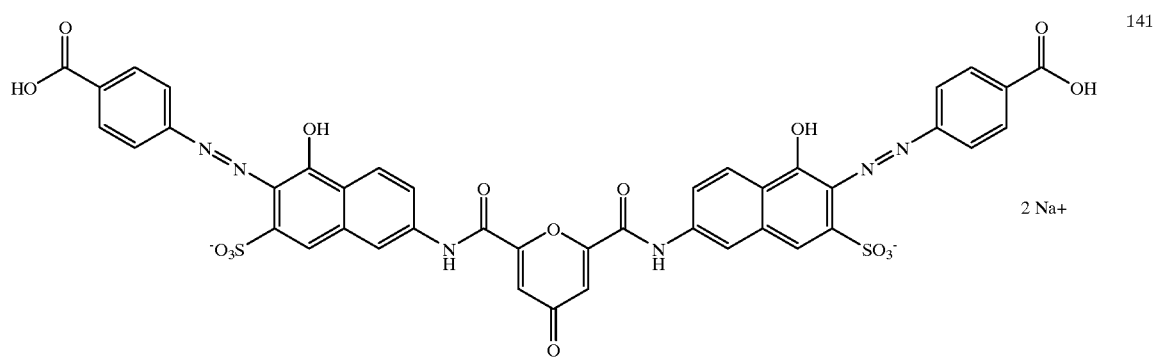
141
2 Na+
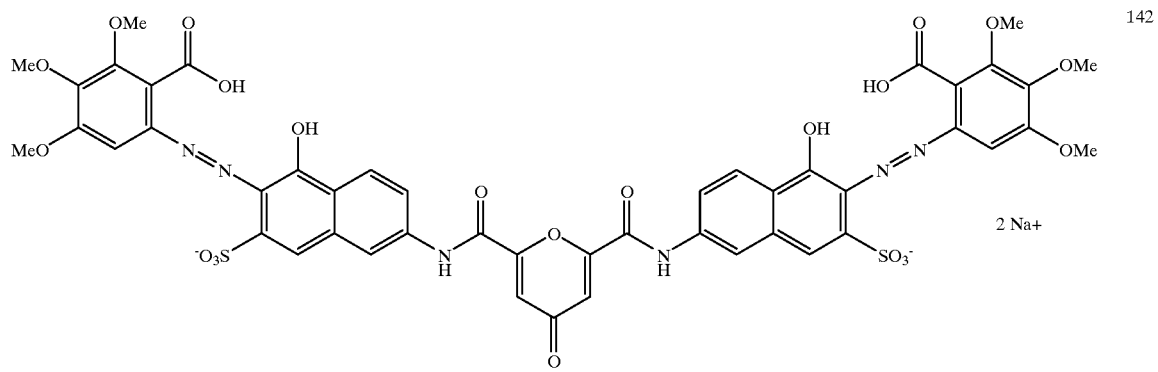
142
2 Na+
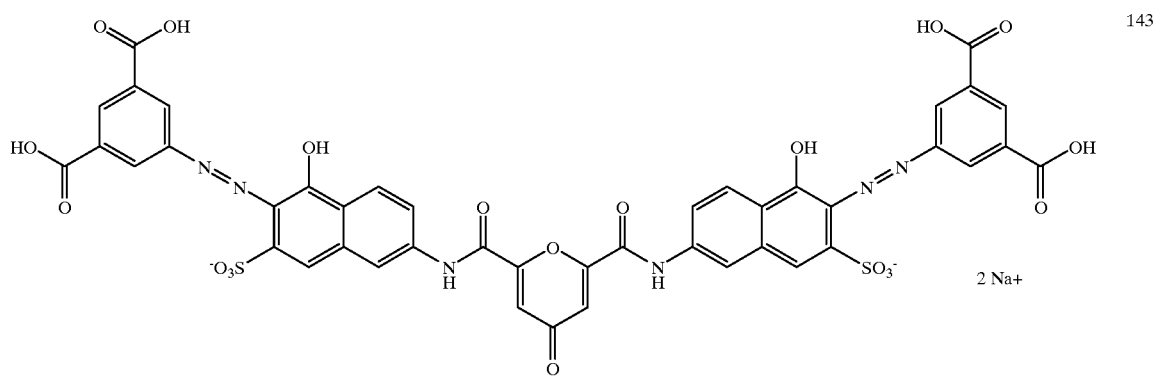
143
2 Na+

TABLE 1-continued
NOVEL COMPOUNDS
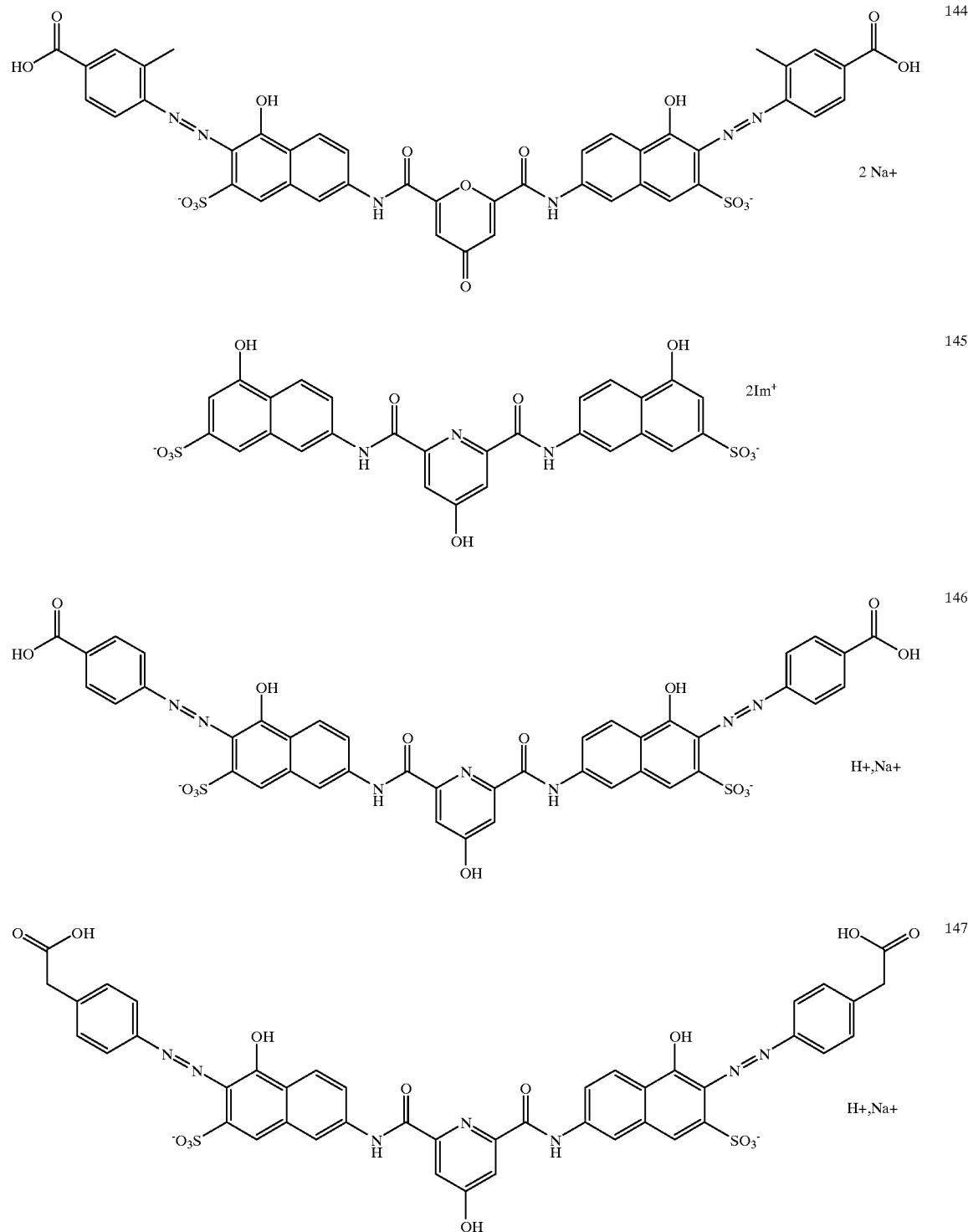

TABLE 1-continued
NOVEL COMPOUNDS
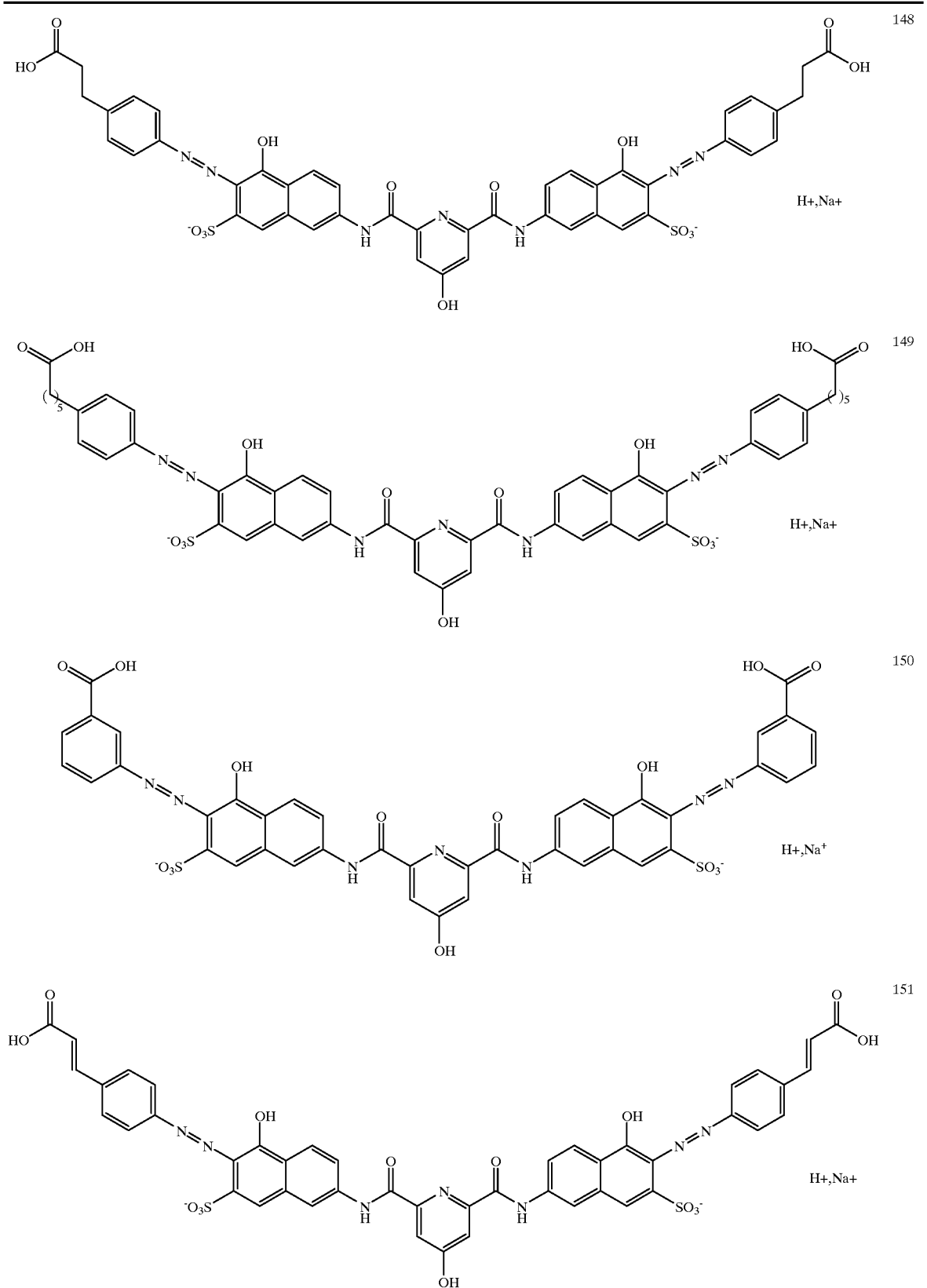

TABLE 1-continued
NOVEL COMPOUNDS
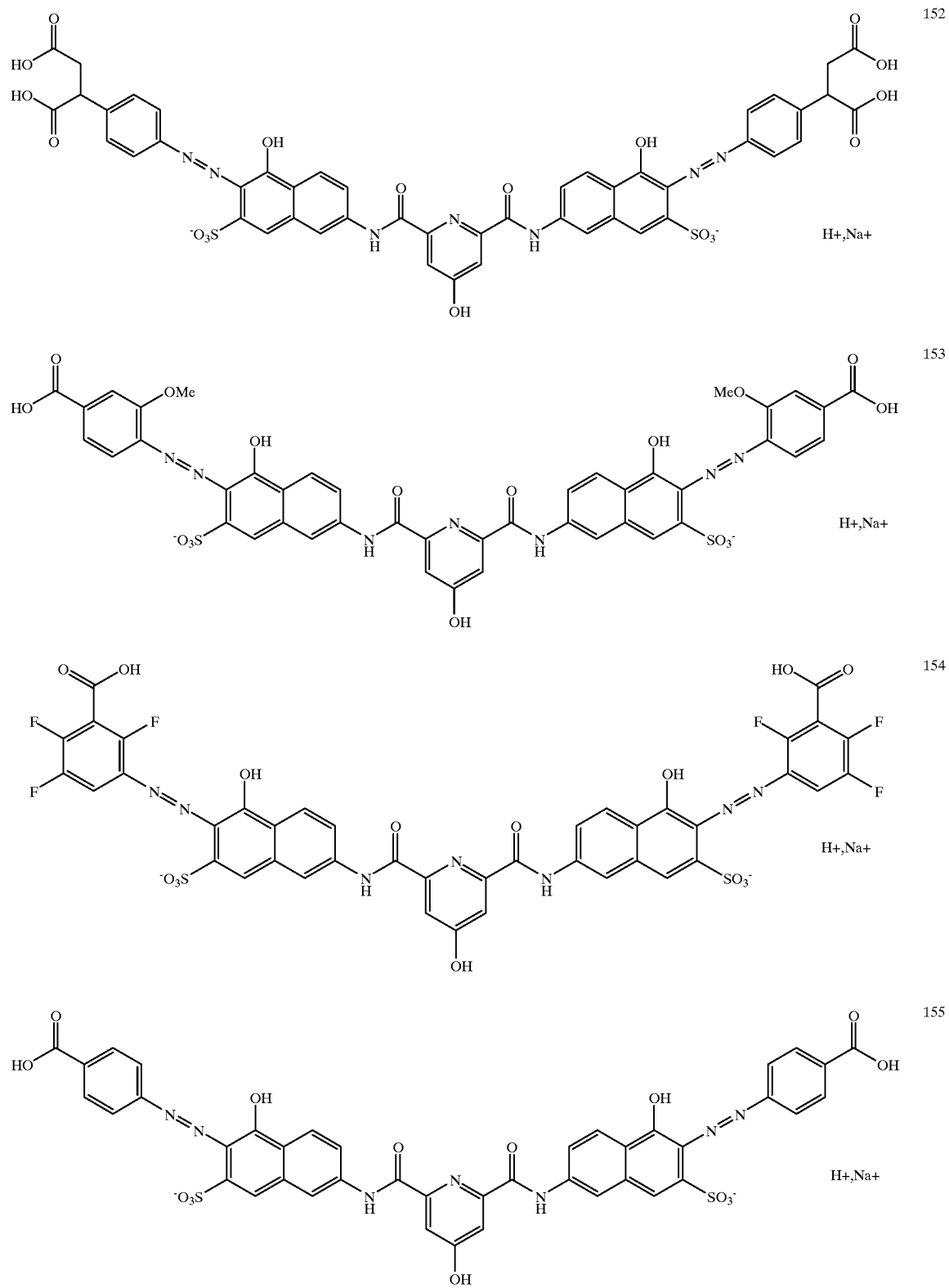

TABLE 1-continued
NOVEL COMPOUNDS
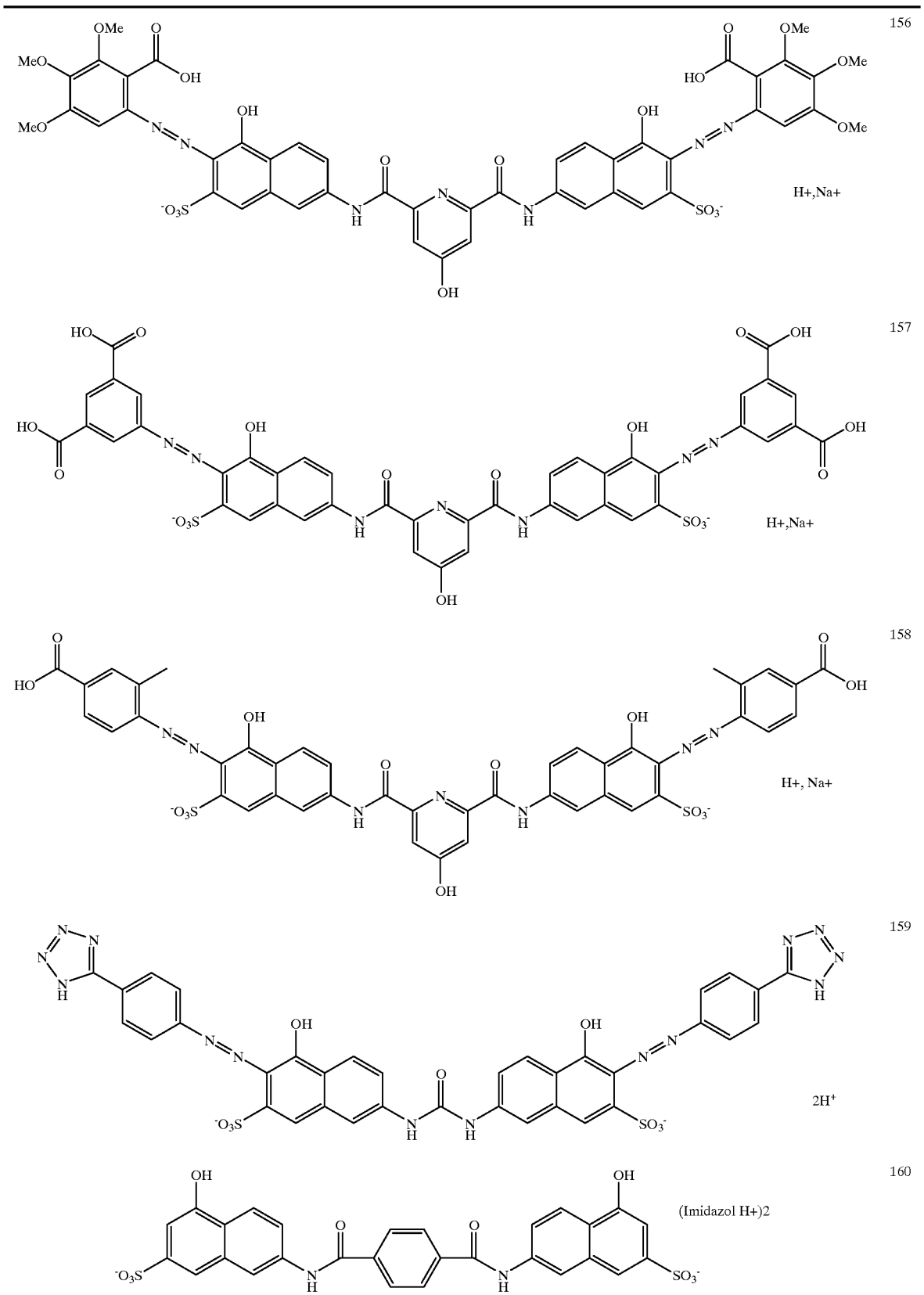

TABLE 1-continued
NOVEL COMPOUNDS
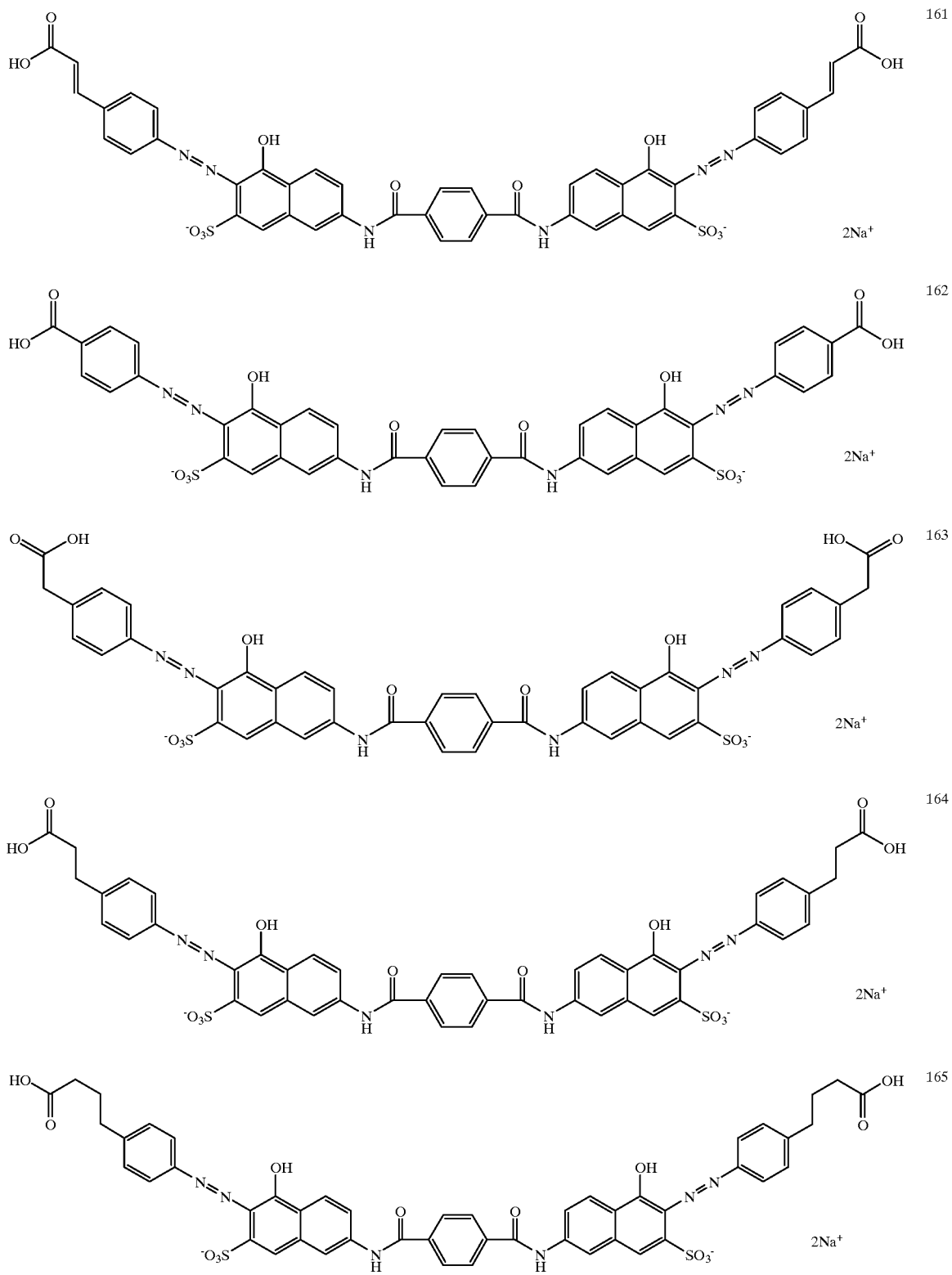

TABLE 1-continued
NOVEL COMPOUNDS
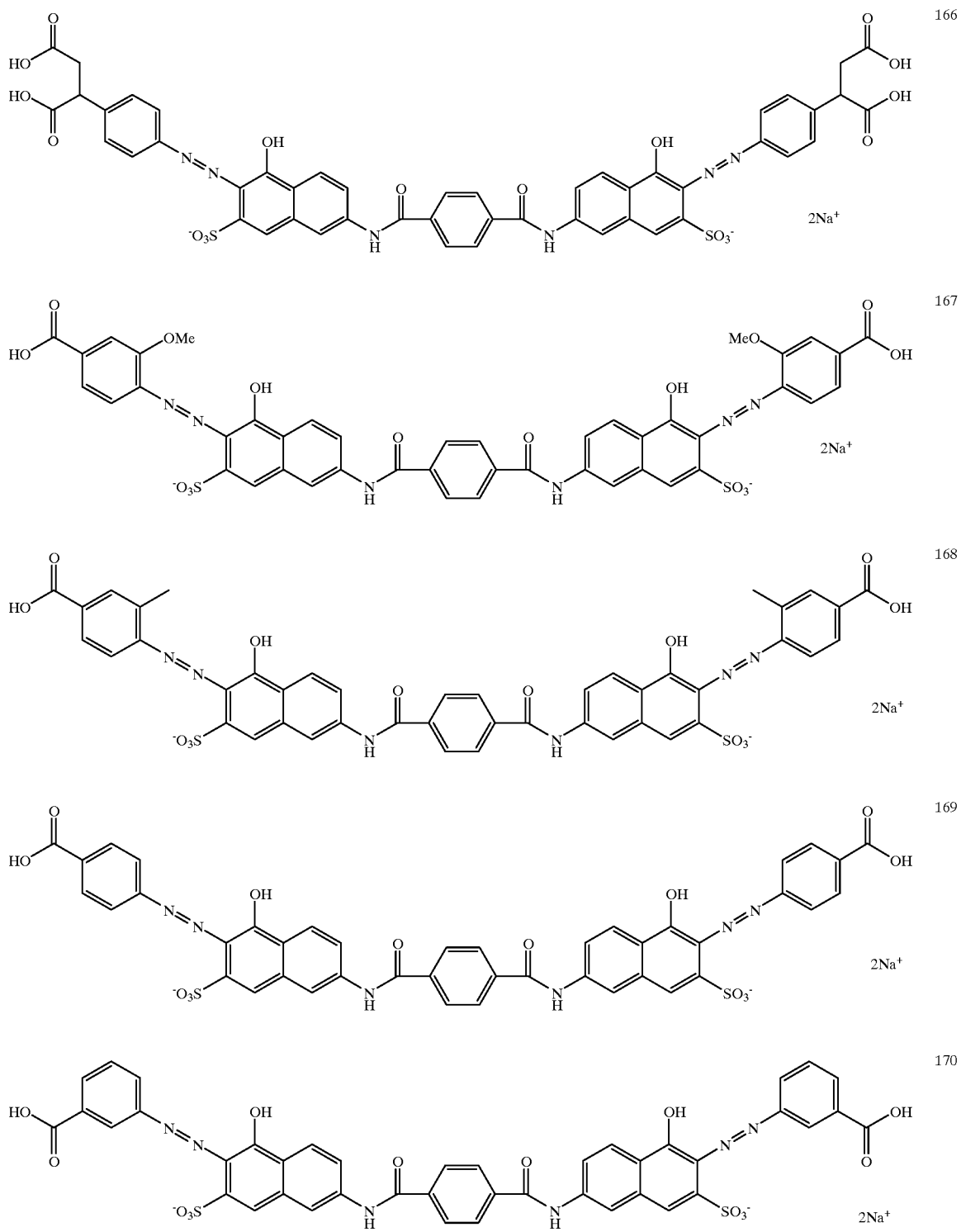

TABLE 1-continued
NOVEL COMPOUNDS
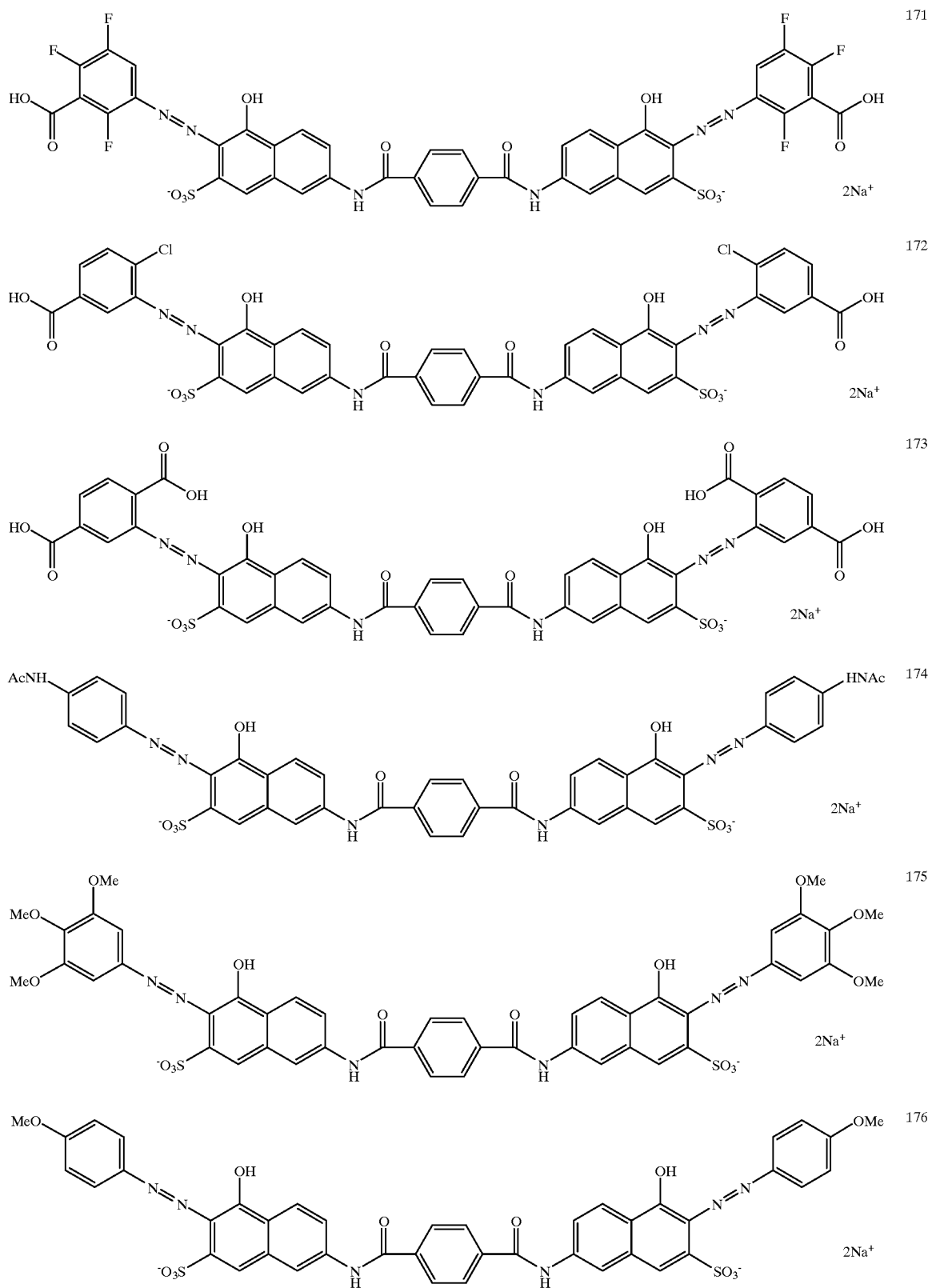

TABLE 1-continued

NOVEL COMPOUNDS

TABLE 1-continued
NOVEL COMPOUNDS
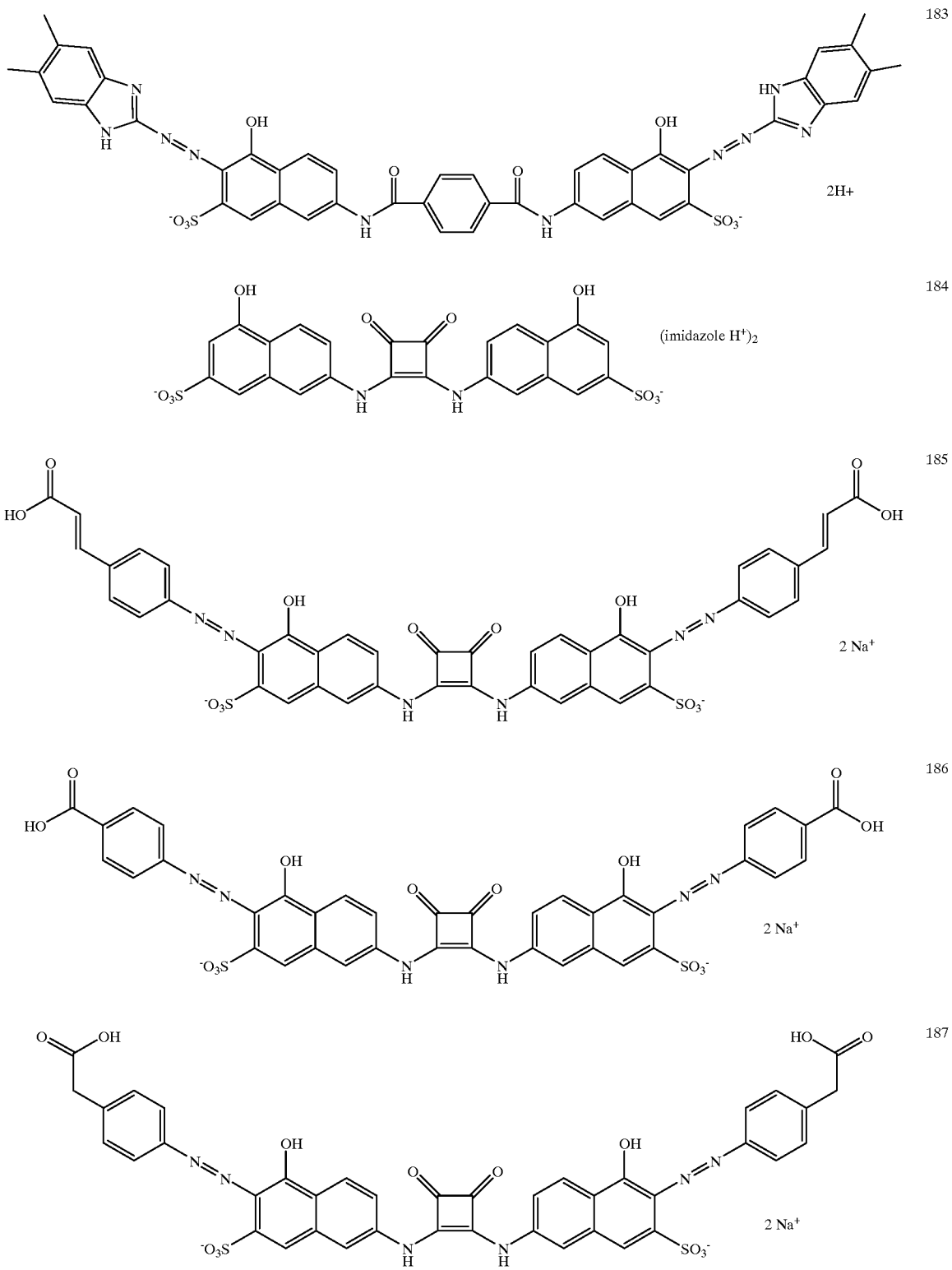

TABLE 1-continued
NOVEL COMPOUNDS
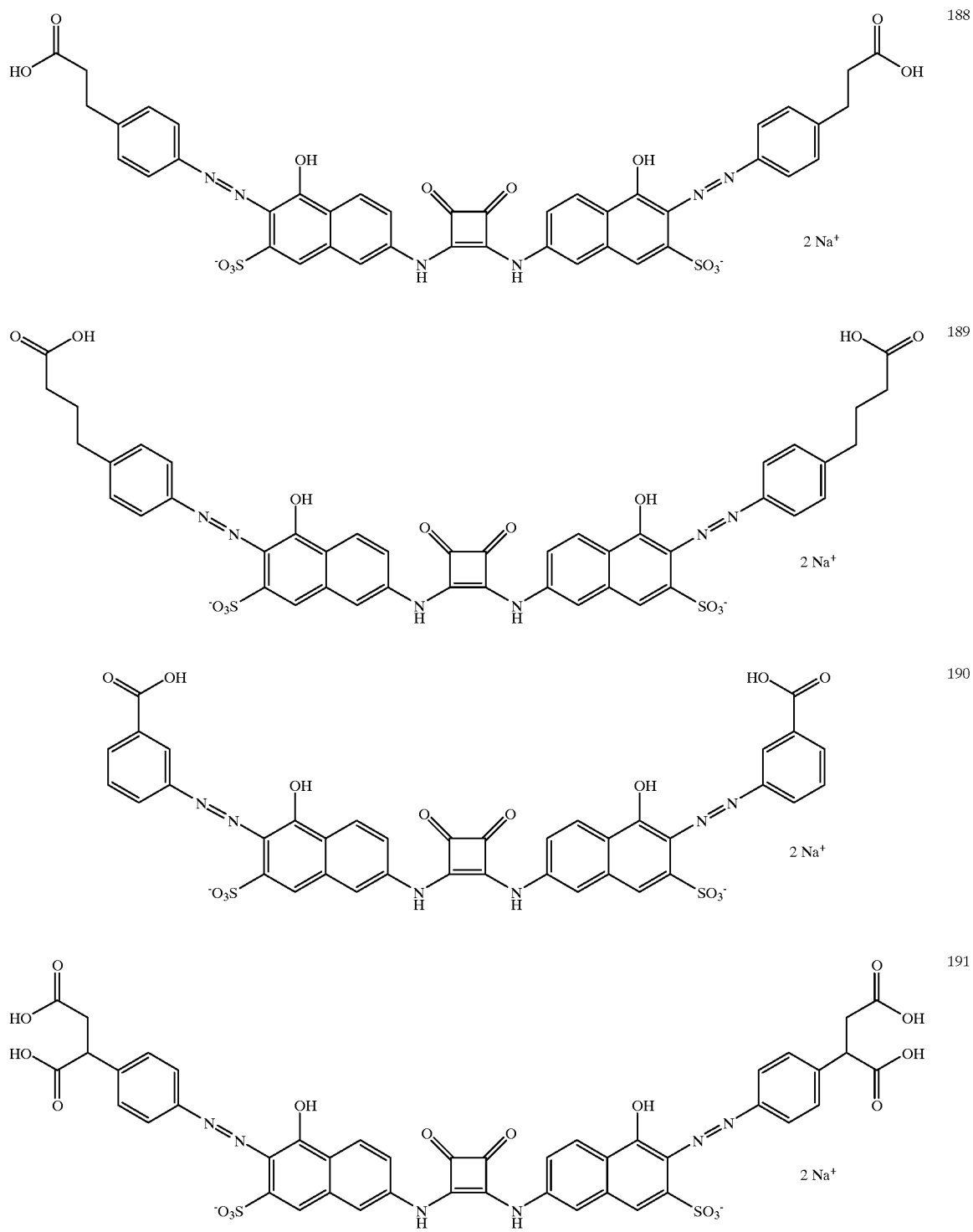

TABLE 1-continued
NOVEL COMPOUNDS
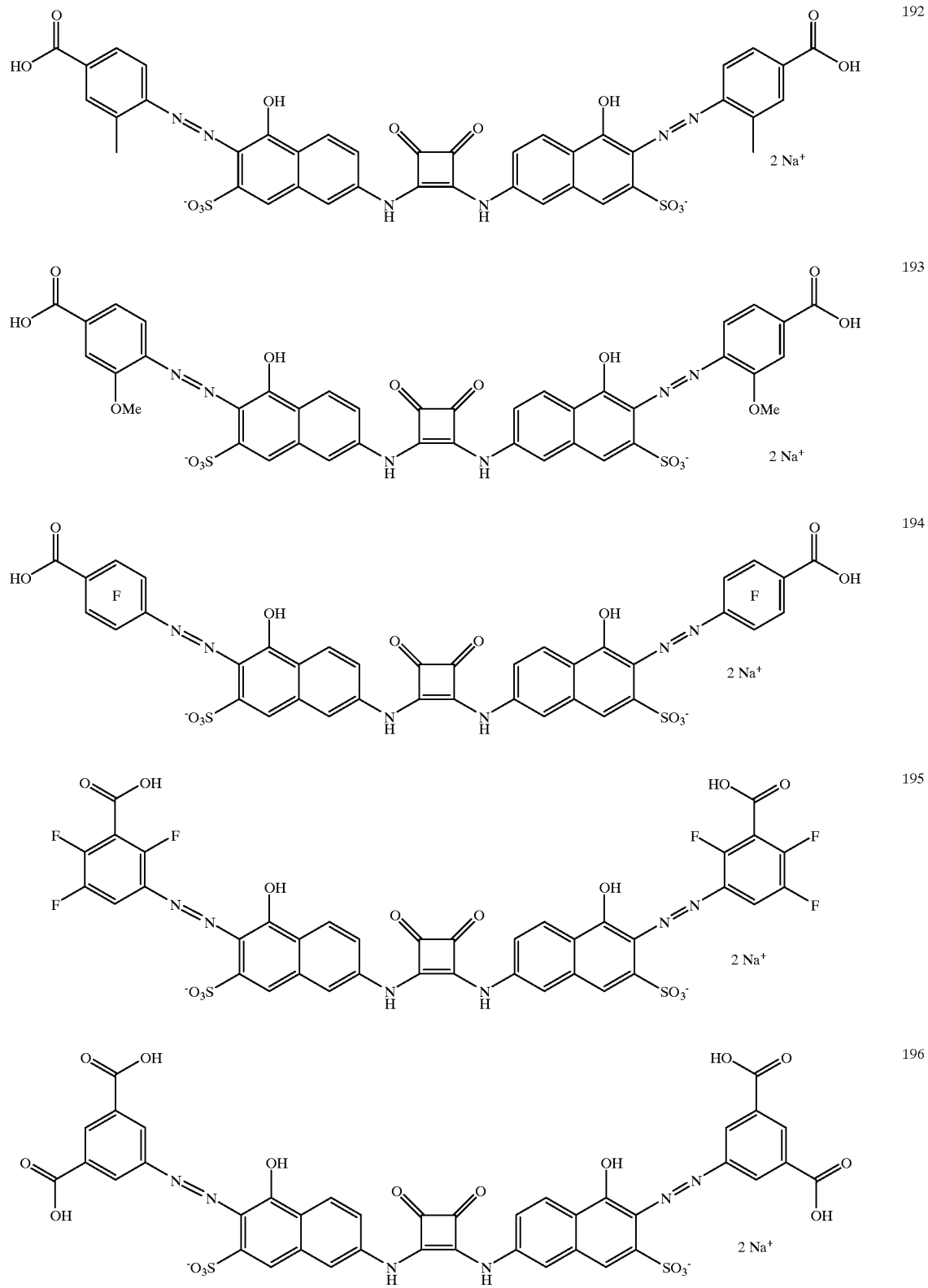
192
193
194
195
196

TABLE 1-continued

NOVEL COMPOUNDS

[Structure 197: complex bis-azo naphthalene squaraine compound with terephthalic acid groups, labeled •P]

[Structure 198: naphthalene squaraine compound with (imidazole H⁺)₂ counterion]

[Structure 199: bis-azo naphthalene squaraine with cinnamic acid groups, 2 Na⁺ counterions]

Aspects of the invention will now be illustrated by the following examples. It will be understood that these examples are intended to illustrate, and not limit, the present invention.

EXAMPLE 1

General Procedure for Symmetric Ureas

A solution of amine (2 equivalents) is dissolved in $CH_2Cl_2$ and treated with CDI in $CH_2Cl_2$ (1 equivalent), and then shaken for 12–24 hours. If substantial amounts of the product precipitates, it can be removed at this point. If no precipitate is formed, then the reaction is partitioned between water and $CH_2Cl_2$. The organic layer is dried over $Na_2SO_4$ and evaporated to give the crude urea which, if possible, is recrystallized.

General Procedure for Hetero Ureas

A solution of 4-nitrophenoxychloroformate (1 equivalent) is dissolved in $CH_2Cl_2$ and THF at a concentration such that at −78° C. no precipitate forms. A solution of the least nucleophilic amine and TEA or pyridine (1 equivalent each) in $CH_2Cl_2$ is slowly added at −78° C., stirred for 15 minutes at −78° C. and then warmed slowly to room temperature. After stirring for 45 minutes at room temperature, the second amine is added (1 equivalent) and the resulting solution is stirred for 1 to 3 days depending on the reactivity of the amine used.

The product is extracted with $Na_2CO_3$ solution (5–25% of saturation appears to work best) until the yellow color of the reaction mixture has been eliminated (approximately between 2 and 4 extractions). Sometimes a 20% $H_2SO_4$ is used to remove excess amines prior to the carbonate extractions. However, this step is omitted if no severe amine contamination is present as determined by thin layer chromatography ("TLC"), or if the final product contains a basic site. The organic extracts are dried over $Na_2SO_4$ and evaporated. If possible, the crude products are recrystallized.

EXAMPLE 2

Experimental Protocol for Analogs of Calcomine Orange

Procedures were performed in batches of 12 reactions (the limit of the centrifuge rotor) using 50 ml disposable centrifuge cones. Because some of the diazonium salts formed may be unstable, it is best to use them immediately after their formation.

A sample of the desired aniline functionality (1 eq.) is suspended or dissolved in 1 ml of water and 0.25 ml of 20 percent sulfuric acid. A solution of $NaNO_2$ (1 eq.) is added and the resulting solution is mixed for about 1–5 minutes until 95% or more material dissolves. At this point, the solution usually turns clear yellow.

The solution is then added to 5 ml of water and saturated carbonate solution is added until the pH of the mixture reaches about 9. The compound to be derivatized (J-acid (1 eq.) or carbonyl J or an analog thereof (½ eq.)) is then added, generally resulting in a deeply colored solution. The mixture is stirred at room temperature for approximately 2 hours during which water may be additionally added to aid in the mixing process. The mixture is then acidified with a 20 percent solution of sulfuric acid, diluted with water to a total volume of 35 ml, and centrifuged at 5000 G for about 30 minutes.

After centrifugation, the supernatant is removed and the precipitate is washed usually with 25 ml $H_2O$, then 5 to 15 ml of ethanol (or methanol) depending on the amount of precipitate and solubility. The resulting paste is dried overnight under a vacuum which yields the desired compound (usually black, flaky solid). The compound is then usually characterized using one dimensional NMR spectroscopy.

Oxallyl Bis(J-acid)diamide Diimidazole Salt

A mixture of oxallyl diimidazole (1.98 g), J-acid (5.00 g, dried on pump overnight), and imidazole (1.60 g, recrystalized from benzene) was diluted with DMF (20 ml, dry) and allowed to stir. After a few hours the reaction became cloudy and remained cloudy for the duration of the reaction. After 4 days the reaction mixture was centrifuged, and the pelleted material washed with ethanol (4×10–15 ml) until the liquid layer was only lightly colored. The material was dried in vacuum to yield 2.67 g of an off white powder.

General procedure for Oxallyl Bis(J-acid)diamide Azo Derivatives

A sample of an aniline (typical example is p-aminohydrocinnamic acid, 2 eq) is suspended or dissolved in 0.5 ml water and 0.25 ml of 20% $H_2SO_4$ is added. Separately oxallyl bis(J-acid)diamide diimidazole salt (1 eq) is diluted with 2 ml water and 0.4 ml saturated $Na_2CO_3$ solution. Although this mixture does not initially dissolve, the mixture is heated until dissolution occurs. If undissolved material is used, the reaction fails almost completely. A solution of $NaNO_2$ (2 eq) in 0.5 ml water is added to the starting aniline solution, and the resulting solution mixed for about 2–3 minutes (usually the solution turns clear and yellow). The solution is then added to 5 ml water and saturated carbonate solution is added until the pH of the mixture reaches about 9. The warm (may be hot), fully dissolved, oxallyl bis(J-acid)diamide diimidazole salt solution is then added, which generally results in a deeply-colored solution. The mixture is allowed to stir at room temperature for 2 hours (additional water may be added as necessary), then acidified with 20% $H_2SO_4$ (pH-1), diluted with water to a total volume of 35 ml, and centrifuged (5000 g, 30 min). The precipitate is washed with water (amount depending on the amount of precipitate, maximum of 25 ml), then with ethanol 5–15 ml (depending on its amount and solubility). The resulting paste is dried overnight under vacuum to yield the desired compound, generally as a black, flaky solid. Characterization is performed by $^1H$ NMR.

EXAMPLE 3

Preparation of Compound 160:

To 1.20 g imidazole in 20 ml $CH_2Cl_2$ was added a slurry of tera phtholyl dichloride (885 mg) in 10 ml $CH_2Cl_2$, and the reaction allowed to stir at room temperature for 15 hours. The entire mixture is evaporated in vacuum and a solution of 10 ml dry DMF, J-acid (1.90 g) and imidazole (0.88 g) was added. After stirring 23 hours at room temperature, the mixture is evaporated to a tar under vacuum and 60 ml of water was added. The initial tar dissolves then precipitates a gray powder which is isolated by centrifigation followed by washing with 2×10 ml portions of water. The product was pumped dry to yield 0.455 g of the desired product.

Preparation of Compound 161:

59 gm of 4-aminocinniaminic acid hydrochloride salt was slurred in 0.5 ml of water and 0.25 ml of 20% $H_2SO_4$ was added followed by a solution of 19.5 mg $NaNO_2$ in 0.5 ml $H_2O$. The reaction was mixed with a pipette until 95+% of the precipitate dissolved and was then added to 3 ml $H_2O$. The solution was bacisified with $Na_2CO_3$ saturated solution to pH of about 9 was reached. A solution of Compound 60 (99 mg) fully dissolved in 4 ml warm water and 0.4 ml $Na_2CO_3$ solution was added and the reaction mixture immediately turned dark purple/red. The resulting solution was allowed to stir at room temperature for 2 hours after which time it was diluted to half concentration with water and acidified with 20% $H_2SO_4$ to a pH of approximately 0. The resulting slurry was again diluted with water to ½ concentration and the precipitate isolated by centrifugation. The precipitate was washed with water (2×15 ml) and ethanol 10 ml) then dried under vacuum overnight to yield 119 mg of the desired compound.

Preparation of the Compound Series 162–173:

The following general procedure was used to run azo addition reactions in a 12 reaction format. Diazonium salts were generated from the appropriate aniline by suspending the aniline (1 equivalent) in 0.5 ml $H_2O$ and 0.1 ml 20% $H_2SO_4$, followed by the addition of 1 equivalent of $NaNO_2$ in 0.5 ml $H_2O$. The resulting mixture was mixed with a pipette until 95%+ of the material had dissolved, but never less than 30 seconds and no more than five minutes, and was then added to 5 ml $H_2O$ in a 50 ml centrifuge cone. The mixture was bacisified with $Na_2CO_3$ saturated solution to a pH greater than 9 (about 1 ml was required) 3 ml of Compound 60 solution (0.5 eq) was added (stock solution made by mixing 34 ml $H_2O$, 2 ml $Na_2CO_3$, and 455 mg Compound 60) the reaction mixture usually turned dark red in color and was set to stir while the next reaction was performed. After stirring the reactions for 1.75 hours the reactions were all acidified with 20% $H_2SO_4$ (to pH≦1) and the materials were centrifuged. The pelleted material was retained and washed with water (2×7.5 ml) and ethanol (2 ml) then dried in vacuum overnight to yield the desired products. Note that products which did not readily precipitate on acidification could some times be salvaged by addition of saturated NaCl solution, followed by only the ethanol wash. The identity of products was confirmed by $H^1$ NMR purity varied from 95+% to less than 50%. Compounds deemed clean enough for further work was tested for biological activity.

Preparation of Compound 184:

A mixture of dimethyl squareate (233 mg), J acid (774 mg), imidazole (600 mg) and dry DMF (5 ml) was heated overnight at 100° C. (total 22 hours). The reaction mixture was diluted with 25 ml ethanol, producing a precipitate which was isolated by centrifugation, washed with ethanol (30 ml), ethyl acetate (2×40 ml) and dried in vacuum to yield. 7477 g of the desired product.

Preparation of Compound 185:

47.5 mg of 4-aminocinniaminic acid hydrochloride salt was slurred in 0.5 ml of water and 0.25 ml of 20% $H_2SO_4$ was added followed by a solution of 14.2 mg $NaNO_2$ in 0.5 ml $H_2O$. The reaction was mixed with a pipette until 95+% of the precipitate dissolved and was then added to 3 ml $H_2O$. The solution was bacisified with $Na_2CO_3$ saturated solution to pH of about 9 was reached. A solution of Compound 184 (50.6 mg) fully dissolved in 2 ml warm water with enough $Na_2CO_3$ added to effect solution, was added and the reaction mixture which immediately turned dark purple/red. The resulting solution was allowed to stir at room temperature for 3 hours after which time it was diluted to half concentration with water and acidified with 20% $H_2SO_4$ to a pH less than 1. The resulting slurry was centrifuged and the precipitate was washed with water (2×20 ml) ethanol (2×5 ml) and ethyl acetate (2×5 ml) then dried under vacuum overnight to yield 62.5 mg of the desired compound.

Preparation of the Compound Series 186–197:

The following general procedure was used to run azo addition reactions in a 12 reaction format. Diazonium salts were generated from the appropriate aniline by suspending the aniline (1 equivalent) in 0.5 ml $H_2O$ and 0.25 ml 20% $H_2SO_4$, followed by the addition of 1 equivalent of $NaNO_2$ in 0.5 ml $H_2O$. The resulting mixture was mixed with a pipette until 95%+ of the material had dissolved, but never less than 30 seconds and no more than five minutes, and was then added to 5 ml $H_2O$ in a 50 ml centrifuge cone. The mixture was bacisified with 2 ml $Na_2CO_3$ saturated solution 3 ml of Compound 184 (0.5 eq ) was added (stock solution made by mixing 36 ml $H_2O$, 623 mg Compound 184, and sufficient $Na_2CO_3$ to effect solution) the reaction mixture usually turned dark red in color and was set to stir while the next reaction was performed. After stirring the reactions for 2.5 hours the reactions were all acidified with 20% $H_2SO_4$ (to pH$\leq$1, approx. 1 ml), diluted with water to 25 ml total volume and centrifuged. The pelleted material was retained and washed with water (10 ml) and ethanol (7.5 ml) and the remaining precipitate was dried in vacuum. The identity of products was confirmed by $H^1$ NMR purity varied from 95+% to less than 50%. Compounds deemed clean enough for further work were tested for biological activity.

Preparation of Compound 117:

To 1.01 g 2,6-pyridine dicarboxylic acid and 2.10 g carbonyl diimidazole was added 20 ml dry DMF. The reaction was allowed to stir at room temperature with the evolution of $CO_2$ for 22 hours. J acid was then added (2.80 g, dried under vacuum overnight prior to use) and the mixture allowed to stir an additional 24 hours. The mixture was diluted with 100 ml ethanol then with 150 ml ethyl acetate. The resulting initial tarry precipitate was discarded and the mixture was further diluted to 1000 ml volume with ethyl acetate. The resulting precipitate was isolated by centrifugation, washed with ethylacetate and dried in vacuum to yield 1.062 g of the desired product.

Preparation of Compound 118:

39.5 of 4-aminobenzoic acid was slurred in 0.5 ml of water and 0.25 ml of 20% $H_2SO_4$ was added followed by a solution of 18.6 mg $NaNO_2$ in 0.5 ml $H_2O$. The reaction was mixed with a pipette until 95+% of the precipitate dissolved and was then added to 3 ml $H_2O$. The solution was bacisified with $Na_2CO_3$ saturated solution to pH of about 9 was reached. A solution of Compound 117 (100 mg) fully dissolve din 2 ml warm water and 0.5 ml $Na_2CO_3$ solution, was added and the reaction mixture which immediately turned dark purple/red. The resulting solution was allowed to stir at room temperature for 2.5 hours after which time it was acidified with 20% $H_2SO_4$ to a pH of approximately 0 and diluted with 3 ml water. The precipitate was isolated by centrifugation washed with water (10 ml then 2×5 ml) and methanol (5 ml) and ethyl acetate (5 ml) then dried under vacuum over night to yield 92.6 mg of the desired compound.

Preparation of the Compound Series 119–130:

The following general procedure was used to run azo addition reactions in a 12 reaction format. Diazonium salts were generated from the appropriate aniline by suspending the aniline (1 equivalent) in 1.0 ml $H_2O$ and 0.25 ml 20% $H_2SO_4$, followed by the addition of 1 equivalent of $NaNO_2$ in 0.5 ml $H_2O$. The resulting mixture was mixed with a pipette until 95%+ of the material had dissolved, but never less than 30 seconds and no more than five minutes, and was then added to 5 ml $H_2O$ in a 50 ml centrifuge cone. The mixture was bacisified with 2 ml $Na_2CO_3$ saturated solution, 2 ml of Compound 117 solution (0.5 eq) was added (stock solution made by mixing 18 ml $H_2O$, 6 ml $Na_2CO_3$ and Compound 117 900 mg) the reaction mixture usually turned dark red in color and was set to stir while the next reaction was performed. After stirring the reactions for 2.25 hours the reactions were all acidified with 20% $H_2SO_4$ (2 ml), diluted to 35 ml total volume and the materials were centrifuged. The pelleted material was retained and washed with water (15 ml) and ethanol (15 ml) then dried in vacuum overnight to yield the desired products. Note that products which were excessively soluble could some times be salvaged by addition of ethyl acetate/chloroform. The identity of products was confirmed by $H^1$ NMR purity varied from 95+% to less than 50%. Compound deemed clean enough for further work were tested for biological activity.

Preparation of Compound 131:

To 1.35 g chelidonic acid and 2.60 g carbonyl di imidazole was added 10 ml dry DMF. The reaction was allowed to stir at room temperature with the evolution of $CO_2$ for 19 hours. J acid was then added (3:33 g, dried under vacuum overnight prior to use) and the mixture allowed to stir an additional 24 hours. The mixture was diluted with 100 ml ethanol and the resulting precipitate was isolated by centrifugation, washed with ethanol (3×20 ml) and ethylacetate (2×20 ml) and dried in vacuum to yield 3.006 g of the desired product as a yellow powder.

Preparation of Compound 132:

36 of 4 aminobenzoic acid was slurred in 0.6 ml of water and 0.25 ml of 20% $H_2SO_4$ was added followed by a solution of 18 mg $NaNO_2$ in 0.5 ml $H_2O$. The reaction was mixed with a pipette until 95+% of the precipitate dissolved and was then added to 3 ml $H_2O$. The solution was bacisified with $Na_2CO_3$ saturated solution to pH of about 9 was reached. A solution of Compound 131 (88.6 mg) fully dissolved in 2 ml warm water and 0.5 ml $Na_2CO_3$ solution, was added and the reaction mixture which immediately turned dark purple/red. The resulting solution was allowed to stir at room temperature for 3 hours after which time it was acidified with 20% $H_2SO_4$ to a pH of approximately 0 and diluted with 5 ml water. The precipitate was isolated by centrifugation washed with water (2×5 ml) and ethanol (5 ml) then dried under vacuum overnight to yield 85.6 mg of the desired compound.

Preparation of the Compound Series 133–144:

The following general procedure was used to run azo addition reactions in a 12 reaction format. Diazonium salts were generated from the appropriate aniline by suspending the aniline (1 equivalent) in 0.5 ml $H_2O$ and 0.25 ml 20% $H_2SO_4$, followed by the addition of 1 equivalent of $NaNO_2$ in 0.5 ml $H_2O$. The resulting mixture was mixed with a pipette until 95%+ of the material had dissolved, but never less than 30 seconds and no more than five minutes, and was then added to 5 ml $H_2O$ in a 50 ml centrifuge cone. The mixture was bacisified with 2 ml $Na_2CO_3$ saturated solution, 2 ml of Compound 131 solution (0.5 eq) was added (stock solution made by mixing 18 ml $H_2O$, 6 ml $Na_2CO_3$ and Compound 131 1.20 g) the reaction mixture usually turned dark red in color and was set to stir while the next reaction was performed. After stirring the reactions for 2 hours the reactions were all acidified with 20% $H_2SO_4$ (2 ml), diluted to 25 ml total volume and the materials were centrifuged. The pelleted material was retained and washed with water (15 ml) and ethanol (15 ml) then dried in vacuum overnight to yield the desired products. Note that products which were excessively soluble could some times be salvaged by addition of further acid and skipping the water wash. The identity of products was confirmed by $H^1$ NMR purity varied from 95+% to less than 50%. Compounds deemed clean enough for further work were tested for biological activity.

Preparation of Compound 145:

To 1.01 g chelidamic acid (hydrate, pumped overnight to dry) and 1.92 g carbonyl diimidazole was added 10 ml dry DMF. The reaction was allowed to stir at room temperature with the evolution of $CO_2$ overnight. J acid was then added (2.32 g, dried under vacuum overnight prior to use) and the mixture allowed to stir an additional 5 days. The reaction mixture was centrifuged and the initial precipitate discarded. The remaining liquid was added to 100 ml ethanol and the mixture let stand 30 minutes. The resulting precipitate was isolated by centrifugation, washed with ethanol (3×10 ml) and ethylacetate (2×10 ml) and dried in vacuum to yield 1.56 g of the desired product as a gray/brown powder.

Preparation of Compound 146:

37.5 of 4 aminobenzoic acid was slurred in 0.5 ml of water and 0.25 ml of 20% $H_2SO_4$ was added followed by a solution of 18.7 mg $NaNO_2$ in 0.5 ml $H_2O$. The reaction was mixed with a pipette until 95+% of the precipitate dissolved and was then added to 3 ml $H_2O$. The solution was bacisified with $Na_2CO_3$ saturated solution to pH of about 9 was reached. A solution of Compound 145 (99.1 mg) fully dissolved in 2 ml warm water and 0.5 ml $Na_2CO_3$ solution, was added and the reaction mixture which immediately turned dark purple/red. The resulting solution was allowed to stir at room temperature for 4.5 hours after which time it was acidified with 20% $H_2SO_4$ to a pH of approximately 0 and diluted to half concentration with water. The precipitate was isolated by centrifugation washed with water (2×20 ml) and ethanol (20 ml, then 10 ml) and ethyl acetate (2×10 ml) then dried under vacuum overnight to yield 75.7 mg of the desired compound.

Preparation of the Compound Series 147–158:

The following general procedure was used to run azo addition reactions in a 12 reaction format. Diazonium slats were generated from the appropriate aniline by suspending the aniline (1 equivalent) in 0.5 ml $H_2O$ and 0.25 ml 20% $H_2SO_4$, followed by the addition of 1 equivalent of $NaNO_2$ in 0.5 ml $H_2O$. The resulting mixture was mixed with a pipette until 95%+ of the material had dissolved, but never less than 30 seconds and no more than five minutes, and was then added to 5 ml $H_2O$ in a 50 ml centrifuge cone. The mixture was bacisified with 2 ml $Na_2CO_3$ saturated solution, 2 ml of J-2,6 40 h Compound 145 solution (0.5 eq) was added (stock solution made by mixing 18 ml $H_2O$, 6 ml $Na_2CO_3$ and Compound 145 1.20 g) the reaction mixture usually turned dark red in color and was set to stir while the next reaction was performed. After stirring the reactions for 2 hours the reactions were all acidified with 20% $H_2SO_4$ (2 ml), diluted to 30 ml total volume and the materials were centrifuged. The pelleted material was retained and washed with water (15 ml) and ethanol (30 ml) then dried in vacuum overnight to yield the desired products. Note that products which were excessively soluble in ethanol could some times by salvaged by addition ethyl acetate to the ethanol wash to initiate precipitation. The identity of products was confirmed by $H^1$ NMR purity varied from 95+% to less than 50%. Compounds deemed clean enough for further work were tested for biological activity.

EXAMPLE 4

Reverse Transcriptase Assay

Reverse transcriptase ("RT") activity is measured using a scintillation proximity assay kit available from Amersham Life Sciences, Inc., which uses a biotin/streptavidin bead capture system. RNA-dependent polymerase activity is measured using purified RH enzyme and a synthetic 17mer/50mer RNA-DNA template-primer containing biotin at the 5' end of the DNA. The template-primer, buffer, dNTP, and inhibitor are incubated for 10 minutes at 37° C. before the RT is added. The final 100 $\mu$l reaction mixture contains: 39 nm of template primer, buffer (40 mM tris HCl at pH 8.0, 10 mM $MgCl_2$, 60 mM KCl, 10 mM dithiothreitol); 75 nM of each dNTP except dTTP; 25 nM dTTP and 35 nM tritium labeled d*TTP; 10 $\mu$M inhibitor; and 1.0–2.0 $\mu$g of RT. After three minute incubation, the reaction is quenched with 40 $\mu$l of 0.56M EDTA. Then 10 $\mu$l of streptavidin SPA beads (in suspension) are added and incubated at 37° C. for 10 minutes. Finally, 850 $\mu$l of a buffer containing 10 mM Tris HCl pH 7.4 and 0.15M NaCl is added. The signal is produced by biotinylated polymers incorporating d*TTP binding to the streptavidin beads which stimulate the scintillant. The amount of d*TTP incorporated in the polymer is measured with a scintillation counter.

Compounds showing good inhibition will give a low number of counts/min (cpm). This number is related to a standard, dimethyl sulfoxide, which is given an arbitrary 100% relative activity. All cpm data in a single run are given a percent of this standard.

TABLE 2

| INHIBITOR | % RT activity remaining at 10 $\mu$M (or $IC_{50}$ if designated as such) |
|---|---|
| Compound 1 | $IC_{50}$ = 5 $\mu$M |
| Compound 4 | $IC_{50}$ = 1.5 $\mu$M |
| Compound 5 | $IC_{50}$ = 200 nM |
| Compound 6 | 84% |
| Compound 7 | 78% |
| Compound 8 | 83% |
| Compound 9 | 75% |
| Compound 10 | 88% |
| Compound 11 | 90% |
| Compound 12 | 88% |
| Compound 13 | 82% |
| Compound 14 | 90% |
| Compound 15 | 88% |
| Compound 16 | 81% |
| Compound 17 | 82% |
| Compound 19 | 80% |
| Compound 20 | 86% |
| Compound 21 | 108% |
| Compound 22 | 100% |
| Compound 23 | 100% |
| Compound 24 | 90% |
| Compound 25 | 86% |
| Compound 26 | 88% |
| Compound 27 | 80% |
| Compound 28 | 100% |
| Compound 29 | 108% |
| Compound 30 | 87% |
| Compound 31 | $IC_{50}$ = 390 nM |
| Compound 32 | $IC_{50}$ = 500 nM |
| Compound 33 | $IC_{50}$ = 500 nM |
| Compound 35 | $IC_{50}$ = 500 nM |
| Compound 36 | $IC_{50}$ = 500 nM |
| Compound 37 | 16% |
| Compound 38 | 47% |
| Compound 39 | 12% |
| Compound 40 | 31% |
| Compound 41 | 66% |
| Compound 42 | 47% |

TABLE 2-continued

| INHIBITOR | % RT activity remaining at 10 μM (or IC$_{50}$ if designated as such) |
|---|---|
| Compound 43 | 52% |
| Compound 44 | 19% |
| Compound 45 | 2.8% |
| Compound 46 | 4.6% |
| Compound 47 | 2% |
| Compound 48 | 17% |
| Compound 49 | 1% |
| Compound 50 | 1.3% |
| Compound 51 | 1.1% |
| Compound 52 | 1.3% |
| Compound 53 | IC$_{50}$ = 600 nM |
| Compound 54 | 0.6% |
| Compound 55 | 24% |
| Compound 56 | 27% |
| Compound 57 | 0.6% |
| Compound 58 | IC$_{50}$ = 800 nM |
| Compound 59 | 2.0% |
| Compound 60 | 6% |
| Compound 61 | 53% |
| Compound 75 | 85% |
| Compound 76 | 88% |
| Compound 77 | 84% |
| Compound 78 | 80% |
| Compound 79 | 78% |
| Compound 80 | 84% |
| Compound 81 | 78% |
| Compound 82 | 92% |
| Compound 83 | 77% |
| Compound 84 | 1.7% |
| Compound 86 | IC$_{50}$ = 1.2 μM |
| Compound 118 | .25% |
| Compound 119 | .29% |
| Compound 120 | .21% |
| Compound 121 | .16% |
| Compound 123 | .2% |
| Compound 124 | 1.2% |
| Compound 126 | .16% |
| Compound 127 | .14% |
| Compound 128 | 5% |
| Compound 130 | .35% |
| Compound 131 | 48% |
| Compound 132 | .19% |
| Compound 133 | .4% |
| Compound 134 | .25% |
| Compound 135 | .16% |
| Compound 137 | .53% |
| Compound 139 | .34% |
| Compound 143 | .23% |
| Compound 144 | .26% |
| Compound 145 | 47% |
| Compound 147 | .3% |
| Compound 150 | .6% |
| Compound 151 | .2% |
| Compound 153 | .15% |
| Compound 156 | 15% |
| Compound 159 | IC$_{50}$ = 220 nm |
| Compound 160 | 74% |
| Compound 161 | 25% |
| Compound 162 | 5.9% |
| Compound 163 | .1% |
| Compound 164 | .15% |
| Compound 165 | 3.7% |
| Compound 166 | .14% |
| Compound 167 | .26% |
| Compound 168 | .50% |
| Compound 169 | .15% |
| Compound 170 | .10% |
| Compound 171 | .15% |
| Compound 172 | .08% |
| Compound 173 | 27% |
| Compound 174 | 28% |
| Compound 175 | 62% |
| Compound 176 | 60% |
| Compound 177 | .17% |
| Compound 178 | 91% |
| Compound 179 | 7.5% |
| Compound 180 | 45% |
| Compound 181 | 43% |
| Compound 182 | 35% |
| Compound 183 | 36% |
| Compound 184 | IC$_{50}$ = 1000 nM |
| Compound 185 | .6% |
| Compound 186 | .5% |
| Compound 187 | .3% |
| Compound 188 | .3% |
| Compound 189 | 1.0% |
| Compound 190 | .5% |
| Compound 191 | .3% |
| Compound 192 | .3% |
| Compound 193 | .4% |
| Compound 194 | IC$_{50}$ = 440 nM |
| Compound 198 | 37% |
| Compound 199 | 1.2% |

Figure 2:
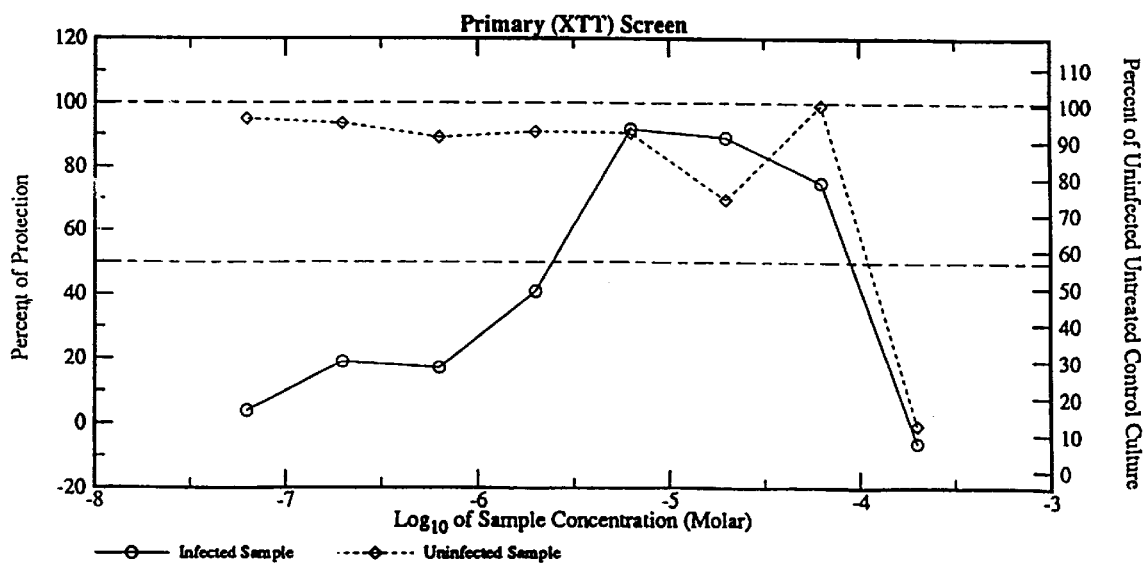

The anti-viral evaluations branch of the National Institutes of Health also ran cell-based anti-HIV (XTT) assays and reverse transcriptase (RT) assays on a number of the novel compounds. FIG. 1 graphically illustrates the reverse transcriptase assay and FIG. 2 the primary (XTT) screen run for Compound 5, which lead to a "confirmed active" conclusion. Other novel compounds of this invention were similarly confirmed as active or moderately active by these tests. These were: 31, 32, 35, 36, 53, 54, 57, 58, 91, 99, and 103.

EXAMPLE 5

Reverse Transcriptase Mutant Assays

The mutants were constructed using BspMI cassette mutagenesis as described previously by Boyer et al. (*J Virol.*, 66:1031–1039 and 7533–7537 (1992)), which is hereby incorporated by reference. The RT assay has also been previously described by Boyer et al. (*PNAS USA*, 91:4882–4886 (1994)), which is also incorporated by reference. Briefly, RNA dependent DNA polymerase activity is assayed using purified RT protein and a poly(rC).olio(dG) template-primer as the substrate. The protein (1 μg) and substrate are assayed in a total reaction volume of 100 μl containing 0.01 unites poly(rC).olio(dG), 0.02 mM dGTP, 0.002 mCi [α-$^{32}$P]dGTP, and a buffer containing 25 mM tris (pH 8.0), 75 mM KCL, 8.0 mM MgCl$_2$, 2.0 mM dithiothreitol, and 10 mM 3-[(3-cholamidopropyl) diethylammoniol]-1-propane-sulfonate containing acetylated bovine serum albumin at 100 μg/ml. The assay mixture is incubated for 30 minutes, and then stopped by the addition of 50 μl of a 10 mg/ml solution of sheared and denatured salmon sperm DNA followed by 3.0 ml 10 percent trichloroacetic acid. The labeled polymer is collected by suction filtration on Whatman glass GF/C and counted.

Inhibition results of mutant reverse transcriptase are presented in Table 3. As the data shows, carbonyl J (Compound 1) displays activity against non-nucleoside mutants as well as other mutants that have been shown to be problematic for most HIV-1 RT inhibitors.

TABLE 3

| Reverse Transcriptase Mutant | % Activity Remaining Using Carbonyl J (Compound 1) at 10 μM and 50 μM | |
|---|---|---|
| WT | 29 | 3 |
| L100I | 11 | 1 |
| K103N | 32 | 3 |
| V106A | 33 | 4 |
| Y181I | 18 | 1 |
| Y188L | 23 | 2 |
| E138K | 29 | 4 |
| P236L | 35 | 4 |
| L74V | 34 | 6 |
| M184V | 42 | 5 |
| AZT-21 | 33 | 4 |
| {M41L/D67N/K70R/T215Y/K219Q} | | |

EXAMPLE 6

Cell Culture Integrase Assay

The plasmid containing the env-deleted HIV-1 genome and the plasmid containing the chosen env gene are co-transfected into 293T cells. Viral particles released into the media are harvested and used to infect an appropriate cell line (i.e. 3T3 cells for ecotropic-MLV envelope, various murine and human cells for amphotropic-MLV env, and CD4-expressing cells for HIV-1 envelope) and selected for hygromycin resistance colonies. ("HRCs"). The number of HRCs per unit volume of stock is a direct quantification of the number of viral particles per unit volume of stock that can form a provirus. Reductions in the number of HRCs in the presence of an inhibitor indicate a block to infection somewhere between cell entry and integration. Extrachromosomal DNA harvested shortly after infection can be used to determine if there has been a block in migration of the preintegration complex ("PIC") from the cytoplasm to the nucleus. If circular DNA is not reduced relative to circular DNA generated in the absence of the inhibitor, the reductions in provirus formations are most likely due to a direct impairment of integrase activity.

EXAMPLE 7

The protocol for assaying integrase inhibitors has been previously described in Leavitt et al., *J Virology*, 66:2359–68 (1992), which is incorporated by reference herein. Briefly, inhibitor and 5 pmol of integrase are pre-incubated in 15 μl of reaction buffer (50 mM MOPS (3-[N-morpholino]propane-sulfonic acid), pH 7.0, 15 mM $MnCl_2$, and 10 mM DTT) for 5 minutes at room temperature prior to the introduction of DNA substrate which marks the start of the reaction. Once 0.5 pmol of DNA substrate is added, the reaction is allowed to continue for 20 minutes. The reaction is then stopped by the addition of 95% formamide and heating to 100° C. for 2 minutes. Potential inhibitors are screened at a single concentration, and those with inhibitory activity are then put through a dose response assay to determine the concentration at which integrase activity is decreased by 50% ($IC_{50}$).

TABLE 4

| Inhibitor | Inhibition of 3' processing activity ($IC_{50}$) | Inhibition of strand transfer ($IC_{50}$) |
|---|---|---|
| Compound 1 | 2.5 μM | 2.5 μM |
| Compound 4 | 2.0 μM | 2.0 μM |
| Compound 5 | 0.9 μM | 1.0 μM |
| Compound 31 | 0.4 μM | 0.7 μM |
| Compound 32 | 2.0 μM | 0.7 μM |
| Compound 33 | 0.3 μM | 0.6 μM |
| Compound 34 | 2.0 μM | 2.0 μM |
| Compound 35 | 0.8 μM | 2.0 μM |
| Compound 36 | 0.8 μM | 1.0 μM |
| Compound 37 | >3 μM | >3 μM |
| Compound 38 | >3 μM | >3 μM |
| Compound 39 | 2.0 μM | 3.0 μM |
| Compound 40 | >3 μM | >3 μM |
| Compound 41 | >20 μM | >20 μM |
| Compound 42 | >3 μM | >3 μM |
| Compound 43 | >20 μM | >20 μM |
| Compound 45 | >3 μM | >3 μM |
| Compound 46 | >3 μM | >3 μM |
| Compound 47 | >3 μM | >3 μM |
| Compound 48 | >3 μM | >3 μM |
| Compound 49 | 2.0 μM | 1.0 μM |
| Compound 50 | 2.0 μM | 2.0 μM |
| Compound 51 | 0.5 μM | 0.9 μM |
| Compound 52 | 0.2 μM | 0.5 μM |
| Compound 53 | 0.5 μM | 2.0 μM |
| Compound 54 | 4.0 μM | 2.0 μM |
| Compound 55 | >3 μM | >3 μM |
| Compound 56 | >3 μM | >3 μM |
| Compound 57 | 0.6 μM | 0.9 μM |
| Compound 58 | 0.2 μM | 0.6 μM |
| Compound 59 | 2.0 μM | 1.0 μM |
| Compound 60 | 0.8 μM | 2.0 μM |
| Compound 61 | >3 μM | >3 μM |
| Compound 62 | 0.4 μM | 0.5 μM |
| Compound 64 | >3 μM | >3 μM |
| Compound 65 | 0.8 μM | 0.5 μM |
| Compound 66 | 0.8 μM | 0.5 μM |
| Compound 67 | 0.09 μM | 0.25 μM |
| Compound 68 | 0.4 μM | 0.4 μM |
| Compound 69 | 0.7 μM | 0.9 μM |
| Compound 70 | >3 μM | >3 μM |
| Compound 71 | 0.9 μM | 1.0 μM |
| Compound 72 | 1.0 μM | 0.5 μM |
| Compound 73 | 1.0 μM | 0.6 μM |
| Compound 74 | 2.0 μM | 1.5 μM |
| Compound 93 | 0.9 μM | 0.5 μM |
| Compound 94 | 1.0 μM | 0.4 μM |
| Compound 95 | 0.4 μM | 0.7 μM |
| Compound 96 | 0.5 μM | 0.4 μM |
| Compound 97 | 0.5 μM | 1.0 μM |
| Compound 98 | 0.4 μM | 0.2 μM |
| Compound 99 | | 0.3 μM |
| Compound 100 | 0.4 μM | 0.7 μM |
| Compound 101 | 0.5 μM | 2.0 μM |
| Compound 102 | 0.6 μM | 0.7 μM |
| Compound 103 | <1 μM | <1 μM |
| Compound 104 | 0.6 μM | 0.4 μM |
| Compound 106 | 1.5 μM | 0.4 μM |
| Compound 107 | 0.7 μM | 0.5 μM |
| Compound 108 | 1.0 μM | 0.7 μM |
| Compound 110 | 1.1 μM | 0.4 μM |
| Compound 114 | 1.0 μM | 0.3 μM |

It is to be understood that while the invention has been described above in conjunction with preferred specific embodiments, the description and examples are intended to illustrate and not limit the scope of the invention, which is defined by the scope of the appended claims.

What is claimed is:

1. A method for treating a retroviral infection in a patient in need thereof comprising administering to the patient a therapeutically effective amount of a naphthol compound, or a pharmaceutically acceptable salt thereof, having the structure:

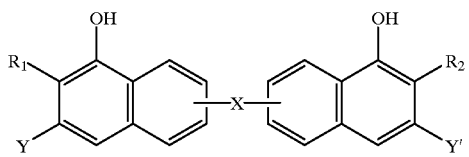

wherein $R_1$ and $R_2$ each is selected from a group consisting of substituted aryl ($C_6$–$C_{12}$), unsubstituted aryl ($C_6$–$C_{12}$), substituted heteroaryl ($C_2$–$C_{12}$) and unsubstituted heteroaryl ($C_1$–$C_{12}$), wherein the heteroatom is nitrogen, bound via an azo or amide group, provided that neither $R_1$ nor $R_2$ contains a —$SO_3H$ group, Y and Y' each is selected from the group consisting of —$SO_3H$, —COOH esters of —$SO_3H$ and —COOH, and tetrazolyl, and X is a substantially rigid linker, wherein the linker is:
 (a) derived from the group consisting of urea, thiourea, oxalyl, malonyl, carbamate, succinyl, and vinylogous amide;
 (b) an aryl or heteroaryl, where the heteroatom is nitrogen or oxygen; or
 (c) a squarate or a cage structure.

2. The method as in claim 1 wherein the naphthol compound or salt thereof is administered orally, topically, or by injection.

3. A method for treating a retroviral infection in a patient in need thereof comprising:
 administering to the patient a therapeutically effective amount of a napthol compound, or a pharmaceutically acceptable salt thereof, wherein the naphthol or salt administered is:

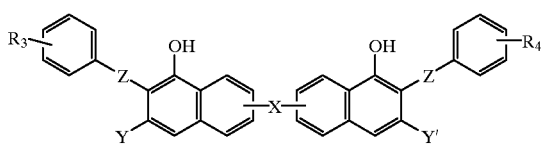

where Y and Y' each is selected from the group consisting of sulfo, carboxyl, tetrazolyl, sulfonic acid ester, and sulfonic acid thioester, X is a substantially rigid linker wherein the linker is:
 (a) derived from the group consisting of urea, thiourea, oxalyl, malonyl, carbamate, succinyl, and vinylogous amide;
 (b) an aryl or heteroaryl, where the heteroatom is nitrogen or oxygen; or
 (c) a squarate or a cage structure,
Z is an azo or amide linkage, and one or both of $R_3$ and $R_4$ is a carboxyl, a triazolyl, or a tetrazolyl group, with the proviso that when sulfo groups are present there are no more than two.

4. A method for treating a retroviral infection in a patient in need thereof comprising:
 administering to the patient a therapeutically effective amount of a napthol compound, or a pharmaceutically acceptable salt thereof, wherein the naphthol or salt administered is

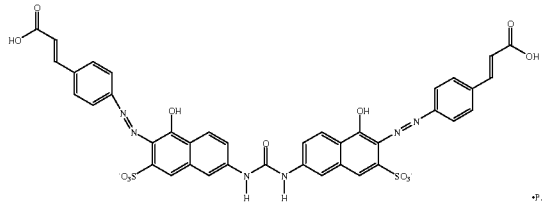

5. A method for treating a retroviral infection in a patient in need thereof comprising:
 administering to the patient a therapeutically effective amount of a napthol compound, or a pharmaceutically acceptable salt thereof, wherein the naphthol or salt administered is

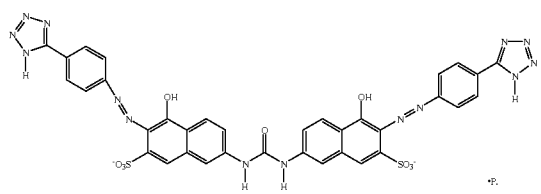

6. A compound having the structure

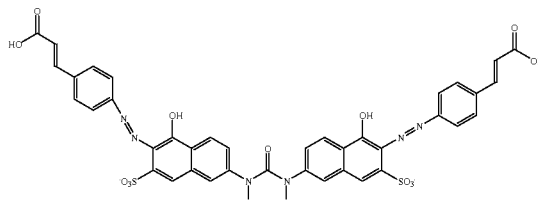

where P is one or more counterions.

7. A compound having the structure

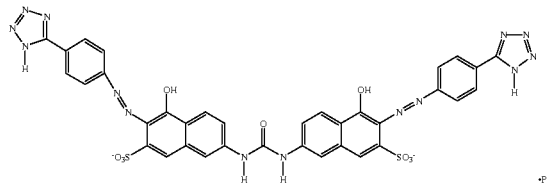

where P is one or more counterions.

8. A compound having the structure

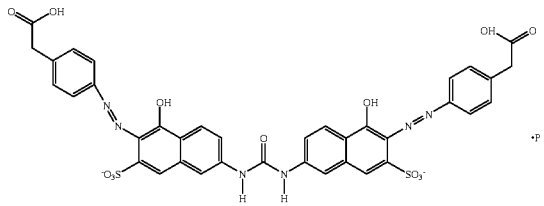

where P is one or more counterions.

9. A compound having the structure
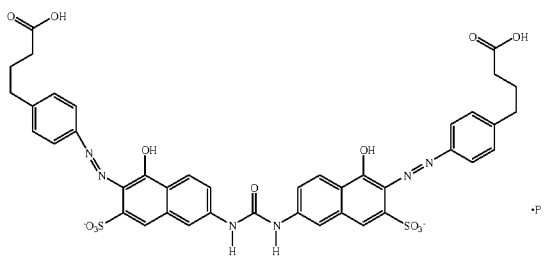
where P is one or more counterions.
10. A compound having the structure
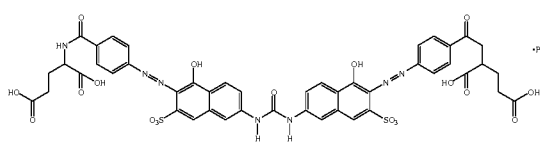
where P is one or more counterions.
11. A compound having the structure
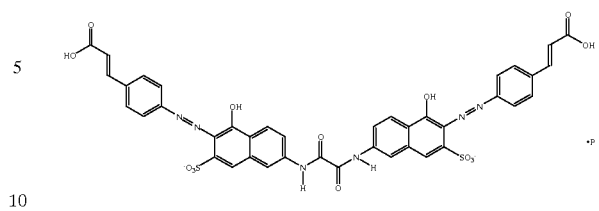
where P is one or more counterions.
12. A compound having the structure
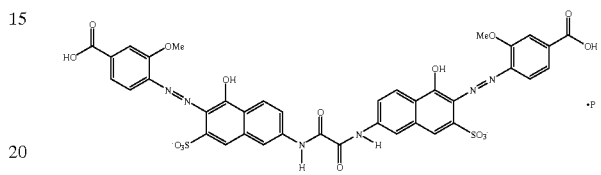
where P is one or more counterions.
13. A compound having the structure
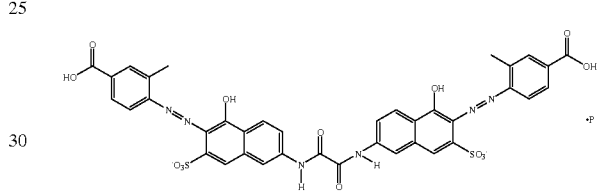
where P is one or more counterions.
* * * * *